United States Patent
Utley et al.

(10) Patent No.: US 8,439,908 B2
(45) Date of Patent: May 14, 2013

(54) ABLATION IN THE GASTROINTESTINAL TRACT TO ACHIEVE HEMOSTASIS AND ERADICATE LESIONS WITH A PROPENSITY FOR BLEEDING

(75) Inventors: David S. Utley, Redwood City, CA (US); Michael P. Wallace, Pleasanton, CA (US); Brent C. Gerberding, San Jose, CA (US)

(73) Assignee: Covidien LP, Mansfield, MA (US)

( * ) Notice: Subject to any disclaimer, the term of this patent is extended or adjusted under 35 U.S.C. 154(b) by 1349 days.

(21) Appl. No.: 12/167,931

(22) Filed: Jul. 3, 2008

(65) Prior Publication Data

US 2009/0012513 A1  Jan. 8, 2009

Related U.S. Application Data

(60) Provisional application No. 60/958,566, filed on Jul. 6, 2007.

(51) Int. Cl.
*A61B 18/04* (2006.01)
*A61B 18/18* (2006.01)

(52) U.S. Cl.
USPC ............ 606/34; 606/20; 606/21; 606/27; 606/32; 606/40; 606/41

(58) Field of Classification Search ........... 606/21, 606/27–33, 40, 41, 49
See application file for complete search history.

(56) References Cited

U.S. PATENT DOCUMENTS

| 552,832 A | 1/1896 | Fort |
| 3,901,241 A | 8/1975 | Allen, Jr. |
| 3,924,628 A | 12/1975 | Droegemueller et al. |
| 4,011,872 A | 3/1977 | Komiya |

(Continued)

FOREIGN PATENT DOCUMENTS

| DE | 3838840 | 5/1990 |
| DE | 4303882 | 8/1994 |

(Continued)

OTHER PUBLICATIONS

Castell, D.O. Gastroesophageal Reflux Disease: Current Strategies for Patient Management. Arch Fam Med. 1996; 5(4):221-227.

(Continued)

*Primary Examiner* — Nicholas Lucchesi
*Assistant Examiner* — Leah Stohr
(74) *Attorney, Agent, or Firm* — Holland & Hart LLP

(57) ABSTRACT

Devices and methods are provided for the ablation of regions of the digestive tract to achieve hemostasis and to eradicate chronically bleeding lesions as occur with gastric antral vascular ectasia (GAVE), portal hypertensive gastropathy (PHG), radiation proctopathy and colopathy, arteriovenous malformations, and angiodysplasia. Ablation is typically provided in a wide-field manner, and in conjunction with sufficient pressure to achieve coaptive coagulation. Ablation, as provided the invention, starts at the mucosa and penetrates deeper into the gastrointestinal wall in a controlled manner. Ablation control may be exerted by way of electrode design and size, energy density, power density, number of applications, pattern of applications, and pressure. Control may also be provided by a fractional ablation that ablates some tissue within a target region and leaves a portion substantially unaffected. Embodiments of the device include an ablational electrode array that spans 360 degrees and an array that spans an arc of less than 360 degrees.

50 Claims, 43 Drawing Sheets

U.S. PATENT DOCUMENTS

| | | | |
|---|---|---|---|
| 4,304,239 A | 12/1981 | Perlin | |
| 4,311,154 A | 1/1982 | Sterzer et al. | |
| 4,407,298 A | 10/1983 | Lentz et al. | |
| 4,411,266 A | 10/1983 | Cosman | |
| 4,522,205 A * | 6/1985 | Taylor et al. | 606/49 |
| 4,532,924 A | 8/1985 | Auth et al. | |
| 4,565,200 A | 1/1986 | Cosman | |
| 4,640,298 A | 2/1987 | Pless et al. | |
| 4,658,836 A | 4/1987 | Turner | |
| 4,662,383 A | 5/1987 | Sogawa et al. | |
| 4,674,481 A | 6/1987 | Boddie, Jr. et al. | |
| 4,676,258 A | 6/1987 | Inokuchi et al. | |
| 4,709,698 A | 12/1987 | Johnston et al. | |
| 4,765,331 A | 8/1988 | Petruzzi et al. | |
| 4,776,349 A | 10/1988 | Nashef et al. | |
| 4,860,744 A | 8/1989 | Johnson et al. | |
| 4,887,614 A | 12/1989 | Shirakami et al. | |
| 4,895,138 A | 1/1990 | Yabe | |
| 4,907,589 A | 3/1990 | Cosman | |
| 4,930,521 A | 6/1990 | Metzger et al. | |
| 4,943,290 A | 7/1990 | Rexroth et al. | |
| 4,947,842 A | 8/1990 | Marchosky et al. | |
| 4,949,147 A | 8/1990 | Bacuvier | |
| 4,955,377 A | 9/1990 | Lennox et al. | |
| 4,966,597 A | 10/1990 | Cosman | |
| 4,969,890 A | 11/1990 | Sugita et al. | |
| 4,976,711 A | 12/1990 | Parins et al. | |
| 4,979,948 A | 12/1990 | Geddes et al. | |
| 4,998,539 A | 3/1991 | Delsanti | |
| 5,006,119 A | 4/1991 | Acker et al. | |
| 5,010,895 A | 4/1991 | Maurer et al. | |
| 5,019,075 A | 5/1991 | Spears et al. | |
| 5,035,696 A | 7/1991 | Rydell | |
| 5,045,056 A | 9/1991 | Behl | |
| 5,046,512 A | 9/1991 | Murchie | |
| 5,047,028 A | 9/1991 | Qian | |
| 5,056,532 A | 10/1991 | Hull et al. | |
| 5,057,107 A | 10/1991 | Parins et al. | |
| 5,078,717 A | 1/1992 | Parins et al. | |
| 5,083,565 A | 1/1992 | Parins | |
| 5,084,044 A | 1/1992 | Quint | |
| 5,088,979 A | 2/1992 | Filipi et al. | |
| 5,100,423 A | 3/1992 | Fearnot | |
| 5,106,360 A | 4/1992 | Ishiwara et al. | |
| 5,117,828 A | 6/1992 | Metzger et al. | |
| 5,122,137 A | 6/1992 | Lennox | |
| 5,125,928 A | 6/1992 | Parins et al. | |
| 5,151,100 A | 9/1992 | Abele et al. | |
| 5,156,151 A | 10/1992 | Imran | |
| 5,163,938 A | 11/1992 | Kambara et al. | |
| 5,171,299 A | 12/1992 | Heitzmann et al. | |
| 5,190,541 A | 3/1993 | Abele et al. | |
| 5,197,963 A | 3/1993 | Parins | |
| 5,197,964 A | 3/1993 | Parins | |
| 5,215,103 A | 6/1993 | Desai | |
| 5,236,413 A | 8/1993 | Feiring | |
| 5,242,441 A | 9/1993 | Avitall | |
| 5,255,679 A | 10/1993 | Imran | |
| 5,256,138 A | 10/1993 | Vurek et al. | |
| 5,257,451 A | 11/1993 | Edwards et al. | |
| 5,257,635 A | 11/1993 | Langberg | |
| 5,263,493 A | 11/1993 | Avitall | |
| 5,275,162 A | 1/1994 | Edwards et al. | |
| 5,275,169 A | 1/1994 | Afromowitz et al. | |
| 5,277,201 A | 1/1994 | Stern | |
| 5,281,216 A | 1/1994 | Klicek | |
| 5,281,217 A | 1/1994 | Edwards et al. | |
| 5,281,218 A | 1/1994 | Imran | |
| 5,290,286 A | 3/1994 | Parins | |
| 5,292,321 A | 3/1994 | Lee | |
| 5,293,869 A | 3/1994 | Edwards et al. | |
| 5,309,910 A | 5/1994 | Edwards et al. | |
| 5,313,943 A | 5/1994 | Houser et al. | |
| 5,314,438 A | 5/1994 | Shturman | |
| 5,314,466 A | 5/1994 | Stern et al. | |
| 5,316,020 A | 5/1994 | Truffer | |
| 5,324,284 A | 6/1994 | Imran | |
| 5,327,905 A | 7/1994 | Avitall | |
| 5,328,467 A | 7/1994 | Edwards et al. | |
| 5,336,222 A | 8/1994 | Durgin, Jr. et al. | |
| 5,345,936 A | 9/1994 | Pomeranz et al. | |
| 5,348,554 A | 9/1994 | Imran et al. | |
| 5,363,861 A | 11/1994 | Edwards et al. | |
| 5,365,926 A | 11/1994 | Desai | |
| 5,366,490 A | 11/1994 | Edwards et al. | |
| 5,368,557 A | 11/1994 | Nita et al. | |
| 5,368,592 A | 11/1994 | Stern et al. | |
| 5,370,675 A | 12/1994 | Edwards et al. | |
| 5,370,678 A | 12/1994 | Edwards et al. | |
| 5,372,138 A | 12/1994 | Crowley et al. | |
| 5,375,594 A | 12/1994 | Cueva | |
| 5,383,874 A | 1/1995 | Jackson et al. | |
| 5,383,876 A | 1/1995 | Nardella | |
| 5,383,917 A | 1/1995 | Desai et al. | |
| 5,385,544 A | 1/1995 | Edwards et al. | |
| 5,397,339 A | 3/1995 | Desai | |
| 5,398,683 A | 3/1995 | Edwards et al. | |
| 5,401,272 A | 3/1995 | Perkins | |
| 5,403,311 A | 4/1995 | Abele et al. | |
| 5,409,453 A | 4/1995 | Lundquist et al. | |
| 5,409,483 A | 4/1995 | Campbell et al. | |
| 5,411,025 A | 5/1995 | Webster, Jr. | |
| 5,413,573 A | 5/1995 | Koivukangas | |
| 5,415,657 A | 5/1995 | Taymor-Luria | |
| 5,421,819 A | 6/1995 | Edwards et al. | |
| 5,423,808 A | 6/1995 | Edwards et al. | |
| 5,423,811 A | 6/1995 | Ellman et al. | |
| 5,423,812 A | 6/1995 | Ellman et al. | |
| 5,425,704 A | 6/1995 | Sakurai et al. | |
| 5,428,658 A | 6/1995 | Oettinger et al. | |
| 5,433,739 A | 7/1995 | Sluijter et al. | |
| 5,435,805 A | 7/1995 | Edwards | |
| 5,441,499 A | 8/1995 | Fritzsch | |
| 5,443,470 A | 8/1995 | Stern et al. | |
| 5,454,782 A | 10/1995 | Perkins | |
| 5,454,809 A | 10/1995 | Janssen | |
| 5,456,662 A | 10/1995 | Edwards et al. | |
| 5,456,682 A | 10/1995 | Edwards et al. | |
| 5,458,571 A | 10/1995 | Lampropoulos et al. | |
| 5,458,596 A | 10/1995 | Lax et al. | |
| 5,458,597 A | 10/1995 | Edwards et al. | |
| 5,462,545 A | 10/1995 | Wang et al. | |
| 5,465,717 A | 11/1995 | Imran et al. | |
| 5,470,308 A | 11/1995 | Edwards et al. | |
| 5,471,982 A | 12/1995 | Edwards et al. | |
| 5,472,441 A | 12/1995 | Edwards et al. | |
| 5,484,400 A | 1/1996 | Edwards et al. | |
| 5,486,161 A | 1/1996 | Lax et al. | |
| 5,490,984 A | 2/1996 | Freed | |
| 5,496,271 A | 3/1996 | Burton et al. | |
| 5,496,311 A | 3/1996 | Abele et al. | |
| 5,500,012 A | 3/1996 | Brucker et al. | |
| 5,505,728 A | 4/1996 | Ellman et al. | |
| 5,505,730 A | 4/1996 | Edwards | |
| 5,507,743 A | 4/1996 | Edwards et al. | |
| 5,509,419 A | 4/1996 | Edwards et al. | |
| 5,514,130 A | 5/1996 | Baker | |
| 5,514,131 A | 5/1996 | Edwards et al. | |
| 5,517,989 A | 5/1996 | Frisbie et al. | |
| 5,520,684 A | 5/1996 | Imran | |
| 5,522,815 A | 6/1996 | Burgin, Jr. et al. | |
| 5,524,622 A | 6/1996 | Wilson | |
| 5,531,676 A | 7/1996 | Edwards et al. | |
| 5,531,677 A | 7/1996 | Lundquist et al. | |
| 5,533,958 A | 7/1996 | Wilk | |
| 5,536,240 A | 7/1996 | Edwards et al. | |
| 5,536,267 A | 7/1996 | Edwards et al. | |
| 5,540,655 A | 7/1996 | Edwards et al. | |
| 5,540,679 A | 7/1996 | Fram et al. | |
| 5,542,916 A | 8/1996 | Hirsch et al. | |
| 5,542,928 A | 8/1996 | Evans et al. | |
| 5,549,644 A | 8/1996 | Lundquist et al. | |
| 5,549,661 A | 8/1996 | Korkis et al. | |
| RE35,330 E | 9/1996 | Malone et al. | |
| 5,554,110 A | 9/1996 | Edwards et al. | |
| 5,556,377 A | 9/1996 | Rosen et al. | |
| 5,558,672 A | 9/1996 | Edwards et al. | |

| | | | | | | |
|---|---|---|---|---|---|---|
| 5,558,673 A | 9/1996 | Edwards et al. | 6,073,052 A | 6/2000 | Zelickson et al. | |
| 5,562,720 A | 10/1996 | Stern et al. | 6,086,558 A | 7/2000 | Bower et al. | |
| 5,566,221 A | 10/1996 | Smith et al. | 6,091,993 A | 7/2000 | Bouchier et al. | |
| 5,569,241 A | 10/1996 | Edwards | 6,091,995 A | 7/2000 | Ingle et al. | |
| 5,571,116 A | 11/1996 | Bolanos et al. | 6,092,528 A | 7/2000 | Edwards | |
| 5,578,007 A | 11/1996 | Imran | 6,095,966 A | 8/2000 | Chornenky et al. | |
| 5,588,432 A | 12/1996 | Crowley | 6,096,054 A | 8/2000 | Wyzgala et al. | |
| 5,588,960 A | 12/1996 | Edwards et al. | 6,102,908 A | 8/2000 | Tu et al. | |
| 5,591,195 A | 1/1997 | Taheri et al. | 6,112,123 A | 8/2000 | Kelleher et al. | |
| 5,599,345 A | 2/1997 | Edwards et al. | 6,120,434 A | 9/2000 | Kimura et al. | |
| 5,609,151 A | 3/1997 | Mulier et al. | 6,123,703 A | 9/2000 | Tu et al. | |
| 5,621,780 A | 4/1997 | Smith et al. | 6,123,718 A * | 9/2000 | Tu et al. | 607/113 |
| 5,624,439 A | 4/1997 | Edwards et al. | 6,138,046 A | 10/2000 | Dalton | |
| 5,651,780 A | 7/1997 | Jackson et al. | 6,142,994 A | 11/2000 | Swanson et al. | |
| 5,651,788 A | 7/1997 | Fleischer et al. | 6,146,149 A | 11/2000 | Daoud | |
| 5,658,278 A | 8/1997 | Imran et al. | 6,149,647 A | 11/2000 | Tu et al. | |
| 5,672,153 A | 9/1997 | Lax et al. | 6,162,237 A | 12/2000 | Chan | |
| 5,676,674 A | 10/1997 | Bolanos et al. | 6,179,836 B1 | 1/2001 | Eggers et al. | |
| 5,688,266 A | 11/1997 | Edwards et al. | 6,182,666 B1 | 2/2001 | Dobak, III | |
| 5,688,490 A | 11/1997 | Tournier et al. | 6,183,468 B1 | 2/2001 | Swanson et al. | |
| 5,702,438 A | 12/1997 | Avitall | 6,197,022 B1 | 3/2001 | Baker | |
| 5,709,224 A | 1/1998 | Behl et al. | 6,237,355 B1 | 5/2001 | Li | |
| 5,713,942 A | 2/1998 | Stern et al. | 6,238,392 B1 | 5/2001 | Long | |
| 5,716,410 A | 2/1998 | Wang et al. | 6,245,065 B1 | 6/2001 | Panescu et al. | |
| 5,720,293 A | 2/1998 | Quinn et al. | 6,254,598 B1 | 7/2001 | Edwards et al. | |
| 5,730,128 A | 3/1998 | Pomeranz et al. | 6,258,087 B1 | 7/2001 | Edwards et al. | |
| 5,732,698 A | 3/1998 | Swanson et al. | 6,273,886 B1 | 8/2001 | Edwards et al. | |
| 5,738,096 A | 4/1998 | Ben-Haim | 6,321,121 B1 | 11/2001 | Zelickson et al. | |
| 5,748,699 A | 5/1998 | Smith | 6,325,798 B1 | 12/2001 | Edwards et al. | |
| 5,769,846 A | 6/1998 | Edwards et al. | 6,325,800 B1 | 12/2001 | Durgin et al. | |
| 5,769,880 A | 6/1998 | Truckai et al. | 6,338,726 B1 | 1/2002 | Edwards et al. | |
| 5,779,698 A | 7/1998 | Clayman et al. | 6,355,031 B1 | 3/2002 | Edwards et al. | |
| 5,797,835 A | 8/1998 | Green | 6,355,032 B1 | 3/2002 | Hovda et al. | |
| 5,797,903 A | 8/1998 | Swanson et al. | 6,358,245 B1 | 3/2002 | Edwards et al. | |
| 5,800,334 A | 9/1998 | Wilk | 6,363,937 B1 | 4/2002 | Hovda et al. | |
| 5,800,429 A | 9/1998 | Edwards | 6,383,181 B1 * | 5/2002 | Johnston et al. | 606/24 |
| 5,807,261 A | 9/1998 | Benaron et al. | 6,394,949 B1 | 5/2002 | Crowley et al. | |
| 5,820,629 A | 10/1998 | Cox | 6,402,744 B2 | 6/2002 | Edwards et al. | |
| 5,823,197 A | 10/1998 | Edwards | 6,405,732 B1 | 6/2002 | Edwards et al. | |
| 5,823,955 A | 10/1998 | Kuck et al. | 6,409,723 B1 | 6/2002 | Edwards | |
| 5,827,273 A | 10/1998 | Edwards | H0002037 H | 7/2002 | Yates et al. | |
| 5,830,129 A | 11/1998 | Baer et al. | 6,415,016 B1 | 7/2002 | Chornenky et al. | |
| 5,830,213 A | 11/1998 | Panescu et al. | 6,416,511 B1 | 7/2002 | Lesh et al. | |
| 5,833,688 A | 11/1998 | Sieben et al. | 6,423,058 B1 | 7/2002 | Edwards et al. | |
| 5,836,874 A | 11/1998 | Swanson et al. | 6,425,877 B1 | 7/2002 | Edwards | |
| 5,842,984 A | 12/1998 | Avitall | 6,428,536 B2 | 8/2002 | Panescu et al. | |
| 5,846,196 A | 12/1998 | Siekmeyer et al. | 6,432,104 B1 | 8/2002 | Durgin et al. | |
| 5,860,974 A | 1/1999 | Abele | 6,440,128 B1 | 8/2002 | Edwards et al. | |
| 5,861,036 A | 1/1999 | Godin | 6,448,658 B2 | 9/2002 | Takata et al. | |
| 5,863,291 A | 1/1999 | Schaer | 6,451,014 B1 | 9/2002 | Wakikaido et al. | |
| 5,871,483 A | 2/1999 | Jackson et al. | 6,454,790 B1 | 9/2002 | Neuberger et al. | |
| 5,876,340 A | 3/1999 | Tu et al. | 6,464,697 B1 | 10/2002 | Edwards et al. | |
| 5,888,743 A | 3/1999 | Das | 6,468,272 B1 | 10/2002 | Koblish et al. | |
| 5,891,134 A | 4/1999 | Goble et al. | 6,514,246 B1 | 2/2003 | Swanson et al. | |
| 5,895,355 A | 4/1999 | Schaer | 6,514,249 B1 | 2/2003 | Maguire et al. | |
| 5,902,263 A | 5/1999 | Patterson et al. | 6,535,768 B1 | 3/2003 | Baker et al. | |
| 5,904,711 A | 5/1999 | Flom et al. | 6,544,226 B1 | 4/2003 | Gaiser et al. | |
| 5,925,044 A | 7/1999 | Hofmann et al. | 6,547,776 B1 | 4/2003 | Gaiser et al. | |
| 5,938,694 A | 8/1999 | Jaraczewski et al. | 6,547,787 B1 | 4/2003 | Altman et al. | |
| 5,964,755 A | 10/1999 | Edwards | 6,551,302 B1 | 4/2003 | Rosinko et al. | |
| 5,976,129 A | 11/1999 | Desai | 6,551,310 B1 | 4/2003 | Ganz et al. | |
| 5,984,861 A | 11/1999 | Crowley | 6,551,315 B2 | 4/2003 | Kortenbach et al. | |
| 5,997,534 A | 12/1999 | Tu et al. | 6,562,034 B2 | 5/2003 | Edwards et al. | |
| 6,006,755 A | 12/1999 | Edwards | 6,569,162 B2 | 5/2003 | He | |
| 6,010,511 A | 1/2000 | Murphy | 6,572,578 B1 | 6/2003 | Blanchard | |
| 6,012,457 A | 1/2000 | Lesh | 6,572,610 B2 | 6/2003 | Kovalcheck et al. | |
| 6,016,437 A | 1/2000 | Tu et al. | 6,572,639 B1 | 6/2003 | Ingle et al. | |
| 6,023,638 A | 2/2000 | Swanson et al. | 6,575,966 B2 | 6/2003 | Lane et al. | |
| 6,027,499 A | 2/2000 | Johnston et al. | 6,589,238 B2 | 7/2003 | Edwards et al. | |
| 6,033,397 A | 3/2000 | Laufer et al. | 6,610,056 B2 | 8/2003 | Durgin et al. | |
| 6,039,701 A | 3/2000 | Sliwa et al. | 6,613,047 B2 | 9/2003 | Edwards | |
| 6,041,260 A | 3/2000 | Stern et al. | 6,641,581 B2 | 11/2003 | Muzzammel | |
| 6,044,846 A | 4/2000 | Edwards | 6,663,626 B2 | 12/2003 | Truckai et al. | |
| 6,053,172 A | 4/2000 | Hovda et al. | 6,673,070 B2 | 1/2004 | Edwards et al. | |
| 6,053,913 A | 4/2000 | Tu et al. | 6,682,528 B2 | 1/2004 | Frazier et al. | |
| 6,056,744 A | 5/2000 | Edwards | 6,689,130 B2 | 2/2004 | Arail et al. | |
| 6,059,719 A | 5/2000 | Yamamoto et al. | 6,695,764 B2 | 2/2004 | Silverman et al. | |
| 6,068,629 A | 5/2000 | Haissaguerre et al. | 6,712,074 B2 | 3/2004 | Edwards et al. | |
| 6,071,277 A | 6/2000 | Farley et al. | 6,712,814 B2 | 3/2004 | Edwards et al. | |

| | | |
|---|---|---|
| 6,712,815 B2 | 3/2004 | Sampson et al. |
| 6,740,082 B2 | 5/2004 | Shadduck |
| 6,749,607 B2 | 6/2004 | Edwards et al. |
| 6,752,806 B2 | 6/2004 | Durgin et al. |
| 6,800,083 B2 | 10/2004 | Hiblar et al. |
| 6,837,886 B2 | 1/2005 | Collins et al. |
| 6,846,312 B2 | 1/2005 | Edwards et al. |
| 6,860,878 B2 | 3/2005 | Brock |
| 6,866,663 B2 | 3/2005 | Edwards et al. |
| 6,872,206 B2 | 3/2005 | Edwards et al. |
| 6,917,834 B2 | 7/2005 | Koblish et al. |
| 6,918,906 B2 | 7/2005 | Long |
| 6,923,808 B2 | 8/2005 | Taimisto |
| 6,929,642 B2 | 8/2005 | Xiao et al. |
| 6,953,469 B2 | 10/2005 | Ryan |
| 6,964,661 B2 | 11/2005 | Rioux et al. |
| 6,971,395 B2 | 12/2005 | Edwards et al. |
| 6,974,456 B2 | 12/2005 | Edwards et al. |
| 6,994,704 B2 | 2/2006 | Qin et al. |
| 7,004,938 B2 | 2/2006 | Ormsby et al. |
| 7,048,734 B1 | 5/2006 | Fleischman et al. |
| 7,056,320 B2 | 6/2006 | Utley et al. |
| 7,083,620 B2 | 8/2006 | Jahns et al. |
| 7,089,063 B2 | 8/2006 | Lesh et al. |
| 7,122,031 B2 | 10/2006 | Edwards et al. |
| 7,125,407 B2 | 10/2006 | Edwards et al. |
| 7,150,745 B2 | 12/2006 | Stern et al. |
| 7,160,294 B2 | 1/2007 | Croft |
| 7,165,551 B2 | 1/2007 | Edwards |
| 7,167,758 B2 | 1/2007 | Baker et al. |
| 7,179,257 B2 | 2/2007 | West et al. |
| 7,184,827 B1 | 2/2007 | Edwards |
| 7,282,049 B2 | 10/2007 | Orszulak et al. |
| 7,293,563 B2 | 11/2007 | Utley et al. |
| 7,326,207 B2 | 2/2008 | Edwards |
| 7,329,254 B2 | 2/2008 | West et al. |
| 7,416,549 B2 | 8/2008 | Young et al. |
| 7,425,212 B1 | 9/2008 | Danek et al. |
| 7,680,543 B2 | 3/2010 | Azure |
| 7,850,685 B2 | 12/2010 | Kunis et al. |
| 7,970,480 B2 | 6/2011 | Swanson |
| 2001/0041887 A1 | 11/2001 | Crowley |
| 2001/0051802 A1 | 12/2001 | Woloszko et al. |
| 2002/0035324 A1 | 3/2002 | Sirimanne et al. |
| 2002/0087151 A1 | 7/2002 | Mody et al. |
| 2002/0177847 A1 | 11/2002 | Long |
| 2002/0183739 A1 | 12/2002 | Long |
| 2003/0069572 A1 | 4/2003 | Wellman et al. |
| 2003/0093117 A1 | 5/2003 | Saadat |
| 2003/0109837 A1 | 6/2003 | McBride-Sakal |
| 2003/0153905 A1 | 8/2003 | Edwards et al. |
| 2003/0158550 A1* | 8/2003 | Ganz et al. .................. 606/41 |
| 2003/0181900 A1 | 9/2003 | Long |
| 2003/0181905 A1 | 9/2003 | Long |
| 2003/0191512 A1 | 10/2003 | Laufer et al. |
| 2003/0216727 A1 | 11/2003 | Long |
| 2004/0087936 A1 | 5/2004 | Stern et al. |
| 2004/0092892 A1 | 5/2004 | Kagan et al. |
| 2004/0122452 A1 | 6/2004 | Deem et al. |
| 2004/0147916 A1 | 7/2004 | Baker |
| 2004/0153120 A1 | 8/2004 | Seifert et al. |
| 2004/0172016 A1 | 9/2004 | Bek et al. |
| 2004/0204708 A1 | 10/2004 | Edwards et al. |
| 2004/0215180 A1 | 10/2004 | Starkebaum et al. |
| 2004/0215235 A1 | 10/2004 | Jackson et al. |
| 2004/0215296 A1 | 10/2004 | Ganz et al. |
| 2004/0236316 A1 | 11/2004 | Danitz et al. |
| 2004/0243124 A1 | 12/2004 | Im et al. |
| 2005/0010162 A1 | 1/2005 | Utley et al. |
| 2005/0033271 A1 | 2/2005 | Qin et al. |
| 2005/0070978 A1 | 3/2005 | Bek et al. |
| 2005/0090817 A1 | 4/2005 | Phan |
| 2005/0096713 A1 | 5/2005 | Starkebaum et al. |
| 2005/0107829 A1 | 5/2005 | Edwards et al. |
| 2005/0143727 A1 | 6/2005 | Koblish et al. |
| 2005/0149013 A1 | 7/2005 | Lee |
| 2005/0154386 A1 | 7/2005 | West et al. |
| 2005/0159743 A1 | 7/2005 | Edwards et al. |
| 2005/0187546 A1 | 8/2005 | Bek et al. |
| 2005/0215983 A1 | 9/2005 | Brock |
| 2005/0245926 A1 | 11/2005 | Edwards et al. |
| 2005/0288664 A1 | 12/2005 | Ford et al. |
| 2006/0009758 A1 | 1/2006 | Edwards et al. |
| 2006/0015162 A1 | 1/2006 | Edwards et al. |
| 2006/0041256 A1 | 2/2006 | Edwards et al. |
| 2006/0069303 A1 | 3/2006 | Couvillon |
| 2006/0086363 A1 | 4/2006 | Qin et al. |
| 2006/0095032 A1* | 5/2006 | Jackson et al. .................. 606/41 |
| 2006/0247614 A1 | 11/2006 | Sampson et al. |
| 2006/0259028 A1 | 11/2006 | Utley et al. |
| 2006/0259029 A1 | 11/2006 | Utley et al. |
| 2006/0259030 A1 | 11/2006 | Utley et al. |
| 2006/0282071 A1 | 12/2006 | Utley et al. |
| 2007/0021743 A1 | 1/2007 | Rioux et al. |
| 2007/0066973 A1 | 3/2007 | Stern et al. |
| 2007/0100333 A1 | 5/2007 | Jackson et al. |
| 2007/0118104 A1 | 5/2007 | Wallace et al. |
| 2007/0118106 A1 | 5/2007 | Utley et al. |
| 2007/0118159 A1 | 5/2007 | Deem et al. |
| 2007/0135809 A1 | 6/2007 | Utley et al. |
| 2007/0142831 A1 | 6/2007 | Shadduck |
| 2007/0167963 A1 | 7/2007 | Deem et al. |
| 2007/0219570 A1 | 9/2007 | Deem et al. |
| 2007/0255296 A1 | 11/2007 | Sauer |
| 2007/0287994 A1 | 12/2007 | Patel |
| 2007/0288001 A1 | 12/2007 | Patel |
| 2008/0097427 A1 | 4/2008 | Stern et al. |
| 2008/0275445 A1 | 11/2008 | Kelly et al. |
| 2008/0319350 A1 | 12/2008 | Wallace et al. |
| 2009/0012512 A1 | 1/2009 | Utley et al. |
| 2009/0012518 A1 | 1/2009 | Utley et al. |
| 2009/0299355 A1 | 12/2009 | Bencini et al. |
| 2010/0063495 A1 | 3/2010 | Utley et al. |

FOREIGN PATENT DOCUMENTS

| | | |
|---|---|---|
| EP | 0105677 | 4/1984 |
| EP | 0115420 | 8/1984 |
| EP | 0139607 | 5/1985 |
| EP | 0251745 | 1/1988 |
| EP | 0521595 A2 | 1/1993 |
| EP | 0608609 | 8/1994 |
| EP | 1323382 A1 | 7/2003 |
| EP | 0754075 B1 | 3/2006 |
| EP | 1634542 B1 | 3/2006 |
| EP | 1562506 B1 | 5/2009 |
| JP | 8-506738 | 7/1996 |
| JP | 2005503181 | 2/2005 |
| WO | WO 91/01773 | 2/1991 |
| WO | WO 91/03207 A1 | 3/1991 |
| WO | WO 92/10142 | 6/1992 |
| WO | WO 93/08755 | 5/1993 |
| WO | WO 94/07446 A1 | 4/1994 |
| WO | WO 94/10925 | 5/1994 |
| WO | WO 94/21165 | 9/1994 |
| WO | WO 94/22366 | 10/1994 |
| WO | WO 94/26178 | 11/1994 |
| WO | WO 95/18575 | 7/1995 |
| WO | WO 95/19142 | 7/1995 |
| WO | WO 95/25472 | 9/1995 |
| WO | WO 96/00042 | 1/1996 |
| WO | WO 96/16606 | 6/1996 |
| WO | WO 96/29946 | 10/1996 |
| WO | WO 97/04702 | 2/1997 |
| WO | WO 97/06857 | 2/1997 |
| WO | WO 97/32532 | 9/1997 |
| WO | WO 97/43971 | 11/1997 |
| WO | WO 98/12999 A2 | 4/1998 |
| WO | WO 98/14238 A1 | 4/1998 |
| WO | WO 98/18393 A1 | 5/1998 |
| WO | WO 99/03413 | 1/1999 |
| WO | WO 99/35987 | 7/1999 |
| WO | WO 99/42046 | 8/1999 |
| WO | WO 99/55245 | 11/1999 |
| WO | WO 00/01313 | 1/2000 |
| WO | WO 00/59393 | 10/2000 |
| WO | WO 00/62699 A2 | 10/2000 |
| WO | WO 00/66017 A1 | 11/2000 |
| WO | WO 00/66021 | 11/2000 |

| | | |
|---|---|---|
| WO | WO 00/66052 A1 | 11/2000 |
| WO | WO 00/069376 A1 | 11/2000 |
| WO | WO 01/22897 A1 | 4/2001 |
| WO | WO 01/35846 | 5/2001 |
| WO | WO 01/045550 A2 | 6/2001 |
| WO | WO 01/089440 | 11/2001 |
| WO | WO 02/096327 A2 | 12/2002 |
| WO | WO 03/070091 A1 | 8/2003 |
| WO | WO 2004/043280 A1 | 5/2004 |
| WO | WO 2007/001981 A2 | 1/2007 |
| WO | WO 2007/061984 A2 | 5/2007 |

OTHER PUBLICATIONS

Dallamagne et al; Laparoscopic Nissen Fundoplication: Preliminary. Surgical Laparoscopy and Endoscopy. 1991; 1(3):138-143.

Hinder et al; The Technique of Laparoscopic Nissen Fundoplication. Surgical Laparoscopy and Endoscopy. 1992; 2(3):265-272.

Kaneko et al; Physiological Laryngeal Pacemaker. Trans Am Soc. Artif Intern Organs. 1985; XXXI:293-296.

Karlstrom et al; Ectopic Jejunal Pacemakers and Enterogastric Reflux Roux Gastrectomy: Effect of Intestinal Pacing. Surgery. 1989; 106(3):486-495.

Kelly, K.A. et al; Duodenal-Gastric Reflux and Slowed Gastric Emptying by Electrical Pacing of the Canine Duodenal Pacesetter Potential. Gastroenterology. 1977; 72(3):429-433.

Mugica, et al. Direct Diaphragm Stimulation. PACE. 1987; 10:252-256.

Mugica, et al., Preliminary Test of a Muscular Diaphragm Pacing System on Human Patients. Neurostimulation: An Overview, chapter 21. 1985; 263-279.

Reynolds, J.C. Influence of Pathophysiology, Severity, and Cost on the Medical Management of Gastroesophageal Reflux Disease. Am J. Health-Syst Phar. 1996; 53(22sul3):S5-S12.

Rice et al; Endoscopic Paranasal Sinus Surgery. Chapter 5, Functional Endoscopic Paranasal Sinus Surgery, The Technique of Messerklinger. Raven Press. 1988; 75-102.

Rice et al; Endoscopic Paranasal Sinus Surgery. Chapter 6, Total Endoscopic Sphenoethmoidectomy. The Technique of Wigand. Raven Press. 1988; 103-125.

Salameh et al; An Animal Model Study to Clarify and Investigate Endoscopic Tissue Coagulation by Using a New Monopolar Device. Gastrointestinal Endoscopy; 2004; 59 (1): 107-112.

Urshel, J.D. Complications of Antireflux Surgery. Am J. Surg. 1993; 166 (1):68-70.

Wallace et al; U.S. Appl. No. 11/830,251 entitled "Cleaning Devices and Methods," filed Jul. 30, 2007.

Utley et al; U.S. Appl. No. 11/830,291 entitled "Cleaning Device and Methods," filed Jul. 30, 2007.

Ganz et al; U.S. Appl. No. 12/259,136 entitled "System and method of treating abnormal tissue in the human esophagus," filed Oct. 27, 2008.

Utley, David S.; U.S. Appl. No. 12/270,373 entitled "System and method for ablational treatment of uterine cervical neoplasma," filed Nov. 13, 2008.

Shadduck, John H.; U.S. Appl. No. 12/751,803 entitled "Surgical instruments and techniques for treating gastro-esophageal reflux disease," filed Mar. 31, 2010.

Shadduck, John; U.S. Appl. No. 12/368,943 entitled "Surgical instruments and techniques for treating gastro-esophageal reflux disease," filed Feb. 10, 2009.

Wallace et al.; U.S. Appl. No. 12/404,159 entitled "Auto-aligning ablating device and method of use," filed Mar. 13, 2009.

Wallace et al.; U.S. Appl. No. 13/051,738 entitled "Selectively expandable operative element support structure and methods of use," filed Mar. 18, 2011.

Jackson et al.; U.S. Appl. No. 12/787,324 entitled "Methods and systems for determining physiologic characteristics for treatment of the esophagus," filed May 25, 2010.

Jackson, Jerome; U.S. Appl. No. 13/181,484 entitled "Methods and systems for treatment of tissue in a body lumen," filed Jul. 12, 2011.

Utley et al.; U.S. Appl. No. 13/181,490 entitled "Precision ablating method," filed Jul. 12, 2011.

Jackson et al.; U.S. Appl. No. 13/189,793 entitled "Methods and Systems for Determining Physiologic Characteristics for Treatment of the Esophagus," filed Jul. 25, 2011.

* cited by examiner

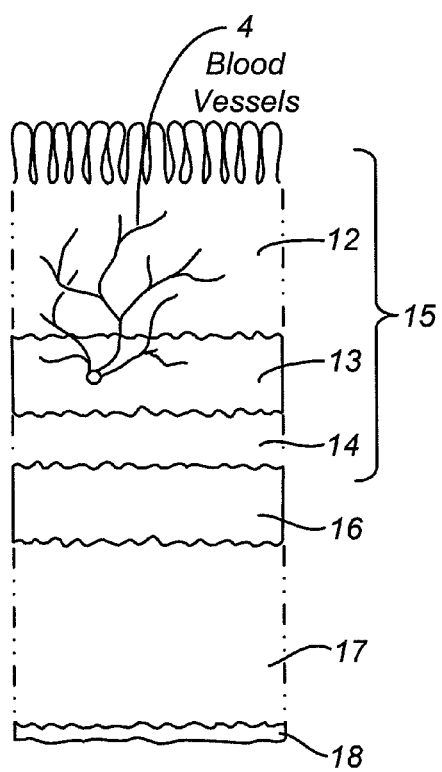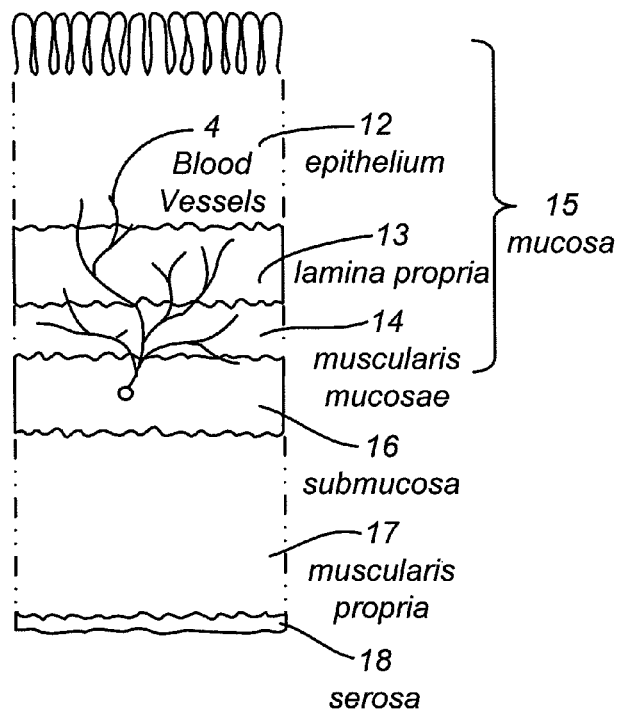
FIG. 1A  FIG. 1B

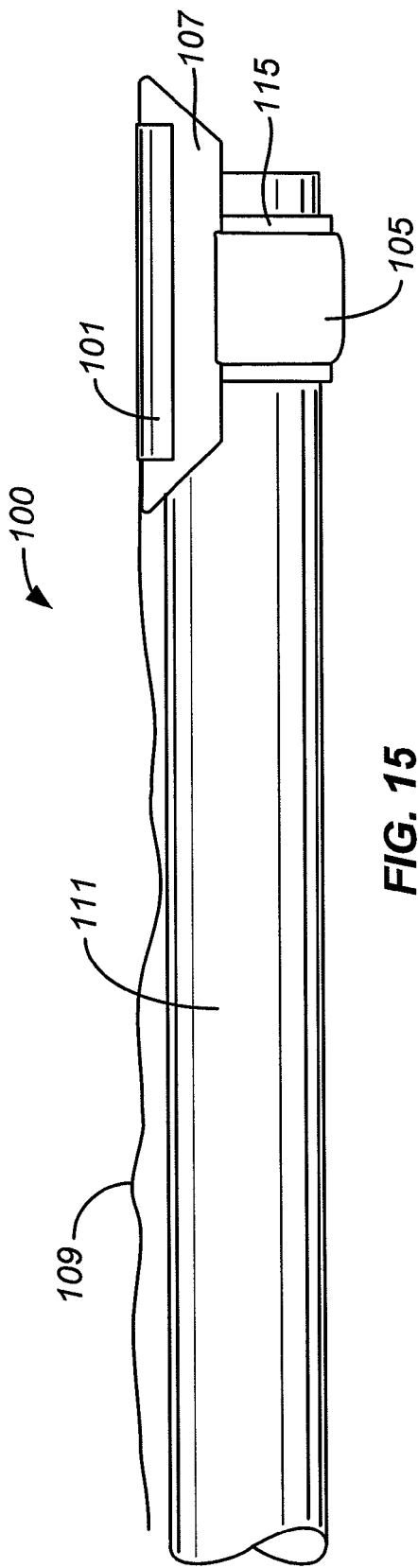
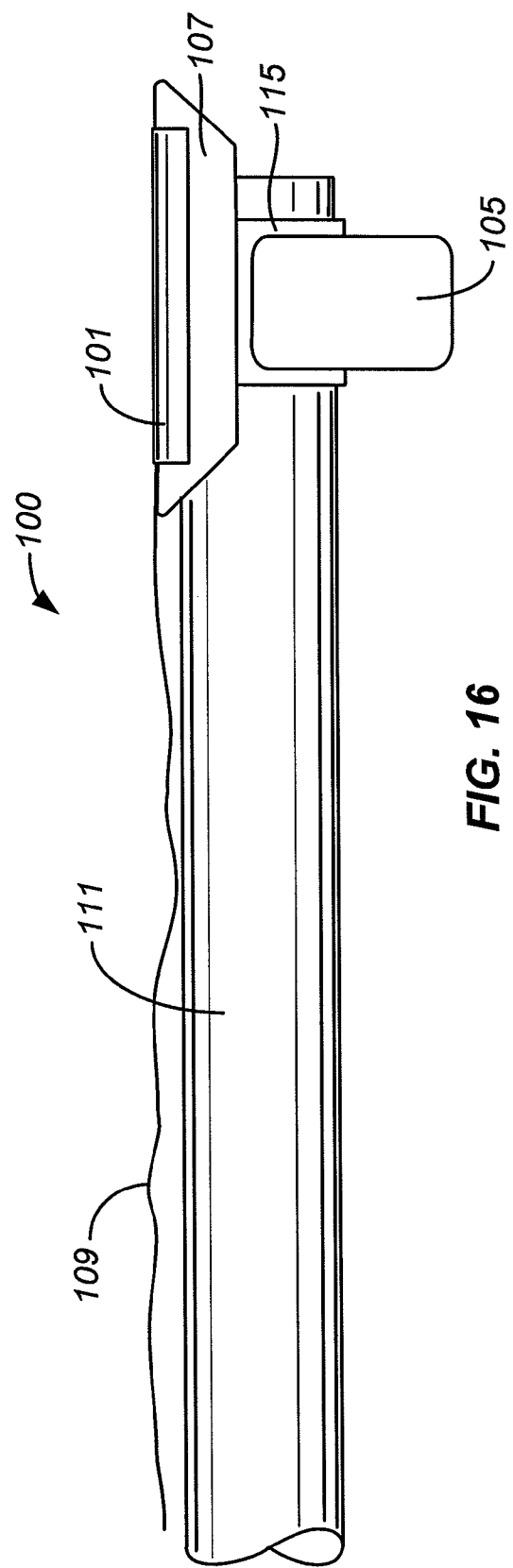
FIG. 15
FIG. 16

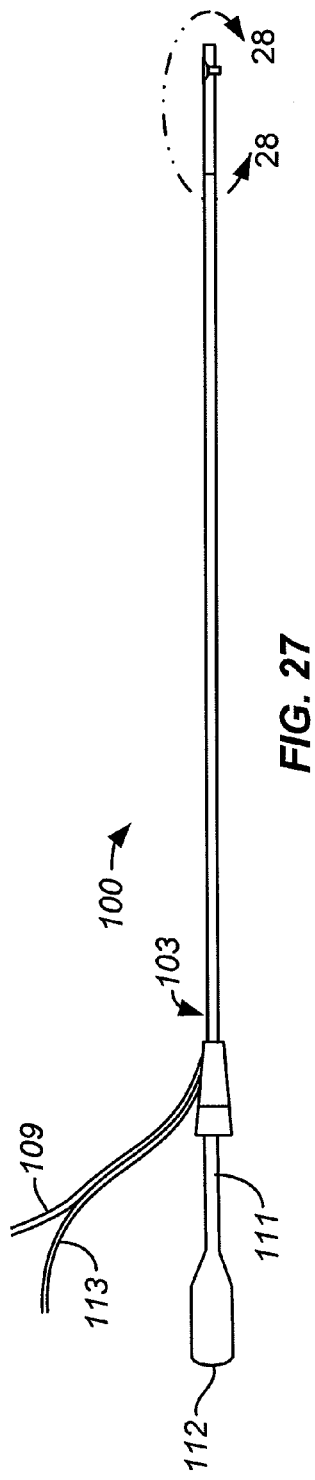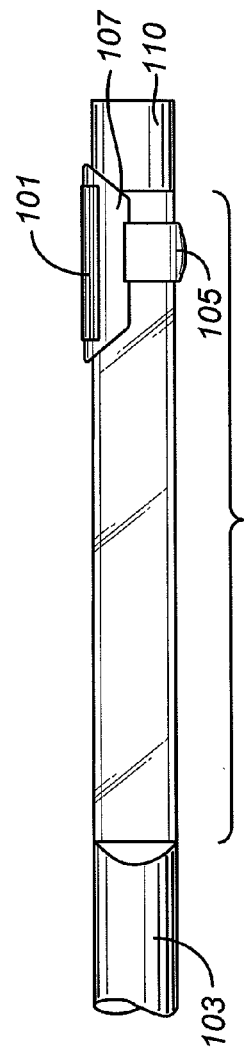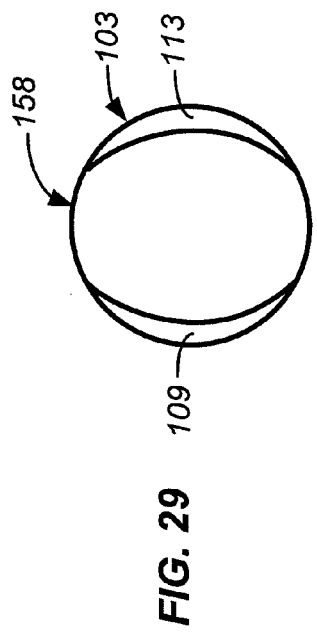
FIG. 27
FIG. 28
FIG. 29

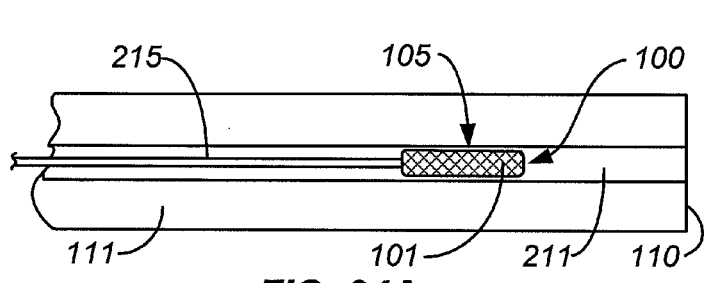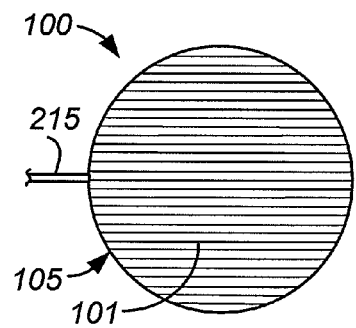
FIG. 34A
FIG. 34B
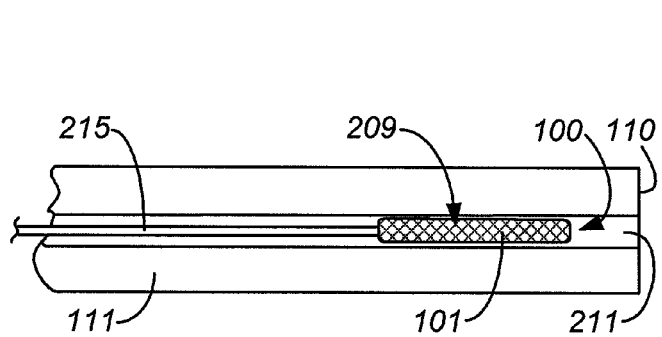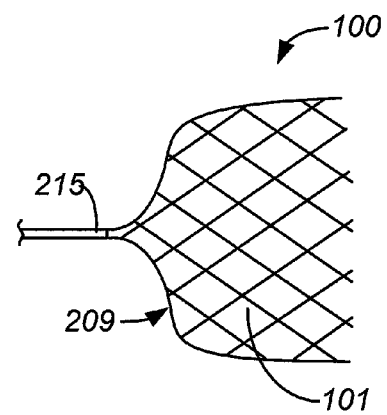
FIG. 35A
FIG. 35B
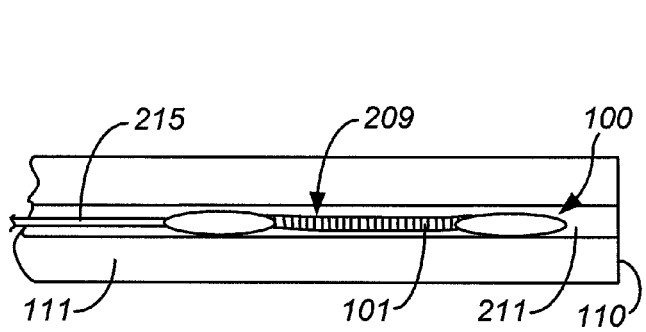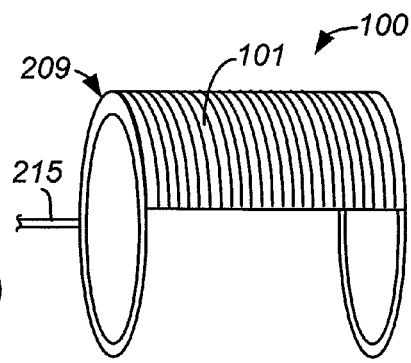
FIG. 36A
FIG. 36B

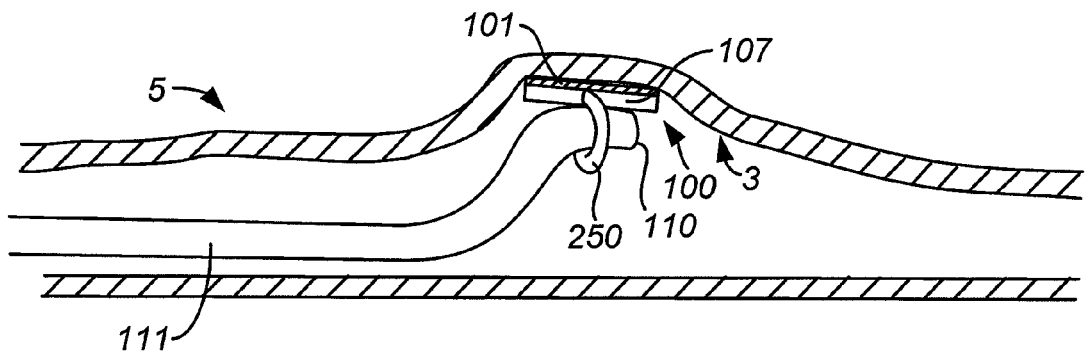
FIG. 43
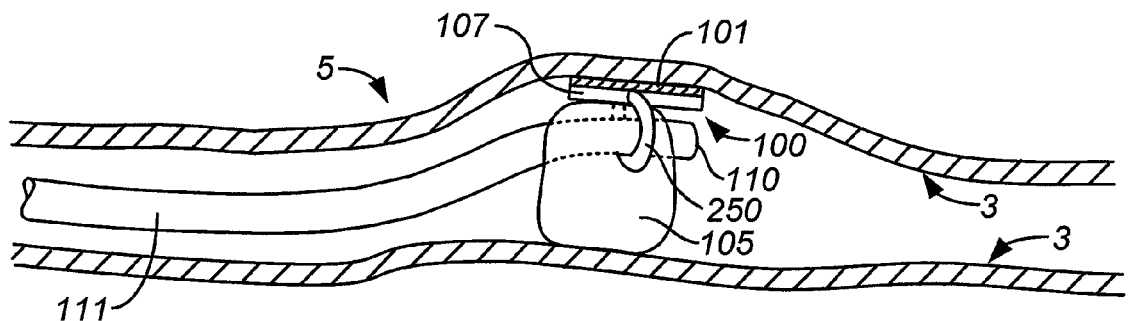
FIG. 44
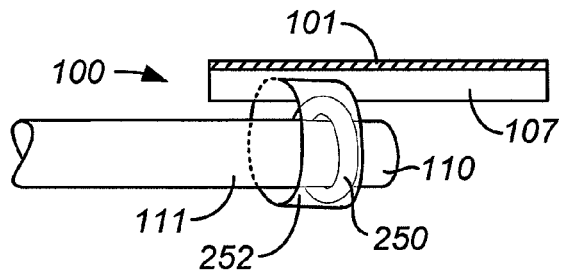
FIG. 45A
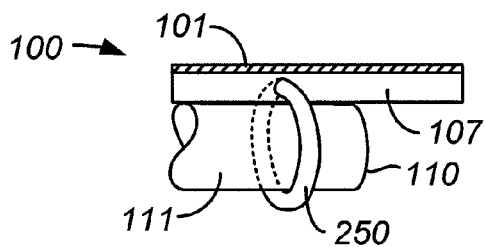 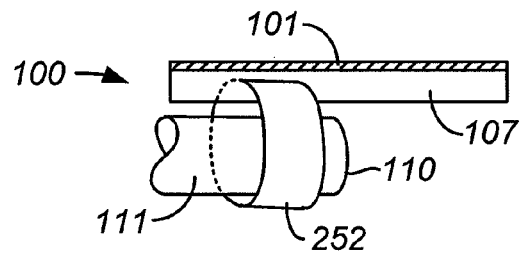
FIG. 45B     FIG. 45C

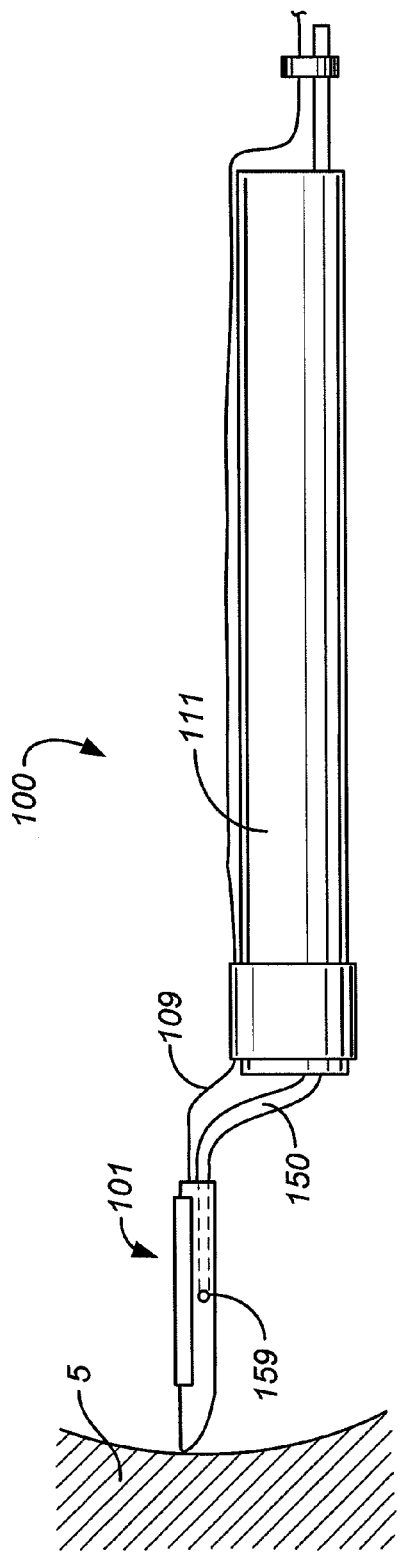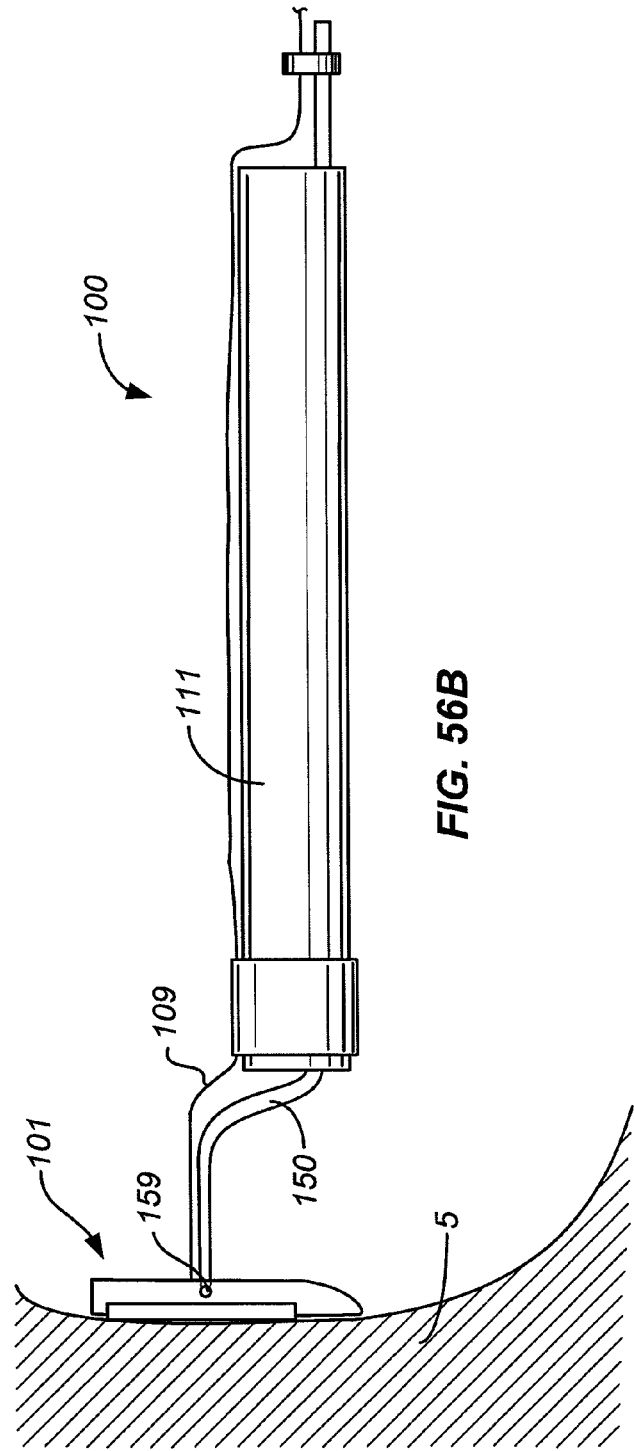

ABLATION IN THE GASTROINTESTINAL TRACT TO ACHIEVE HEMOSTASIS AND ERADICATE LESIONS WITH A PROPENSITY FOR BLEEDING

CROSS REFERENCE TO RELATED APPLICATIONS

This application claims priority to U.S. Provisional Application No. 60/958,566, entitled "Non-Barrett's Mucosal Ablation Disease Targets" by Utley, Wallace and Gerberding, as filed on Jul. 6, 2007.

This application incorporates in entirety commonly assigned U.S. patent application Ser. No. 10/370,645 entitled "Method of Treating Abnormal Tissue in the Human Esophagus", filed on Feb. 19, 2003, and published as US 2003/0158550 on Aug. 21, 2003, and U.S. patent application Ser. No. 11/286,444 entitled "Precision Ablating Method", filed on Nov. 23, 2005, and published as US 2007/0118106 on May 24, 2007. Further, each of the following commonly assigned United States Patent Applications are incorporated herein by reference in its entirety: patent application Ser. No. 10/291,862 titled "Systems and Methods for Treating Obesity and Other Gastrointestinal Conditions," patent application Ser. No. 10/370,645 titled "Method of Treating Abnormal Tissue In The Human Esophagus," patent application Ser. No. 11/286,257 titled "Precision Ablating Device," patent application Ser. No. 11/275,244 titled "Auto-Aligning Ablating Device and Method of Use," patent application Ser. No. 11/286,444 titled "Precision Ablating Device," patent application Ser. No. 11/420,712 titled "System for Tissue Ablation," patent application Ser. No. 11/420,714 titled "Method for Cryogenic Tissue Ablation," patent application Ser. No. 11/420,719 titled "Method for Vacuum-Assisted Tissue Ablation," patent application Ser. No. 11/420,722 titled "Method for Tissue Ablation," patent application Ser. No. 11/469,816 titled "Surgical Instruments and Techniques for Treating Gastro-Esophageal Reflux Disease." This application further incorporates in entirety U.S. patent application Ser. No. 12/114,628 of Kelly et al. entitled "Method and Apparatus for Gastrointestinal Tract Ablation for Treatment of Obesity", as filed on filed May 2, 2008 and U.S. patent application Ser. No. 12/143,404, of Wallace et al., entitled "Electrical Means to Normalize Ablational Energy Transmission to a Luminal Tissue Surface of Varying Size", as filed on Jun. 20, 2008.

INCORPORATION BY REFERENCE

All publications, patents and patent applications mentioned in this specification are herein incorporated by reference to the same extent as if each individual publication, patent or patent application was specifically and individually indicated to be incorporated by reference.

FIELD OF THE INVENTION

The present invention relates to endoscopic therapy devices and methods, such as devices and methods to treat areas of the digestive tract in patients with bleeding conditions of the digestive tract, in order to control bleeding (achieve hemostasis) and/or eradicate lesions with a propensity for bleeding.

BACKGROUND OF THE INVENTION

Bleeding may occur into the digestive tract lumen from blood vessels contained in the digestive tract wall. Such bleeding is abnormal and may be associated with certain disease states and anatomical abnormalities. When bleeding occurs, it can be an acute emergency, with vomiting of blood or passage of blood from the rectum. In these cases, urgent endoscopic or surgical intervention is often necessary, along with blood transfusion, to avoid patient morbidity and mortality. Examples include a bleeding varix within the esophagus related to portal hypertension, an exposed bleeding vessel within a gastric or duodenal ulcer, or an arteriovenous malformation (collection of disorganized blood vessels) within the bowel that has ruptured.

Other bleeding lesions may present with chronic, less severe bleeding that results in chronic anemia and the need for serial endoscopic therapeutic interventions to cauterize visible abnormalities. Such cases often require chronic transfusion therapy, as the endoscopic interventions are not ideal to permanently halt bleeding. Examples include gastric antral vascular ectasia (GAVE), which is also known as watermelon stomach, for the appearance of its characteristic gastric lesions, radiation induced proctopathy and colopathy, portal hypertensive gastropathy (PHG), angiodysplasia, small arteriovenous malformations (AVM), and small bleeding ulcers. The common finding in many of these more chronic abnormalities is the presence of blood vessels in the digestive tract wall, specifically the mucosal and submucosal layers, that are larger than normal, more fragile than normal, more superficial than normal, tangled, disorganized, and/or exposed to the lumen of the digestive tract and therefore more traumatized than normal by passage of food or stool. Due to these combinations of features, these vessels tend to bleed into the lumen of the digestive tract on a chronic basis, thereby requiring chronic management.

Acute bleeding episodes of a magnitude where the patient is vomiting blood or passing blood from the rectum and is having cardiovascular effects are usually managed urgently with endoscopic or surgical therapy and blood transfusion. Typically, these events are associated with a large blood vessel that has ruptured and is bleeding profusely into the lumen. These lesions are visualized with an endoscope and may be injected with adrenalin to slow the bleeding, then cauterized with a small probe which is touched directly onto the vessel or may be cauterized with an electrified stream of argon gas. These probes deliver radiofrequency energy that rapidly heats the targeted focal vessel or tissue, and the blood vessels shrink and stop bleeding. Surgery is reserved for those patients with life-threatening bleeding that is not amenable to endoscopic therapy.

Chronic bleeding episodes, while causing long-term disability and the need for repeat therapy and transfusion, do not typically require urgent, life-saving intervention. Rather, these lesions are typically sought after with endoscopic examination when a patient presents with anemia of unknown cause. As described above, these lesions are identifiable and targetable with endoscopy. Cauterization is the standard therapy, in hopes of permanently eliminating the risk for bleeding. Unfortunately, in many cases, current techniques of cauterization fail to permanently eradicate these lesions, and bleeding returns. Factors contributing to unsatisfactory results with currently available cautery methods include the fact that lesions such as GAVE, radiation induced protopathy and colopathy, portal hypertensive gastropathy, and angiodysplasias tend to manifest as large, wide-spread lesions that are not amenable to a cautery technique which uses a small probe to press against the lesion. Even arteriovenous malformations tend to have high flow and larger surface areas, making them difficult to treat with small probes. Another likely reason for problematic and inconsistent results with conventional cautery methods relates to the presence of blood in the vasculature tissue at the time of cautery. Systems and methods, particularly non-surgical approaches or improvements on conventional cautery techniques would be welcomed in the field of treating sites of acute and chronic bleeding in the gastrointestinal tract.

SUMMARY OF THE INVENTION

To address these and other needs, the present invention provides various embodiments of an endoscopic device and method to provide a more permanent resolution of primarily chronic bleeding occurring in the digestive tract and a more permanent eradication of the lesions that lead to such bleeding, by way of providing a larger ablation surface, compressing the blood vessels prior to delivery cauterization energy, and controlling the depth of ablation to include the tissue layers containing the bleeding vessels. To this end, the device includes an endoscopic catheter that is either balloon-based, mounted on the end of the endoscope, or passes through a working channel or accessory channel of an endoscope. The device has an electrical array on at least one surface to deliver radiofrequency energy or other energy source to the targeted tissue in a manner so that the depth of ablation is controlled via parameters such as energy density, electrode pattern, power density, number of applications, and pressure exerted on the tissue. The catheter is supplied with ablation energy by an energy generator, connected to the catheter with a cable.

The method includes using the devices described, along with an existing endoscope for visualization, to visualize the area of the digestive tract that contains the lesion that is actively bleeding or is causing chronic recurrent bleeding. The device is positioned to come into contact with the lesion and is then deployed according to the device embodiment so that the blood vessels are compressed. Ablative energy is then delivered to the device and into the lesion, causing hemostasis and eradication of the lesion.

Compression prior to delivery of coagulation energy halts or reduces blood flow within the targeted vessels. When energy is then delivered, coaptive coagulation occurs more readily, meaning that the vessel walls are sealed to themselves. If blood flow was occurring during coagulation, there would be a higher failure rate due to the blood holding the vessels open and the heat sink effect that the blood flow provides.

Treatment parameters may be such that a uniform level of ablation is achieved in all or part of the targeted lesion. For example, for superficial lesions, the depth of ablation desired may be the mucosa or a portion of the mucosa. For deeper lesions, the depth of ablation may be the deeper mucosa and all or part of the submucosa. Depth control and uniformity of ablation effect are achieved via features of the device and treatment parameters, including electrode pattern, pressure against the targeted lesion, energy density, power density, and number of applications.

Embodiments of the invention include a system and methods of implementing the system toward a method of treating an area of bleeding in a gastrointestinal tract. The therapeutic method includes identifying the area of bleeding; positioning a therapy device in the gastrointestinal tract adjacent to a target site within the area of bleeding; pressuring the bleeding area to diminish the amount of blood within blood vessels in the bleeding area; and applying non-surgical hemostatic therapy to a target site in the area while continuing to pressure the area. In some embodiments of this method the identifying step is performed endoscopically. And in some embodiments, the identifying step, the positioning step, the pressuring step, and the performing step are conducted during a single endoscopic procedure. In other embodiments, the method may further include inserting an instrument having a hemostatic therapy device mounted thereon into the gastrointestinal tract before the identifying step, and removing the instrument after the applying step.

In some embodiments of the method, applying the non-surgical hemostatic therapy on the target site includes applying energy, such as radiofrequency energy, to the target site. In various embodiments, applying energy to the target site includes controlling the delivery of energy across the tissue surface in the target site. In some embodiments, applying energy to the target site includes controlling the depth of delivery of energy into tissue layers in the target site. In some embodiments, applying energy to the target site may include applying energy more than once, and in some embodiments, applying energy to the target site includes applying energy to more than one target site in the area of bleeding.

In some embodiments of the method, applying non-surgical hemostatic therapy on the target site includes applying cryogenic treatment to the target site. In some embodiments of applying cryogenic treatment, such treatment includes spraying a cryogenic fluid on the target site, and in other embodiments, applying cryogenic treatment includes drawing heat from the target area into a cryogenic fluid contained in the device In some embodiments of the method, the positioning step further includes moving an ablation structure of the device so as to make therapeutic contact with a target site within the area of bleeding. And in some of these embodiments, moving the ablation structure may include any of inflating a balloon member, expanding a deflection member, moving a deflection member, or expanding an expandable member.

Pressuring the bleeding area, which underlies the coaptive aspect of the ablation therapy, includes a applying pressure to the target area at about 1 psig to about 15 psig, in various embodiments, the pressure applied is in the range of about 3 psig to about 7 psig, and in particular embodiments, the applied pressure is about 4 psig.

In another aspect of the invention, a method is directed toward ablationally-treating a target site within an area of bleeding in a gastrointestinal tract. Such a method may include pressuring the bleeding area to diminish the amount of blood within blood vessels in the bleeding area, and delivering radiofrequency energy to a tissue surface within the target area, the target area being a contiguous radial portion of the gastrointestinal tract, and controlling the delivery of radiofrequency energy across the tissue surface within the target area and into a depth of tissue within the target area. The area of bleeding may be any of a site of acute bleeding, chronic bleeding, or any site identified as having a propensity to bleed. More specifically, a site of acute bleeding may include any of a bleeding varix within the esophagus, an exposed bleeding vessel within a gastric or duodenal ulcer, or an arteriovenous malformation within the bowel. And a site of chronic bleeding may include any of a site of gastric antral vascular ectasia (GAVE), radiation induced proctopathy or colopathy, portal hypertensive gastropathy (PHG), angiodysplasia, small arteriovenous malformations (AVM), or small bleeding ulcers.

In some embodiments of the method, controlling the delivery of radiofrequency energy across the surface and into a depth of tissue within the target area includes delivering sufficient radiofrequency energy to achieve ablation in one portion of the tissue target area and delivering insufficient radiofrequency energy to another portion of the surface to achieve ablation. In some embodiments of the method, controlling the delivery of radiofrequency energy into depth of the tissue includes controlling the delivery of radiofrequency energy in from the tissue surface such that sufficient energy to achieve ablation is delivered to one or more tissue layers near the surface and insufficient energy is delivered to other deeper layers to achieve ablation.

In some embodiments of the method, controlling the delivery of radiofrequency energy across the target area surface includes configuring the electrode pattern such that some spacing between electrodes is sufficiently close to allow conveyance of sufficient energy to ablate and other spacing between electrodes is insufficiently close to allow conveyance of sufficient energy to ablate. In other embodiments of the method, controlling the delivery of radiofrequency energy across the target area surface includes operating the electrode pattern such that the energy delivered between some electrodes is sufficient to ablate and energy sufficient to ablate is not delivered between some electrodes.

In some embodiments of the method, controlling the delivery of energy commencing at the mucosal surface and emanating into the organ wall includes ablating some portion of the blood vessels within the epithelial layer. In various embodiments of the method, controlling the delivery of energy commencing at the mucosal surface and emanating progressively deeper into layers of the organ wall includes ablating some portion of the blood vessels within the epithelial layer and the lamina propria. In still other embodiments, some portion of blood vessels may be ablated in epithelial layer, the lamina propria, and the muscularis mucosae, or in the epithelial layer, the lamina propria, the muscularis mucosae, and the submucosal, or in the epithelial layer, the lamina propria, the muscularis mucosae, the submucosa, and the muscularis propria. Further, in various embodiments, controlling the delivery of radiofrequency energy across the tissue surface within the target area and into the depth of tissue within the target area includes achieving of a partial ablation in tissue layers of the gastrointestinal tract.

In some embodiments of the method, delivering radiofrequency energy is by way of an electrode pattern configured circumferentially through 360 degrees around the ablation structure. In other embodiments, transmitting energy from the ablation structure includes transmitting energy asymmetrically through the 360 degree circumference such that ablation is focused within an arc of less that 360 degrees. In other embodiment, delivering radiofrequency energy is by way of an electrode pattern configured circumferentially through an arc of less than 360 degrees around the ablation structure. Regardless of the ablation pattern, in various embodiments, the delivering energy step may be performed more than once, and at more than one site.

In some embodiments, the method further includes evaluating the target area at a point in time after the delivering energy step to determine the status of the area. In various embodiments, the evaluating step occurs in close time proximity after the delivery of energy, to evaluate the immediate post-treatment status of the site. In other embodiments, the evaluating step may occur at least one day after the delivery of energy.

In various embodiments, the method further includes deriving energy for transmitting from an energy source that is controlled by a control system. In some of these embodiments, the energy source is a generator. An in some embodiments operated by a control system, the method includes feedback controlling the energy transmission so as to provide any of a specific power, power density, energy, energy density, circuit impedance, or tissue temperature.

Some embodiments of the method of ablationally treating an area of bleeding may further include advancing an ablation structure into the alimentary canal, the non-penetrating electrode pattern on the structure, the structure supported on an instrument, positioning the ablation structure adjacent to the target area, and moving the ablation structure toward the surface of the target area to make therapeutic contact on the target area prior to delivering energy. The moving step may variously include any of inflating a balloon member, expanding a deflection member, moving a deflection member, or expanding an expandable member.

In some embodiments of the method of ablationally treating an area of bleeding further include a position-locking step following the moving step; and example of which includes developing suction between the structure and the ablation site. The method, prior to the evaluating step, may further include evaluating the target area prior to the positioning step to determine the status of the target area. In other variations of the method, when multiple target areas are being treated, the method may include the positioning, moving, and transmitting energy steps to a first target area, and then further include the positioning, moving, and transmitting energy steps to another target area without removing the ablation structure from the patient.

Some embodiments of the invention include ablation system for treating a target site within an area of bleeding in a gastrointestinal tract, such system including an electrode pattern including a plurality of electrodes, a longitudinal support member supporting the electrode pattern, a generator coupled to the plurality of electrodes, and a computer controller in communication with the generator, the controller having programming to direct the generator to deliver energy to the plurality of electrodes, the programming including the ability to direct delivery of energy to a subset of the electrodes, the electrodes of the pattern configured such that, when receiving energy from the generator and in therapeutic contact with a tissue target area, delivery of energy across the surface of the target area and into a depth of tissue layers from the tissue surface is controlled.

Various embodiments of the system may be directed toward treating an area of bleeding that includes any of a bleeding varix within the esophagus, an exposed bleeding vessel within a gastric or duodenal ulcer, or an arteriovenous malformation within the bowel. Other embodiments may be directed toward treating an area of area of bleeding includes any of a site of gastric antral vascular ectasia (GAVE), radiation induced proctopathy or colopathy, portal hypertensive gastropathy (PHG), angiodysplasia, small arteriovenous malformations (AVM), or small bleeding ulcers.

The electrode pattern of some embodiments of ablation system for treating a target site within an area of bleeding in a gastrointestinal tract has a longitudinal axis that forms a fully circumferential surface orthogonal to its longitudinal axis as aligned with a delivery instrument, the pattern sized for contacting tissue in a target area within the gastrointestinal tract. In other embodiments, the electrode pattern forms a partially circumferential surface orthogonal to its longitudinal axis, the pattern sized for contacting tissue in a target area within the gastroinstestinal tract. In various of these latter embodiments, the electrode pattern may form an arc of about 90 degrees or about 180 degrees.

In some embodiments of the ablation system, the electrode elements are distributed into a pattern such that when the programming directs the generator to deliver energy to all the electrodes, the electrode pattern, when therapeutically contacted to a target tissue area, ablates a portion of tissue within the target area and does not ablate another portion of tissue within the target area. In other embodiments of the ablation system, the programming directs the generator to deliver energy to a subset of electrode elements that form a pattern which, when therapeutically contacted to a target tissue area, ablates a portion of tissue within the target area and does not ablate another portion of tissue within the target area. In various embodiments of the system, regardless of whether the electrode pattern is fully activated to deliver a pattern of fractional ablation, or the pattern is partially activated to deliver a pattern of fractional ablation, the system renders tissue that is ablated at least partially dysfunctional, and another portion that is substantially not ablated and accordingly retains its functionality.

Some embodiments of the invention include an ablation system for vascular tissue at a target area in a gastrointestinal tract of a patient that includes an ablation structure supported by an instrument, a non-penetrating electrode pattern on the ablation support structure, the electrode pattern configured to control the delivery of energy to a target tissue such that a portion of the surface of the target area receives sufficient radiofrequency energy to achieve ablation and another portion of the surface of the target receives insufficient energy to achieve ablation, and means supported by the instrument by which to bring the ablation structure to make therapeutic contact with tissue at the target area.

BRIEF DESCRIPTION OF THE DRAWINGS

FIGS. 1A and 1B provide views of a schematic representation of a cross section of the wall of a portion of the gastrointestinal tract with bleeding blood vessels. FIG. 1A shows a portion of a blood vessel, an arteriole or venuole, with branching capillaries that are located primarily in the lamina propria and the epithelium. FIG. 1B shows a portion of a blood vessel, an arteriole or venuole, with branching capillaries that are located primarily in the submucosa and the lamina propria.

FIG. 2A shows an arteriovenous malformation (AVM). FIG. 2B provides a schematic view of telangiectases, with a grossly dilated capillary. FIG. 2C provides an endoscopic view of the stomach, looking toward the pylorus of a patient with watermelon stomach lesions characteristic of GAVE.

FIG. 15 is a view of the ablation device of the invention in an unexpanded configuration.

FIG. 16 is a view of the ablation device of the invention in an expanded configuration.

FIG. 27 is a view of the device wherein an elongated sheath feature is optically transmissive.

FIG. 28 is an enlarged view of the optically transmissive feature of the device.

FIG. 29 is a cross sectional view of the optically transmissive sheath feature of the device shown in FIGS. 27 and 28.

FIG. 34A is a cross sectional view of the device positioned within an endoscope internal working channel wherein an inflatable member feature is in an unexpanded position.

FIG. 34B is a view of the device shown in FIG. 34A wherein the inflatable member feature is in an expanded position.

FIG. 35A is a cross sectional view of the device positioned within an endoscope internal working channel wherein an expandable member feature is in an unexpanded position.

FIG. 35B is a view of the device shown in FIG. 35A wherein the expandable member feature is in an expanded position.

FIG. 36A is a cross sectional view of the device positioned within an endoscope internal working channel wherein an alternative expandable member feature is in an unexpanded position.

FIG. 36B is a view of the device shown in FIG. 36A wherein the expandable member feature is in an expanded position.

FIG. 43 is an illustration of the ablation device of the invention positioned within an esophagus showing a rotational feature.

FIG. 44 is an illustration of the ablation device of the invention positioned within an esophagus showing a rotational feature combined with an inflation member in an expanded configuration.

FIGS. 45A-45C are views of the ablation device of the invention showing alternative rotational features.

FIGS. 56A and 56B provide views of an ablational device (similar to the devices of FIGS. 38 and 39) but including an ablational surface on a hinge structure or deflecting mechanism similar to that depicted in FIG. 43, the hinge allowing a free pivoting movement of the ablational surface between its longitudinal axis and the longitudinal axis of an endoscope. FIG. 56A shows the device with the ablational surface oriented in parallel with the endoscope. FIG. 56B shows the device with the longitudinal axis of the ablational surface oriented at about a right angle with respect to the longitudinal axis of the endoscope.

FIG. 57A shows the support pulled away from the balloon to clarify that a portion of the support and an edge is adherent to the balloon, and another portion and its edge is not connected to the balloon.

FIG. 57B shows the operative element of the device with the non-adherent portion of the support furled around the balloon in a deployable configuration, the non-adherent portion and its edge overlapping around the adherent portion.

FIG. 57C shows the device of FIGS. 57A and 57B with an optional feature of the operative element, one or more elastic bands wrapped around the electrode support.

FIG. 57D shows the device of FIG. 57C in a collapsed state, with balloon portion being uninflated (or deflated), this being the state of the device when it is being deployed into a lumen and being positioned at a target site, as well as the state of the device after delivering ablation energy and about to be removed from the lumen.

FIG. 58A shows the device in a deployed configuration.

FIG. 58B shows the device of FIG. 58A with the expandable member in an unexpanded or collapsed state, as would be appropriate for deployment of the device to a target tapered surface, or as would be appropriate for removal from the ablational site.

FIG. 58C shows the device of FIG. 58A as it can be deployed into a tapered or concave target site such as the pylorus.

FIG. 58D shows the device of FIG. 58A in an alternative configuration, with the electrode bearing surface of the device reversed such that it is facing proximally, and can thus be pulled retrograde into a tapered or concave site such as the lower esophageal sphincter.

FIG. 59A shows the device in a fully deployed configuration. FIG. 59B shows the device in a stowed configuration that can be drawn into a working channel of an endoscope.

FIG. 61A is a view of the device in its deployed form, after emerging from the working channel. FIG. 61B is a view of the device as it be configured within the working channel prior to deployment, or after having been withdrawn back into the working channel.

FIG. 64A shows a side view of a device with a hydraulic line leading to the ablation surface.

FIG. 65B shows a more detailed perspective view of the ablation surface and the hydraulic intake and multiple outlet holes.

DETAILED DESCRIPTION OF THE INVENTION

Figure 2A:
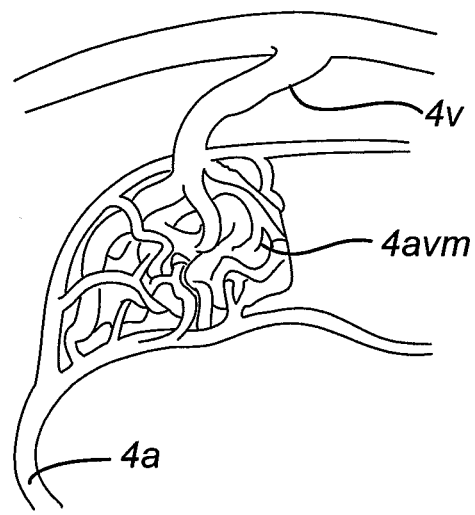
FIGS. 2A-2C provide views of specific examples of conditions that can be a source of acute or chronic bleeding in the gastrointestinal tract.

The use of ablation technologies that make use of a fully circumferential and partially-circumferential ablative structure, some in combination with expandable balloons to position the ablative structure against target tissue has been described in described in US Patents and US Patent Applications. Devices and methods that make use a partially-circumferential ablative structure include the following U.S. patent application Ser. Nos. 11/286,257, 11/286,444, and 11/275,244. Devices and methods that make use a fully-circumferential ablative structure have been described in U.S. Pat. Nos. 6,551,310, and 7,150,745 and in U.S. patent application Ser. No. 11/557,445, Ser. No. 10/370,645, Ser. No. 10/416,923, Ser. No. 11/420,722, Ser. No. 11/420,719, Ser. No. 11/420,714, Ser. No. 11/420,712, Ser. No. 11/469,816 (Shadduck) and U.S. Pat. No. 6,872,206.

The devices and methods may provide an immediate hemostatic effect, or they may remove or alter a lesion that has a propensity to bleed in the future, or the treatment effect may develop overtime in conjunction with wound healing and thus lead to a gradually more effective hemostatic effect. This treatment effect may be achieved over a broad field and is typically coaptive in nature, uniform in depth, controllable to a desired depth, and rapidly delivered. The wide-field aspect of the ablational treatment, per some embodiments of the invention, is due to the large surface area of the device and the ability to reposition the device repeatedly to treat adjacent and non-adjacent areas. Coaptive ablation of blood vessels is considered an advantageous approach for several reasons. First, with the removal or diminishment of blood from the site, the heat sink capacity of the tissue (ability to absorb heat) is lessened thus creating a more effective hemostatic effect. Second, by compressing or collapsing the blood vessel walls together with pressure applied by the device itself prior to applying therapy, the therapy can result in the walls annealing together and thus stopping blood flow. Thus, method steps that favor coaptive coagulation such as the application of appropriate pressure are beneficial for the method. The hemostatic affect is coaptive in nature by virtue of the pressure applied on the targeted tissue or blood vessels included therein by the ablation device. Per embodiments of the invention, a level of pressure, typically exerted by an expandable member of the device when adjacent to the target site or exerted by the physical movement of the endoscope upon which the device is mounted or through which it is passed, is in the range of about 1 to about 15 psig. More particularly, coaptive pressure is in the range of about 3 to about 7 psig. And still more particularly, coaptive pressure is about 4 psig.

Treatment parameters may be such that a uniform level of ablation is achieved in all or part of the targeted lesion. For example, for superficial lesions, the depth of ablation desired may be the mucosa or a portion of the mucosa. For deeper lesions, the depth of ablation may be the deeper mucosa and all or part of the submucosa. Depth control and uniformity of ablation effect are achieved via features of the device and treatment parameters, including electrode pattern, pressure against the targeted lesion, energy density, power density, and number of applications.

Choices of embodiments of the method and devices that are used to treat a specific bleeding site or lesion are dependent upon the organ dimensions within which the bleeding is occurring, the endoscopic access, the size of the bleeding site and lesion, as well as the extent of involvement of the inner lining of the organ. For example, within the gastric antrum in a patient with GAVE, the bleeding lesion may be narrow and linear (like spokes emanating from a wheel) or it may be confluent and circumferential. In the former case, a focal ablation and hemostasis device may be preferred, such as an ablation catheter with a partially-circumferential ablation surface or other such focal devices disclosed herein. In the latter case, a fully-circumferential ablation and hemostasis device may be preferred. Both types of devices (i.e., focal or non-circumferential and circumferential devices) may be variously mounted on an endoscope, passed through an endoscope, or passed along the length of an endoscope. Further, devices may include balloon based or non-balloon based methods of deployment against and compression of the target tissue.

Embodiments of the methods and devices to implement the method may be applied to sites of acute or chronic bleeding in the gastrointestinal tract. FIGS. 1A and 1B provide views of a schematic representation of a cross section of the wall of a portion of the gastrointestinal tract with bleeding blood vessels 4. FIG. 1A shows a portion of a blood vessel, an arteriole or venuole, with branching capillaries that are located primarily in the lamina propria and the epithelium. FIG. 1B shows a portion of a blood vessel, an arteriole or venuole, with branching capillaries that are located primarily in the submucosa and the lamina propria. The point of these figures is that fragile and bleeding blood vessels may reside in specific layers of the gastrointestinal tract. In some cases the histological layers including may be known because of known characteristics of the specific condition. In other cases of acute or chronic bleeding, patient specific information may be available, from patient history, biopsy, or by endoscopic observation either preliminary to the procedure or at the time of the procedure, which can provide indications to localize the problematic blood vessels preferentially to a particular tissue depth. In the example provided by FIG. 1A, it would be appropriate to deliver depth-controlled ablational energy such that ablation occurs in the epithelial layer and in the lamina propria. In the example provided by FIG. 1B, it would be appropriate to deliver depth-controlled ablational energy such that ablation occurs in the submucosa, muscularis mucosae, and in the lamina propria.

Figure 2B:
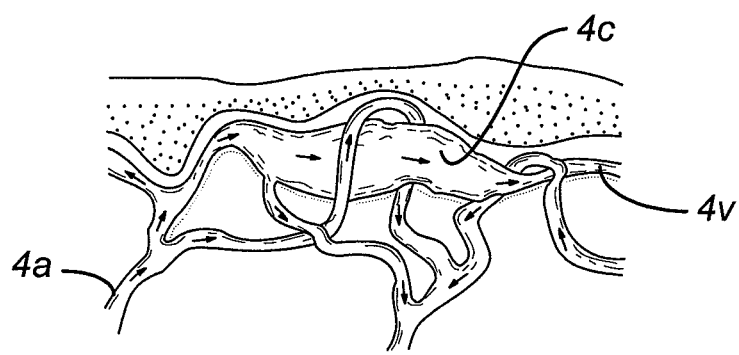
Figure 2C:
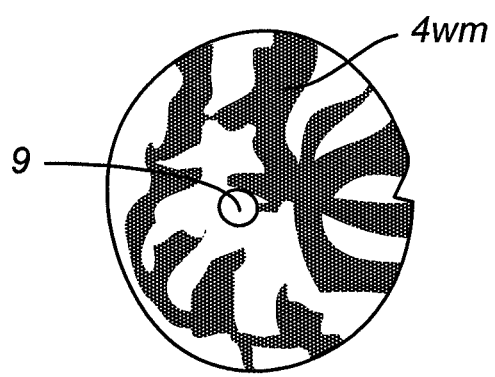

FIGS. 2A-2C provide views of specific examples of conditions that can be a source of acute or chronic bleeding in the gastrointestinal tract, and which are targets of hemostatic ablation per embodiments of methods and devices of this invention. FIG. 2A shows an arteriovenous malformation (AVM) 4*avm* as an entanglement of vessels situated between an upstream artery 4*a* and a downstream vein 4*v*. FIG. 2B provides a schematic view of telangiectases, with a grossly dilated capillary 4*c* situated between an upstream arteriole 4*a* and a downstream venuole 4*v*. FIG. 2C provides an endoscopic distally directed view of the stomach, looking toward the pylorus 9 of a patient with a broad pattern of watermelon stomach lesions 4*wm* that are characteristic of gastric antral vascular ectasia (GAVE). These vascular lesions 4*l* are visible both internally, as visualized by an endoscope, as well as externally, on the skin overlaying the stomach.

Turning now to an aspect of therapeutic ablation methods provided herein, that of determining an appropriate site for ablational treatment (FIG. 3), as well as the amount of ablational energy to be applied during such treatment, such determinations follow from the total amount of clinical information that a clinician can gather on a particular patient. In some embodiments, a preliminary endoscopic examination of a site of acute or chronic gastrointestinal tract bleeding may be appropriate so that any patient-specific features may be mapped out, as well as an evaluation of the general dimensions of the patient's alimentary canal. Such information may be obtained by direct visual observation by endoscopic approaches, with optional use of mucosal in-situ staining agents may further be accomplished by other diagnostic methods, including non-invasive penetrative imaging approaches such as narrow band imaging from an endoscope, or with any conventional method known in the art. In one aspect, evaluation of a site includes identifying the locale of the site, including its dimensions. In another aspect, evaluation of target tissue area includes identifying a multiplicity of sites, if there is more than one site, and further identifying their locale and their respective dimensions. In still another aspect, evaluating target sites may include identifying or grading any pathology or injury or specific features of site(s) of acute or chronic gastrointestinal tract bleeding, and particularly identifying any areas of clinical significance or concern that are overlapping or near the areas that are to be targeted for ablation.

Once target sites for ablation have been identified, target tissue at a site of acute or chronic gastrointestinal tract bleeding may be treated with embodiments of an inventive ablational device and associated methods as described herein. Evaluation of the status of target tissue sites for ablation, particularly by visualization approaches, may also be advantageously implemented as part of an ablational therapy method (FIG. 3), as for example, in close concert with the ablation, either immediately before the application of ablational energy (such as radiant energy), and/or immediately thereafter. Further, the treatment site can be evaluated by any diagnostic or visual method at some clinically appropriate time after the ablation treatment, as for example a few days, several weeks, or several few months, or at anytime when clinically indicated following ablational therapy. In the event that any follow-up evaluation shows either that the therapy was unsatisfactorily complete, or that there is a recovery in the population of cells targeted for ablation, a repetition of the ablational therapy may be indicated.

Turning now to aspects of ablational devices that can be directed toward ablational correction of failed bypass procedures, as described in detail herein, ablational devices have an ablational structure arrayed with energy-transmitting elements such as electrodes. In some embodiments, depending on the type of ablatative energy being used in the therapy, the devices may be mounted on, or supported by any appropriate instrument that allows movement of the ablational surface to the local of a target site. Such instruments are adapted in form and dimension to be appropriate for reaching the target tissue site, and may include simple catheters adapted for the purpose; some embodiments of the insertive instrument include endoscopes that, in addition to their supportive role, also provide a visualization capability. In some embodiments of the method, an endoscope separate from the supportive instrument may participate in the ablational procedure by providing visual information.

Exemplary embodiments of the inventive device as described herein typically make use of electrodes to transmit radiofrequency energy, but this form of energy transmission is non-limiting, as other forms of energy, and other forms of energy-transmission hardware are included as embodiments of the invention. Ablational energy, as provided by embodiments of the invention, may include, by way of example, microwave energy emanating from an antenna, light energy emanating from photonic elements, thermal energy transmitted conductively from heated ablational structure surfaces or as conveyed directly to tissue by heated gas or liquid, or a heat-sink draw of energy, as provided by cryonic or cryogenic cooling of ablational structure surfaces, or as applied by direct contact of cold gas or sprayed fluid or mist with tissue, or by heat-draw through a wall of a device that separates the cold gas or fluid from the tissue.

Figure 3:
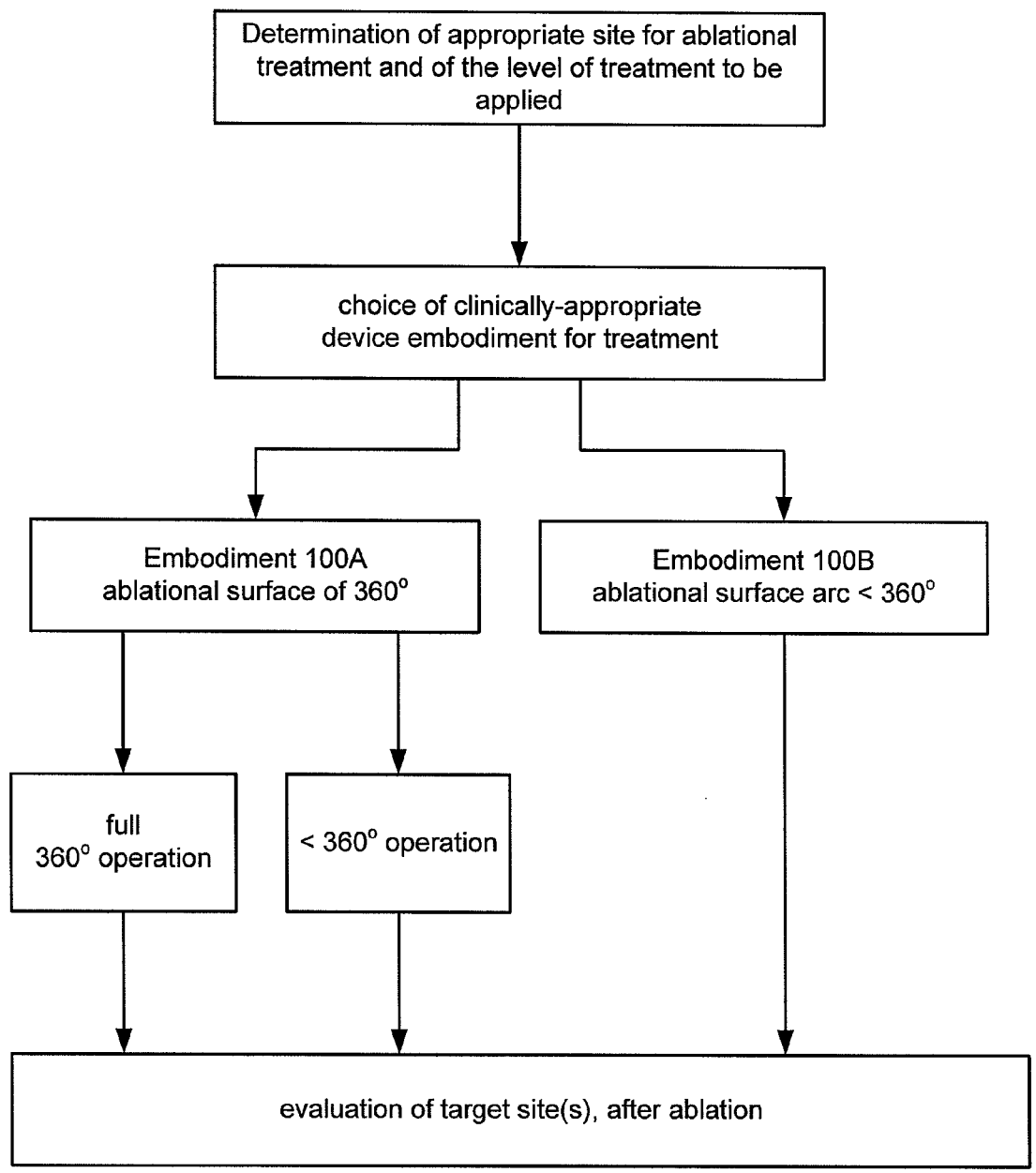
FIG. 3 is a flow diagram depicting an overview of the method, wherein an appropriate site for ablational intervention for the treatment of a site of acute or chronic gastrointestinal tract bleeding, the level of ablational therapy is determined, and at least preliminary information is gained regarding localization, and clinical judgment is exercised as to which embodiment of the invention is preferable.

Embodiments of the ablational device include variations with regard to the circumferential expanse of the ablational surface to be treated, some embodiments provide a fully circumferential ablation surface and others provide a surface that is less than fully circumferential, as described above. Choosing the appropriate device is a step included within the therapeutic method provided, as shown in FIG. 3. These and other variation may provide particular advantages depending on the nature, extent, locale, and dimensions of the one or more targeted tissue sites on the wall the alimentary canal. One embodiment of the invention includes a device with an ablational surface that is fully circumferential, i.e., encompassing a radius of 360 degrees, such that a full radial zone within a luminal organ is subject to ablation. Within that zone, ablation may be implemented to a varying degree, depending on the energy output and the pattern of the ablational elements (such as electrodes), but with substantial uniformity within the zone of ablation. This embodiment may be particularly appropriate for treating widespread or diffuse sites within a site of acute or chronic gastrointestinal tract bleeding. In another embodiment of the device, the ablational surface of the inventive device is partially circumferential, such that it engages a fraction of the full internal perimeter or circumference of a luminal organ. The fractional portion of the circumference ablated on the inner surface of a luminal organ depends on the size and conformation of the luminal organ being treated (radius, diameter, or circumference, or angularity) and on the dimensions of the ablational surface, as detailed further below. With regard to treating target sites that are small and discrete, the smaller or more discrete ablational surface provided by this latter embodiment may be advantageous.

This type of operational control of a circumferential subset of ablation energy elements around a 360-degree circumferential array is analogous to the fractional operation of a patterned subset of an electrode array, as described below in the section titled "Electrode patterns and control of ablation patterns across the surface area of tissue". In the partially-circumferential operation of an array, a particular arc of the array is activated to deliver energy to an arc of the circumference. In the fractional-pattern operation of an array, energy is delivery to a portion of the tissue in the target area, while another portion receives insufficient energy to achieve ablation. In some embodiments, these operational variations can be combined, that is, a patterned subset of a circumferential arc can be activated.

Figure 4:
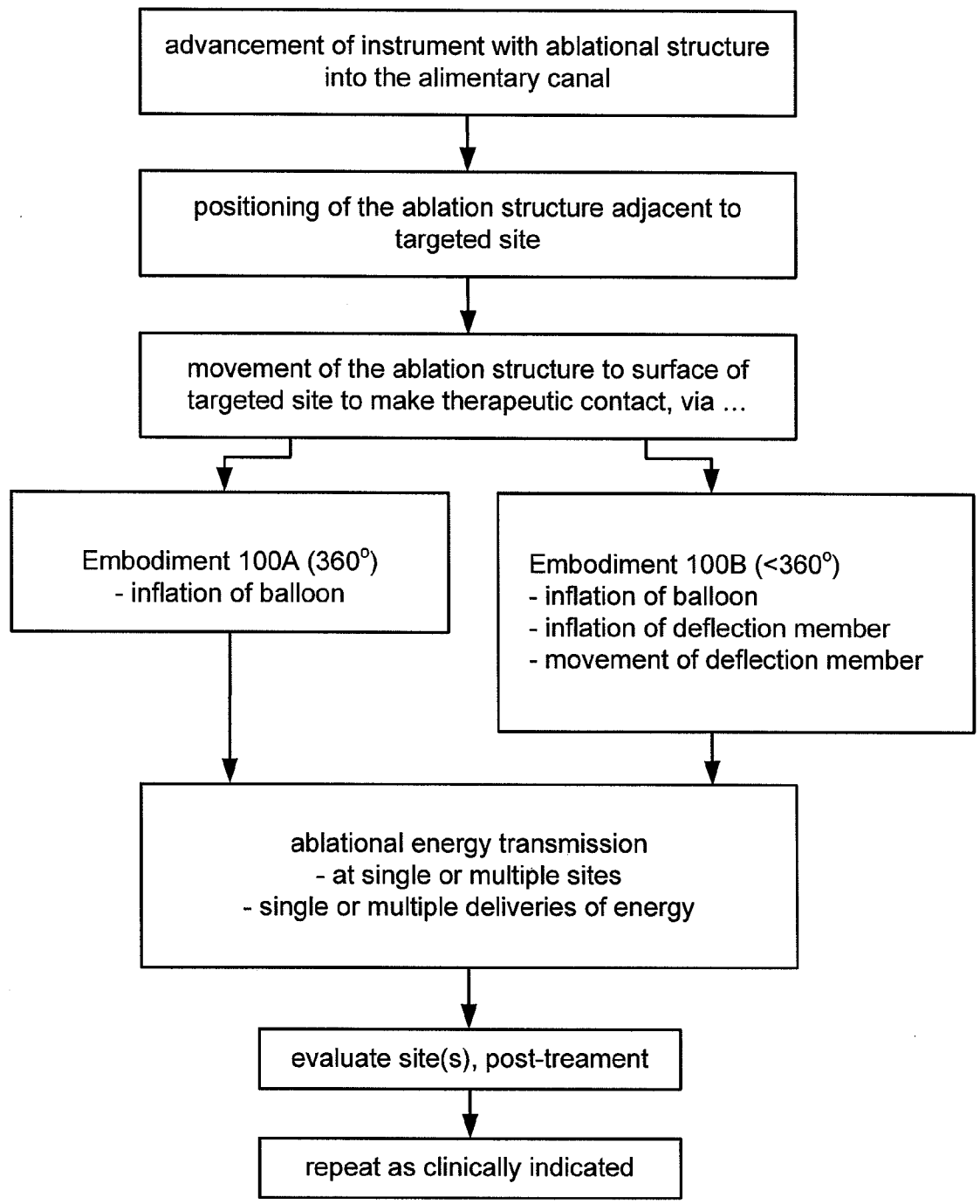
FIG. 4 is a flow diagram depicting the method after the site of ablation of a site of acute or chronic gastrointestinal tract bleeding has been localized and a choice has been made regarding the preferred ablational device. The method includes an evaluation of the site, including particulars of location, stage, determination of the number of sites, and the dimensions. The method continues with insertion of the instrument and its movement to the locale of the ablational target tissue, the more refined movement of the ablational structure that create a therapeutically effective contact, the emission of ablational radiation and then post-treatment evaluation.

FIGS. 3 and 4 together provide flow diagram depictions of embodiments of the method for ablating tissue at a site of acute or chronic gastrointestinal tract bleeding. The diagrams represent common aspects of the embodiments of the method, as delivered by two embodiments of the device, one which has a 360 degree circumferential ablation structure, and one which has an ablation structure comprising an arc of less than 360 degrees.

FIG. 3 is a flow diagram depicting an overview of the method with a focus on patient evaluation and determination of a clinically appropriate site within the alimentary canal for ablational treatment. In another step, a responsible clinician makes an informed choice with regard to the appropriate embodiment with which to treat the patient, i.e., either a device with the 360 degree electrode array 100A, or a device 100B with the electrodes arrayed in an arc of less than 360 degrees. In the event that the device 100A is chosen for use, another treatment choice may be made between operating the electrodes throughout the 360 degree circumference, or whether to operate a radial subset of the electrode array. In another step, a clinician further considers and makes a determination as to the protocol for ablation, considering the amount of energy to be delivered, the energy density, the duration of time over which energy is to be delivered. These considerations take into the account the surface area to be ablated, the depth of tissue which is to be treated, and the features of the electrode array, whether, for example, it is to be a fractional electrode, and which pattern may be desirable. Regardless of the device chosen, another preliminary step to operating the method may include a closer evaluation of the target tissue site(s) within the alimentary canal. Evaluation of the site may include the performance of any visualization or diagnostic method that provides a detailed census of the number of discrete target tissue sites, their dimensions, their precise locations, and/or their clinical status, whether apparently normal or abnormal. This step is shown following the choice of instrument, but may occur simply in conjunction with diagnosis, or at any point after diagnosis and general localization of the target tissue. In any case, an evaluating step is typically performed prior to ablation, as outlined in the operational steps of the method, as shown in the flow diagram of FIG. 4. In the description that follows below, the label 100 may generally be used to designate ablational devices, regardless of whether their ablational surface 101 is fully circumferential or partially circumferential.

FIG. 4 is a flow diagram depicting the method after the target site at a site of acute or chronic gastrointestinal tract bleeding has been localized and a choice has been made regarding the preferred ablational device. The method includes an evaluation of the site, including particulars of location, stage, determination of the number of sites, and the dimensions, as described above, and using approaches detailed in the references provided in the background, and/or by using whatever further approaches may be known by those practiced in the art. The method continues with insertion of the instrument and the movement of the ablational structure to the locale of the target tissue to be ablated. Subsequently, more refined movements of the ablational structure may be performed that create a therapeutically effective contact between the ablational structure and the target tissue site. In the event that the 360 degree embodiment of the device 100A is chosen, therapeutically effective contact may be made by inflating a balloon underlying the electrode array. In the event that the embodiment chosen is 100B, the device with an electrode surface spanning an arc of less than 360 degrees, movements that bring the ablational surface into therapeutically effective contact may include any of inflation of a balloon, inflation of a deflection member, and/or movement of a deflection member, all of which are described further below.

After therapeutically-effective contact is made, by either device embodiment 100A or 100B, and by whatever type of movement was that was taken, a subsequent step includes the emission of ablational energy from the device. Variations of ablational energy emission may include ablating a single site as well as moving the instrument to a second or to subsequent sites that were identified during the evaluation step. Following the ablational event, a subsequent step may include an evaluation of the treated target site; alternatively evaluation of the consequences of ablation may include the gathering of clinical data and observation of the patient. In the event that an endoscope is included in the procedure, either as the instrument supporting the ablational structure, or as a separate instrument, such evaluation may occur immediately or very soon after ablation, during the procedure, when instruments are already in place. In other embodiments of the method, the treated site may be evaluated at any clinically appropriate time after the procedure, as for example the following day, or the following week, or many months thereafter. In the event that any of these evaluations show an ablation that was only partially complete, or show an undesired repopulation of targeted cells, the method appropriately includes a repetition of the steps just described and schematically depicted in FIG. 4.

Device and Method for 360 Degree Circumferential Ablation

Methods for accomplishing ablation of vascular tissue at a site of acute or chronic gastrointestinal tract bleeding according to this invention include the emission of radiant energy at levels to accomplish ablation of sites of bleeding in the gastrointestinal tract. In typical embodiments described in this section, the radiant energy distribution elements are configured circumferentially around 360 degrees. Alternatively to using emission of RF energy from the ablation structure, other energy sources can be used with the ablation structure to achieve tissue ablation and may not require electrodes. Such alternate energy sources include: ultraviolet light, microwave energy, ultrasound energy, thermal energy transmitted from a heated fluid medium, thermal energy transmitted from heated element(s), heated gas such as steam heating the ablation structure or directly heating the tissue through steam-tissue contact, light energy either collimated or non-collimated, cryogenic energy transmitted by cooled fluid or gas in or about the ablation structure or directly cooling the tissue through cryogenic fluid/gas-tissue contact. Embodiments of the system and method that make use of these aforementioned forms of ablational energy include modifications such that structures, control systems, power supply systems, and all other ancillary supportive systems and methods are appropriate for the type of ablational energy being delivered.

In some embodiments of a fully circumferential ablation device, the flexible shaft comprises a cable surrounded by an electrical insulation layer and comprises a radiant energy distribution elements located at its distal end. In one form of the invention, a positioning and distending device around the distal end of the instrument is of sufficient size to contact and expand the walls of the gastrointestinal tract at a site of acute or chronic bleeding in which it is placed (e.g. the stomach, pylorus, small intestine, rectum, or anus) both in the front of the energy distribution elements as well as on the sides of the energy distribution elements. For example, the distal head of the instrument can be supported at a controlled distance from the wall of the gastrointestinal tract at a site of acute or chronic bleeding by an expandable balloon or inflation member, such that a therapeutically-effective contact is made between the ablation structure and the target site so as to allow regulation and control the amount of energy transferred to the target tissue within the lumen when energy is applied through the electrodes. The balloon is preferably bonded to a portion of the flexible shaft at a point spaced from the distal head elements.

Some embodiments of a fully-circumferential ablation device include a distendible or expandable balloon member as the vehicle to deliver the ablation energy. One feature of this embodiment includes means by which the energy is transferred from the distal head portion of the invention to the membrane comprising the balloon member. For example, one type of energy distribution that may be appropriate and is incorporated herein in its entirety is shown in U.S. Pat. No. 5,713,942, in which an expandable balloon is connected to a power source that provides radio frequency power having the desired characteristics to selectively heat the target tissue to a desired temperature. A balloon per embodiments of the current invention may be constructed of an electroconductive elastomer such as a mixture of polymer, elastomer, and electroconductive particles, or it may comprise a nonextensible bladder having a shape and a size in its fully expanded form which will extend in an appropriate way to the tissue to be contacted. In another embodiment, an electroconductive member may be formed from an electroconductive elastomer wherein an electroconductive material such as copper is deposited onto a surface and an electrode pattern is etched into the material and then the electroconductive member is attached to the outer surface of the balloon member. In one embodiment, the electroconductive member, e.g. the balloon member, has a configuration expandable in the shape to conform to the dimensions of the expanded (not collapsed) inner lumen of the human gastrointestinal tract at a site of acute or chronic bleeding. In addition, such electroconductive member may consist of a plurality of electrode segments arrayed on an ablation structure 101 having one or more thermistor elements associated with each electrode segment by which the temperature from each of a plurality of segments is monitored and controlled by feedback arrangement. In another embodiment, it is possible that the electroconductive member may have means for permitting transmission of microwave energy to the ablation site. In yet another embodiment, the distending or expandable balloon member may have means for carrying or transmitting a heatable fluid within one or more portions of the member so that the thermal energy of the heatable fluid may be used as the ablation energy source.

Some embodiments of a fully circumferential ablation device include a steerable and directional control means, a means for accurately sensing depth of cautery, and appropriate alternate embodiments so that in the event of a desire not to place the electroconductive elements within the membrane forming the expandable balloon member it is still possible to utilize the balloon member for placement and location control while maintaining the energy discharge means at a location within the volume of the expanded balloon member, such as at a distal energy distribution head.

Embodiments of the invention include methods whereby an ablation device, such as a fully circumferential ablation device, is used to treat sites of acute or chronic bleeding at sites in the gastrointestinal tract. After determining that the portion or portions of the gastrointestinal tract wall at a site of acute or chronic bleeding having this tissue that is targeted either for full or partial ablation, the patient is prepared for a procedure in a manner appropriate according to the embodiment of the device to be utilized. Then, the practitioner inserts into the patient, in one embodiment, the ablation device shown and discussed herein via endoscopic access and control. Further positioning of portions of the device occurs as proper location and visualization identifies the ablation site at a site of acute or chronic gastrointestinal tract bleeding. Selection and activation of the appropriate quadrant(s) or portion(s)/segment(s) on the ablation catheter member is performed by the physician, including appropriate power settings according to the depth of cautery desired. Additional settings may be necessary as further ablation is required at different locations and/or at different depths within the patient's gastrointestinal tract at a site of acute or chronic bleeding. Following the ablation, appropriate follow-up procedures as are known in the field are accomplished with the patient during and after removal of the device from the site of acute or chronic gastrointestinal tract bleeding.

In yet another method of the invention, the practitioner may first determine the length of the portion of the site of acute or chronic gastrointestinal tract bleeding requiring ablation and then may choose an ablation catheter from a plurality of ablation catheters of the invention, each catheter having a different length of the electrode member associated with the balloon member. For example, if the practitioner determines that 1 centimeter of the site of acute or chronic gastrointestinal tract bleeding surface requires ablation, an ablation catheter having 1 centimeter of the electrode member can be chosen for use in the ablation. The length of the electrode member associated with the balloon member can vary in length, as for example, from 1 to 10 cm.

In yet another embodiment, a plurality of ablation catheters wherein the radiant energy distribution elements are associated with the balloon member can be provided wherein the diameter of the balloon member when expanded varies from 12 mm to 40 mm. In this method, the practitioner will choose an ablation catheter having a diameter when expanded which will cause the a site of acute or chronic gastrointestinal tract bleeding to stretch and the mucosal layer to thin out, thus, reducing or occluding blood flow at the site of the ablation. It is believed that by reducing the blood flow in the area of ablation, the heat generated by the radiant energy is less easily dispersed to other areas of the target tissue thus focusing the energy to the ablation site.

One approach a practitioner may use to determine the appropriate diameter ablation catheter to use with a particular patient is to use in a first step a highly compliant balloon connected to a pressure sensing mechanism. The balloon may be inserted into a luminal organ within the site of acute or chronic gastrointestinal tract bleeding and positioned at the desired site of the ablation and inflated until an appropriate pressure reading is obtained. The diameter of the inflated balloon may be determined and an ablation device of the invention having a balloon member capable of expanding to that diameter chosen for use in the treatment. In the method of this invention, it is desirable to expand the expandable electroconductive member such as a balloon sufficiently to occlude the vasculature of the submucosa, including the arterial, capillary or venular vessels. The pressure to be exerted to do so should therefore be greater than the pressure exerted by such vessels.

In other embodiments of the method, electronic means are used for measuring the luminal target area of gastrointestinal features that have been formed by bariatric surgery so that energy may be appropriately normalized for the surface area of the target tissue. These aspects of the method are described in detail in U.S. patent application Ser. No. 12/143,404, of Wallace et al., entitled "Electrical means to normalize ablational energy transmission to a luminal tissue surface of varying size", as filed on Jun. 20, 2008, which is incorporated in entirety.

Figure 6:
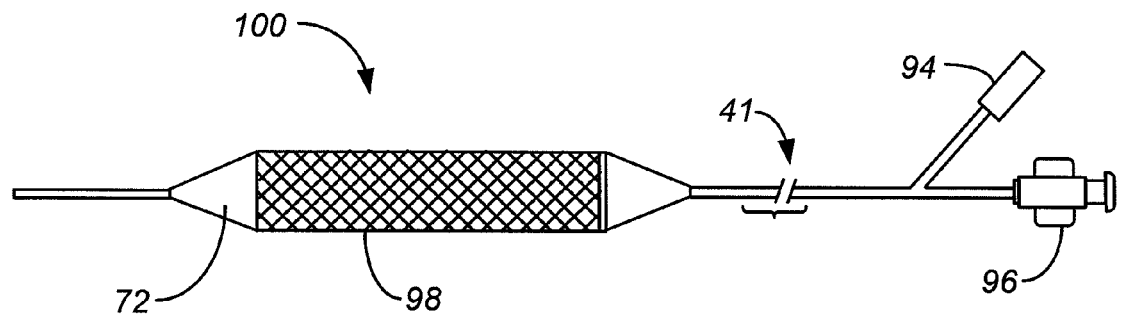
FIG. 6 is a view of an embodiment of an ablative device with a fully circumferential operating radius, with a balloon member in an expanded configuration.

In addition to the representative embodiment of an ablation device with a fully-circumferential ablation surface that can be pressed against a target area to achieve therapeutic contact by way of an expandable member that is shown in FIG. 6, other representative embodiments are provided in FIGS. 57A-57D and FIGS. 58A and 58B. The embodiments shown in FIGS. 57A-57D are described in detail in U.S. patent application Ser. No. 12/143,404, of Wallace et al., entitled "Electrical means to normalize ablational energy transmission to a luminal tissue surface of varying size", as filed on Jun. 20, 2008, incorporated herein its entirety. An embodiment of a device with a 360 degree ablational surface is described in detail in that application, and is depicted in FIGS. 57A-57D of this application. Pressure sensing means may also be used to measure the size of a lumen in preparation for an ablation treatment, as described in U.S. patent application Ser. No. 11/244,385 of Jackson, published as US 2006/0095032.

Figure 57A:
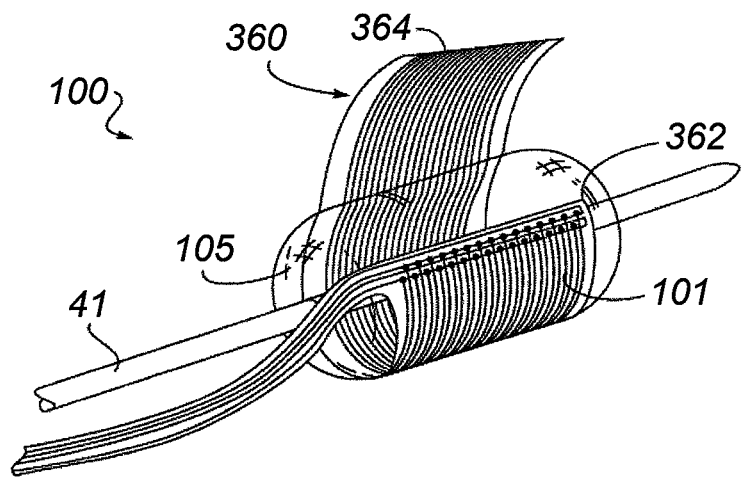
FIG. 57A-57D provide perspective views of an ablation device with a 360 degree circumferential ablation surface on an overlapping electrode support furled around an expandable balloon, the operative element including a balloon and an electrode support in an expanded state.
Figure 57B:
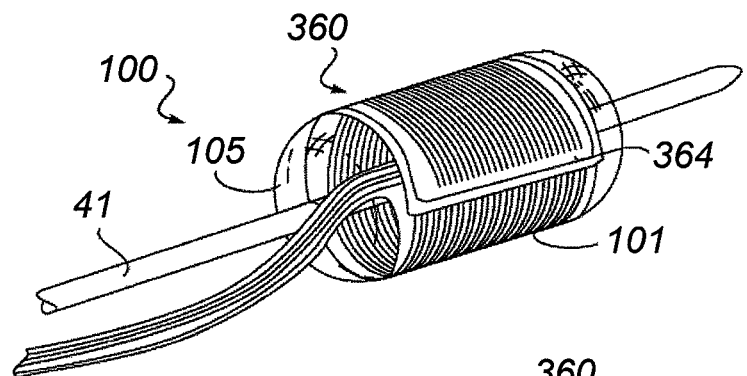
Figure 57C:
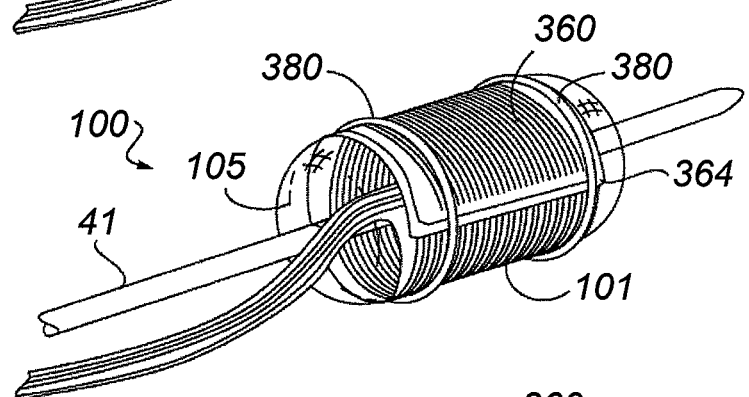
Figure 57D:
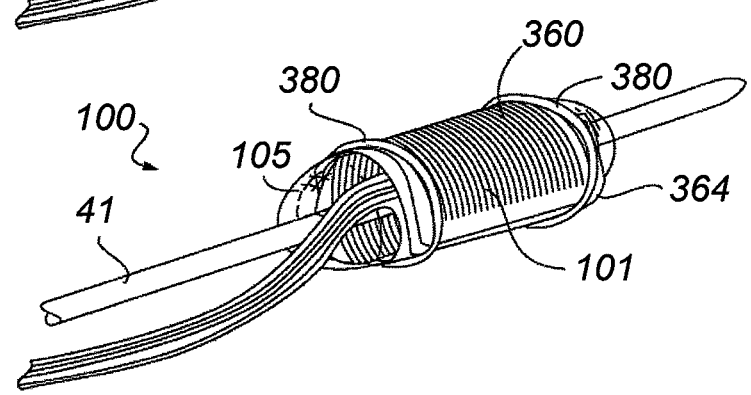

An embodiment of a device disclosed in U.S. patent application Ser. No. 12/143,404, of Wallace et al will be described here briefly, in order to provide an embodiment that includes a 360-degree ablational surface arranged on an overlapping support that expands in accordance with a balloon enclosed within the circumference of the support. Although the circumference of the device as a whole expands with the balloon, the ablational surface itself is non-distensible, and maintains its electrode density. FIGS. 57A-57D provide perspective views of an ablation device 100 with an overlapping electrode support 360 furled around an expandable balloon 105. An array of ablational energy delivery elements 101 such as radiofrequency electrodes is arranged on the exterior surface of the electrode support. The operative element is mounted on the distal end of an ablation catheter, of which the distal portion of a shaft 41 is seen, and around which the balloon 105 is configured. FIG. 57A shows the electrode support 360 pulled away from the balloon 105 to clarify that a portion of the support and an inner edge 362 is adherent to the balloon, and another portion and its outer edge 364 is not connected to the balloon. FIG. 57B shows the non-adherent portion of the electrode support 360 furled around the balloon 105 in a deployable configuration, the non-adherent portion and its edge overlapping around the adherent portion. FIG. 57C shows an optional feature of the device 100A, one or more elastic bands 380 wrapped around the electrode support 360. In some embodiments, the elastic band 380 material is a conductive elastomer, as described in greater detail below, which can be included in a size-sensing circuit to provide information related to the degree of expansion of the operative element. FIG. 57D shows the device of FIG. 57C in a collapsed state, with balloon portion 105 being uninflated (or deflated), this being the state of the device when it is being deployed into a lumen and being positioned at a target site, as well as the state of the device after delivering ablation energy and about to be removed from the lumen.

Figure 58A:
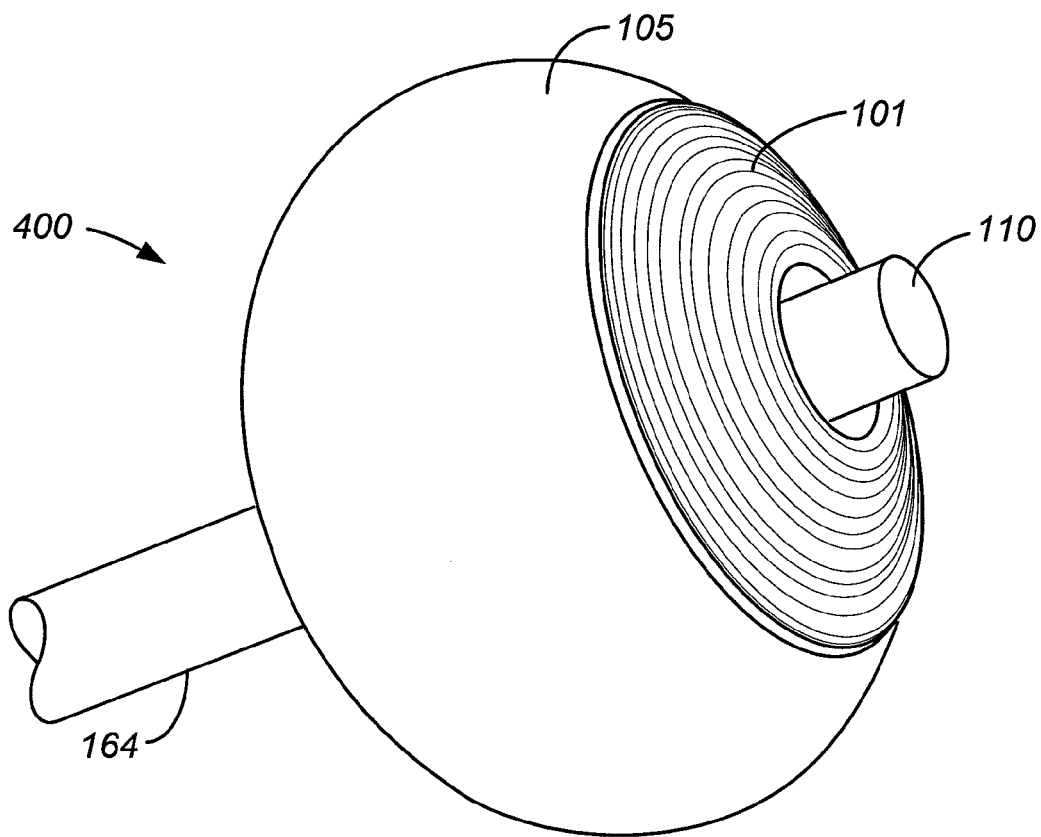
FIGS. 58A-58D depict an embodiment of an ablation device that is adapted to present an ablational surface into a concave or inwardly tapered target site such as a stoma or pylorus. The device includes an ablational surface circumferentially arranged on the distal portion of an expandable member, the expandable member mounted around the distal end of an endoscope.
Figure 58B:
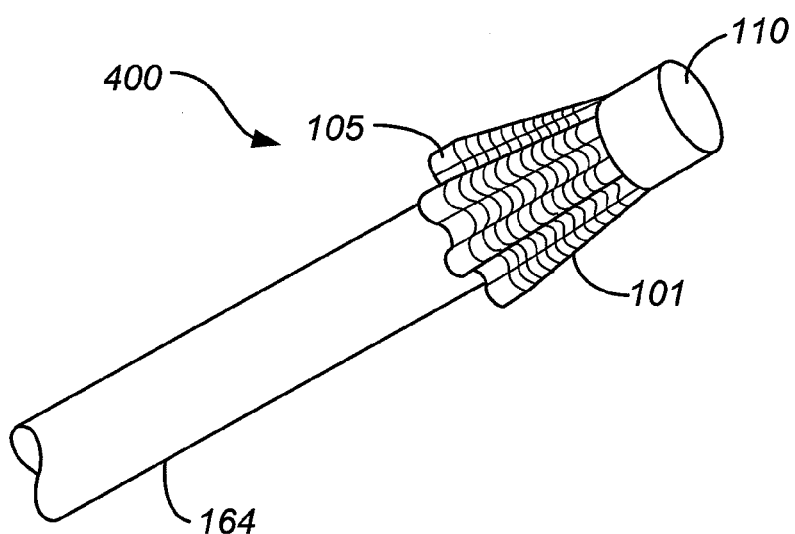
Figure 58C:
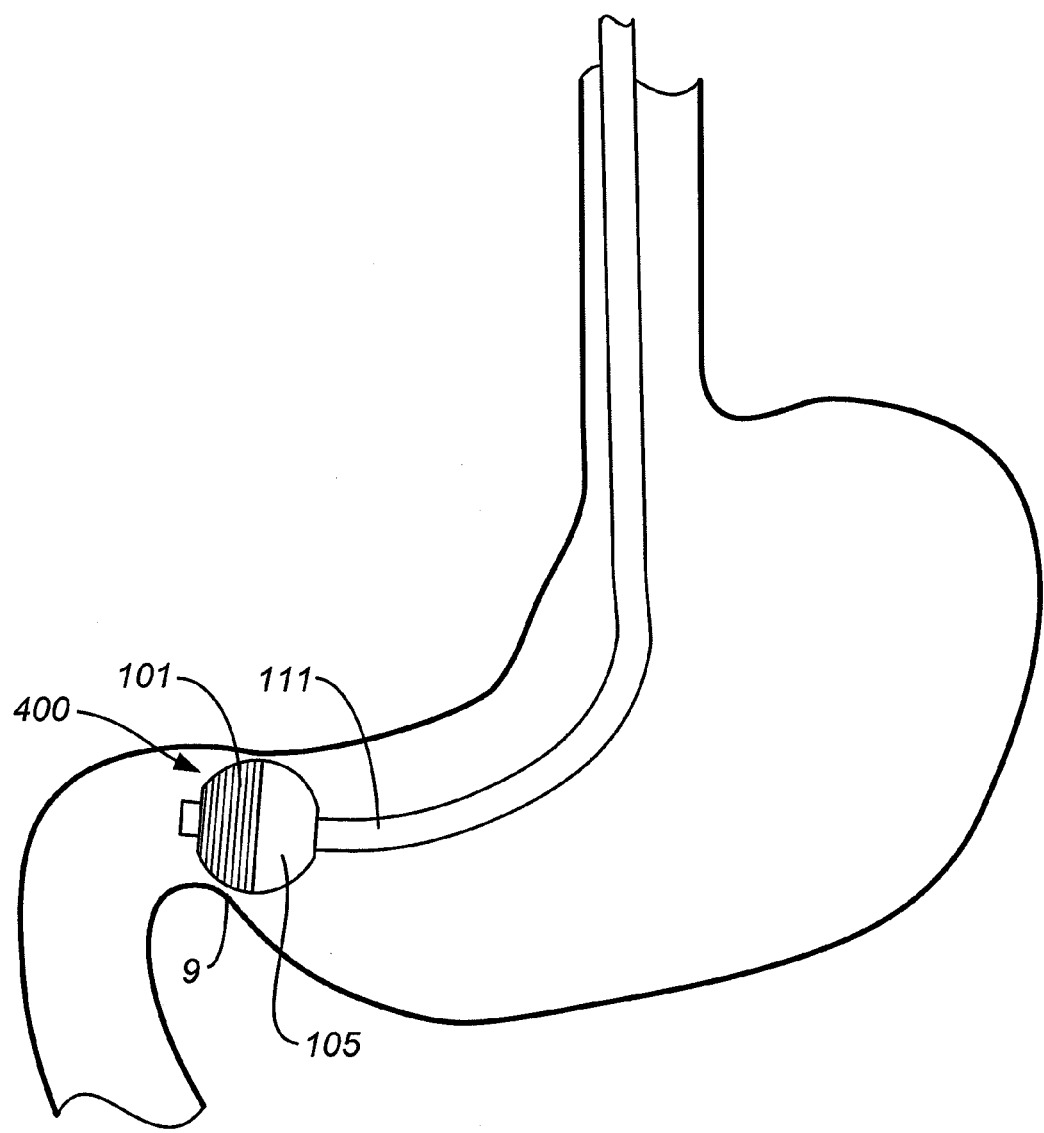
Figure 58D:
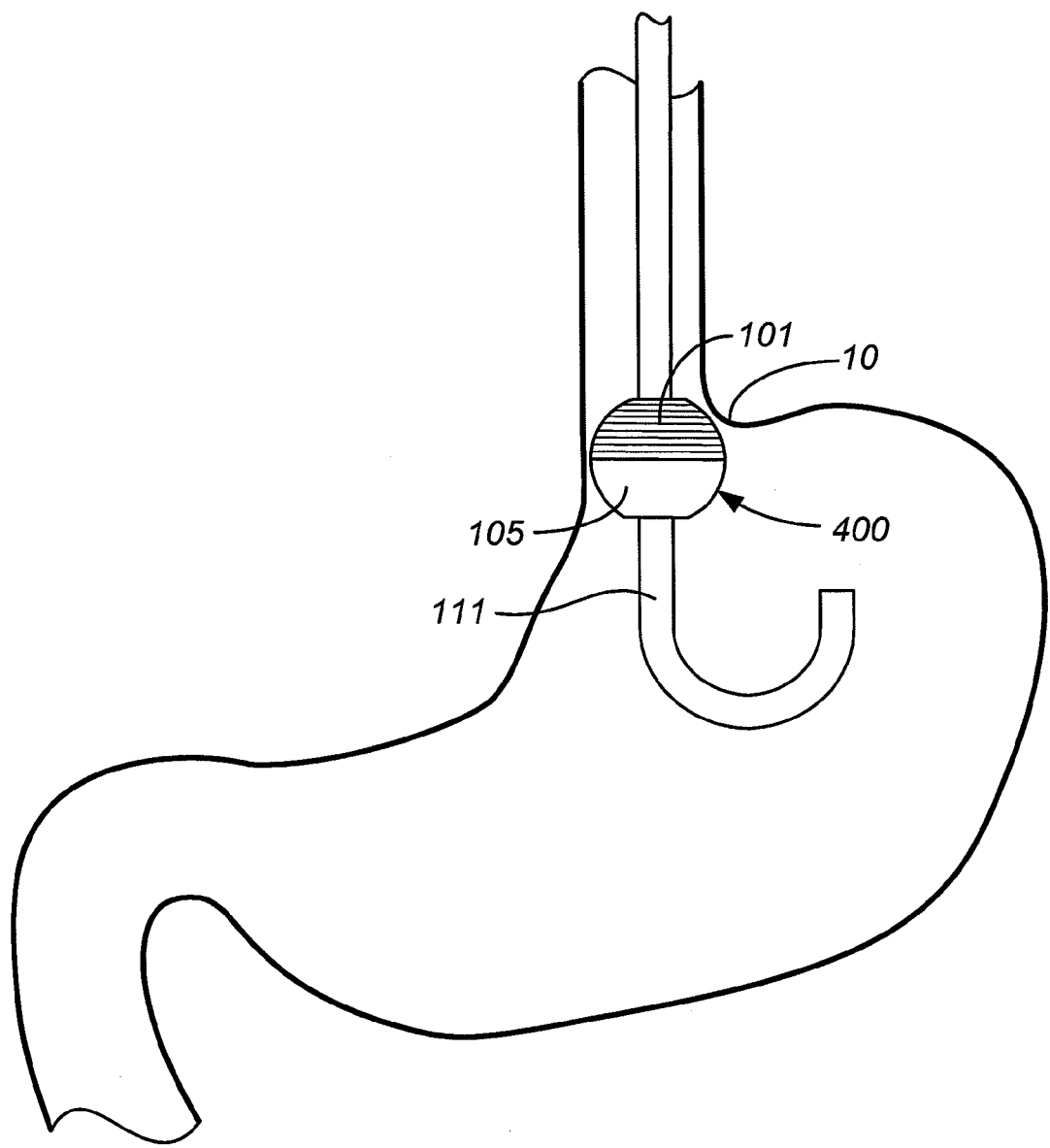

Another embodiment of an ablation device with a fully circumferential ablation surface is provided in FIGS. 58A-58B. This particular device embodiment 400 is adapted to present an ablational surface 101 into a concave or inwardly tapered target site such as distal portion of the antrum of the stomach, or in the vicinity of the pylorus, which is a site for vascular lesions typical of watermelon stomach. The device includes an ablational surface circumferentially arranged on the distal portion of an expandable member 105, the expandable member mounted around the distal end 110 of the shaft of an endoscope 111. FIG. 58A shows the device in a deployed configuration. FIG. 58B shows the device with the expandable member in an unexpanded or collapsed state, as would be appropriate for deployment of the device to a target tapered surface, or as would be appropriate for removal from the ablational site. FIG. 58C shows the device of FIG. 58A as it can be deployed into a tapered or concave target site such as the pylorus 9. FIG. 58D shows the device of FIG. 58A in an alternative configuration, with the electrode bearing surface of the device reversed such that it is facing proximally, and can thus be pulled retrograde into a tapered or concave site such as the lower esophageal sphincter 10.

Figure 7A:
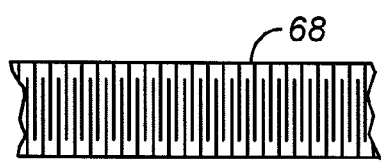
FIGS. 7A-7C show the electrode patterns of the device of FIG. 5.
Figure 7B:
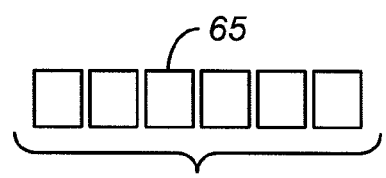
Figure 7C:
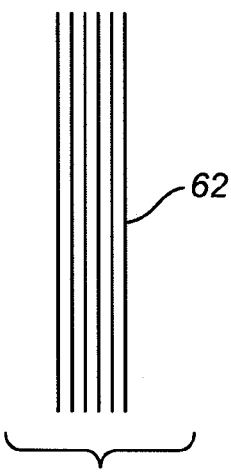
Figure 8A:
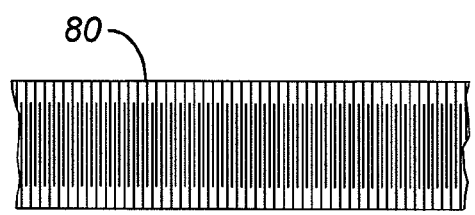
FIGS. 8A-8D show electrode patterns that may be used with embodiments of the ablative device with a fully circumferential operating radius, or with any device embodiments described herein.
Figure 8B:
Figure 8C:
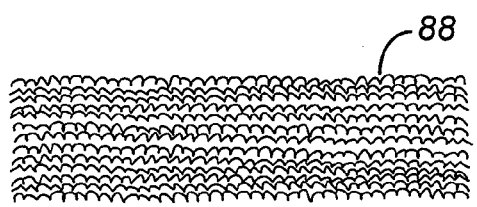
Figure 8D:
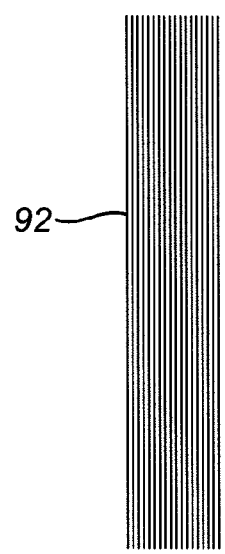

Electrode Patterns and Control of Ablation Patterns Across the Surface Area of Tissue Some aspects of embodiments of the ablational device and methods of use will now be described with particular attention to the electrode patterns present on the ablation structure. The device used is shown schematically in FIGS. 5-7. As shown in FIG. 6, the elongated flexible shaft 41 of a device 100 with a fully circumferential ablation surface is connected to a multi-pin electrical connector 94 which is connected to the power source and includes a male luer connector 96 for attachment to a fluid source useful in expanding the expandable member. The elongated flexible shaft has an electrode 98 wrapped around the circumference. The expandable member of the device shown in FIGS. 5 and 6 further includes three different electrode patterns, the patterns of which are represented in greater detail in FIGS. 7A-7C. Typically, only one electrode pattern is used in a device of this invention, although more than one may be included. In the device shown in FIG. 5, the elongated flexible shaft 41 comprises six bipolar rings 62 with about 2 mm separation at one end of the shaft (one electrode pattern), adjacent to the bipolar rings is a section of six monopolar bands or rectangles 65 with about 1 mm separation (a second electrode pattern), and another pattern of bipolar axial interlaced finger electrodes 68 is positioned at the other end of the shaft (a third electrode pattern). In this device, a null space 70 is positioned between the last of the monopolar bands and the bipolar axial electrodes. The catheter used in the study was prepared using a polyimide flat sheet of about 1 mil (0.001") thickness coated with copper. The desired electrode patterns were then etched into the copper.

Figure 5:
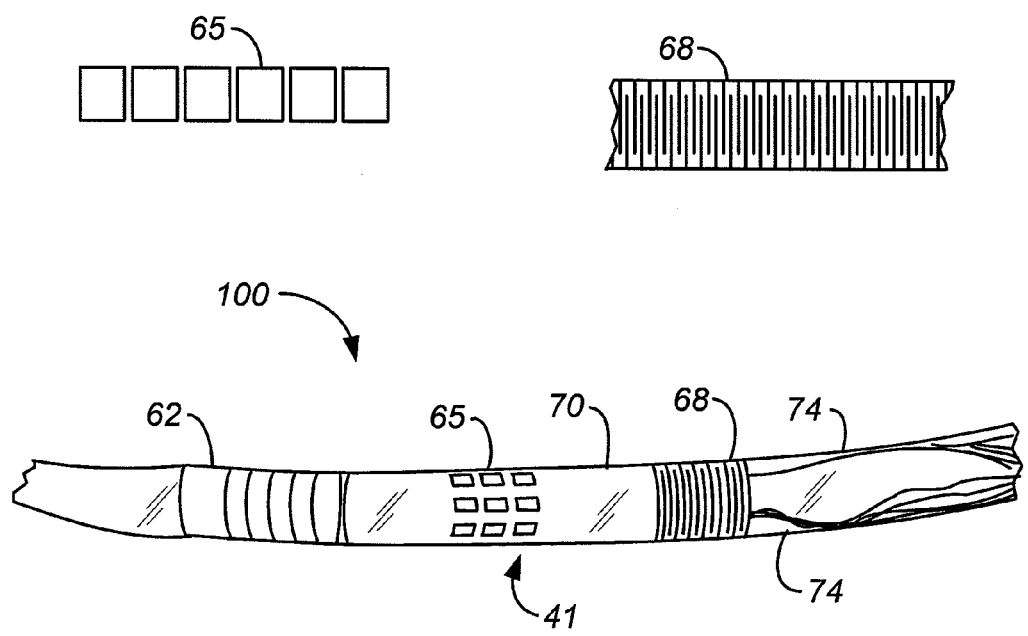
FIG. 5 is a view of an embodiment of an ablative device with a fully circumferential operating radius.

Alternative electrode patterns are shown in FIGS. 8A-8D as 80, 84, 88, and 92, respectively. Pattern 80 is a pattern of bipolar axial interlaced finger electrodes with about 0.3 mm separation. Pattern 84 includes monopolar bands with 0.3 mm separation. Pattern 88 is that of electrodes in a pattern of undulating electrodes with about 0.25 mm separation. Pattern 92 includes bipolar rings with about 0.3 mm separation. In this case the electrodes are attached to the outside surface of a balloon 72 having a diameter of about 18 mm. The device may be adapted to use radio frequency by attaching wires 74 as shown in FIG. 5 to the electrodes to connect them to the power source.

The preceding electrode array configurations are described in the context of an ablation structure with a full 360 degree ablation surface, but such patterns or variants thereof may also be adapted for ablation structures that provide energy delivery across a surface that is less than completely circumferential, in structures, for example, that ablate over any portion of a circumference that is less than 360 degrees, or for example structures that ablate around a radius of about 90 degrees, or about 180 degrees.

Embodiments of the ablation system provided herein are generally characterized as having an electrode pattern that is substantially flat on the surface of an ablation support structure and which is non-penetrating of the tissue that it ablates. The electrode pattern forms a contiguous treatment area that comprises some substantial radial aspect of a luminal organ; this area is distinguished from ablational patterns left by electrical filaments, filament sprays, or single wires. In some embodiments of the invention the radial portion may be fully circumferential; the radial portion of a luminal organ that is ablated by embodiments of the invention is function of the combination of (1) the circumference of the organ, which can be relatively large in the case of the stomach, and small when in the case of a region in the small intestine or anus, and (2) the dimensions of the electrode pattern. Thus, at the high end, as noted, the radial expanse of a treatment area may be as large as 360 degrees, and as small as about 5 to 10 degrees, as could be the case in a treatment area within the stomach.

Embodiments of the ablational energy delivery system and method provided are also characterized by being non-penetrating of the target tissue. Ablational radiofrequency energy is delivered from the flat electrode pattern as it makes therapeutic contact with the tissue surface of a treatment area, as described elsewhere in this application; and from this point of surface contact, energy is directly inwardly to underlying tissue layers.

Some embodiments of the ablational system and method provided herein can be further characterized by the electrode pattern being configured to achieve a partial or fractional ablations, such that only a portion of the tissue surface receives sufficient radiofrequency energy to achieve ablation and another portion of the surfaces receives insufficient energy to achieve ablation. The system and method can be further configured to control the delivery of radiofrequency energy inwardly from the tissue surface such that depth of tissue layers to which energy sufficient for ablation is delivered is controlled.

Controlling the fraction of the tissue surface target area that is ablated includes having some fraction of the tissue ablated, at least to some degree, and having some fraction of the surface within the target area emerge from the treatment substantially free of ablation. The ability to control the ratio of ablated and non-ablated surface can provide substantial benefit to the treatment. The ablational treatment, per embodiments of this invention, may be directed toward ablating vascular tissue, and having minimal effect or a recoverable or transient effect on the surrounding tissue. Thus, what is desired is a well-controlled and modulated ablation, where a varying degree of treatment effect can be provided, without substantially damaging the organ, or a particular layer of the organ. Stated in another way, it may be generally desirable for the health of the organ within which the targeted vascular tissue is located, and for the health of the individual as a whole, that some degree of normal functioning remain in the surrounding and intervening tissue after ablation.

With regard to the effect on vascular tissue of a method that includes fractional ablation of cells, including vascular cells, within a target area, to some extent a fractional ablation may be functionally as effective as a full ablation. Vascular cells, in particular the endothelial cells that form the vessels, grow in an arboreal manner. It is generally believed that isolated vasculature does not adjoin other portions of isolated vasculature. Thus, blood vessels that survive a fractional ablation procedure, but are left isolated from upstream and downstream connections, are marooned thereby and destined to be biologically resorbed. Thus, by the preceding considerations, it can be understood that fractional ablation of tissue within a target area, particularly a vascular target area, can effectively ablate acute or chronically bleeding vessels, but advantageously leave the tissue at large within the target area in a state of good health. Embodiments of the method thus include controlling the delivery of radiofrequency energy across the surface and into a depth of tissue within the target area, and thereby deliver sufficient radiofrequency energy to achieve ablation in one portion of the tissue target area and deliver insufficient radiofrequency energy to another portion of the surface to achieve ablation.

Further by way of an illustrative example as to what is desirable and being provided by the invention, the organ in which the ablation target area is located can be appreciated as populations of cells within the non-vascular tissue of the target area, which can function, based on their health, at a functional capacity at some low threshold of 20%, for example, when in poor condition, and at 100%, when in optimal condition. The object of the ablational treatment provided herein, within this example by analogy may not be to render the full population of cells to be dysfunctional and operating at 50% capacity. The object of the treatment may be to have some fraction of the cells within the population, post-ablational treatment, to remain fully functional, operating at about 100% capacity, and to have some remaining fraction operating at a range of lower capacity.

Controlling the fraction of the tissue surface target area that is ablated, per embodiments of the invention, is provided by various exemplary approaches: for example, by (1) the physical configuration of electrode pattern spacing in a comparatively non-dense electrode pattern, and by (2) the fractional operation of a comparatively dense electrode array, in a billboard-like manner. Generally, creating a fractional ablation by physical configuration of the electrode pattern includes configuring the electrode pattern such that some of the spacing between electrodes is sufficiently close that the conveyance of a given level of energy between the electrodes sufficient to ablate tissue is allowed, and other spacing between electrodes is not sufficiently close enough to allow conveyance of the level of energy sufficient to ablate. Embodiments of exemplary electrode patterns that illustrate this approach to creating fractional ablation are described below, and depicted in FIGS. 48-55. The creation of an ablation pattern by activating a subset of electrodes represents an operation of the inventive system and method which is similar to the described above, wherein an ablational structure with a fully circumferential pattern of electrodes can be operated in a manner such that only a radial fraction of the electrodes are operated.

The ablation system of the invention includes an electrode pattern with a plurality of electrodes and a longitudinal support member supporting the electrode pattern, as described in numerous embodiments herein. Energy is delivered to the electrodes from a generator, and the operation of the generator is controlled by a computer-controller in communication with the generator, the computer controller controlling the operating parameters of the electrodes. The computer controller has the capability of directing the generator to deliver energy to all the electrodes or to a subset of the electrodes. The controller further has the ability to control the timing of energy delivery such that electrodes may be activated simultaneously, or in subsets, non-simultaneously. Further, as described elsewhere, the electrodes may be operated in a monopolar mode, in a bipolar mode, or in a multiplexing mode. These various operating approaches, particularly by way of activating subsets of electrodes within patterns, allow the formation of patterns that, when the pattern is in therapeutic contact with a target surface, can ablate a portion of tissue in the target area, and leave a portion of the tissue in the target area non-ablated.

Generally, creating a fractional ablation by an operational approach with a comparatively dense electrode array includes operating the electrode pattern such that the energy delivered between some of the electrodes is sufficient to ablate, whereas energy sufficient to ablate is not delivered between some of the electrodes. Embodiments of exemplary electrode patterns that illustrate this approach to creating fractional ablation are described below, and depicted in FIGS. 48-55.

Another aspect of controlling the fraction of tissue ablation, per embodiments of the invention, relates to controlling the depth of ablation into tissue layers within the target area. Energy is delivered inwardly from the surface, thus with modulated increases in energy delivery, the level of ablation can be controlled such that, for example, the ablated tissue may consist only of tissue in the epithelial layer, or it may consist of tissue in the epithelial layer and the lamina propria layers, or it may consist of tissue in the epithelial, lamina propria and muscularis mucosal layers, or it may consist of tissue in the epithelial, lamina propria, muscularis mucosa, and submucosal layers, or it may consist of tissue in the epithelial layer, the lamina propria, the muscularis mucosae, the submucosa, and the muscularis propria layers. In no instance is ablational energy delivered to the serosal layer of the site of acute or chronic gastrointestinal tract bleeding.

Figure 48A:
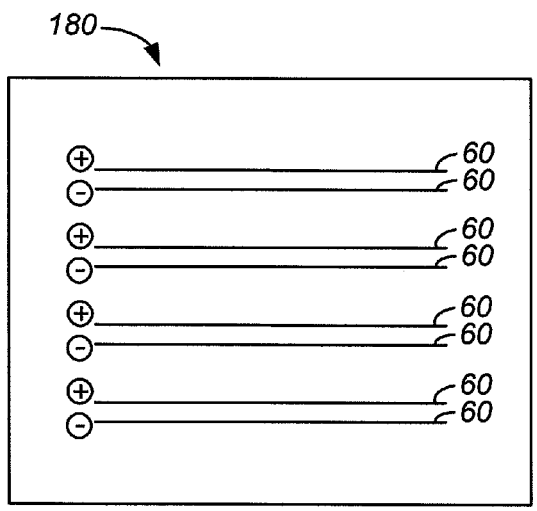
FIGS. 48A-48D show an electrode array with a striped pattern for a fractional ablation and the ablation patterns on tissue that can be made from such a pattern.
Figure 48B:
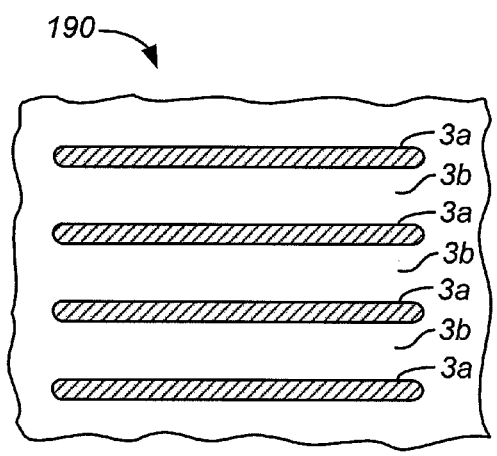
Figure 48C:
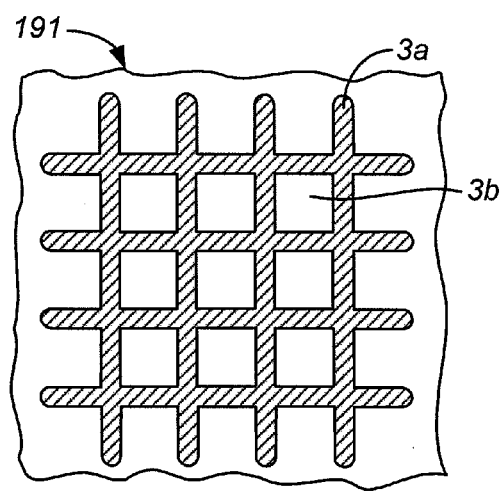
Figure 48D:
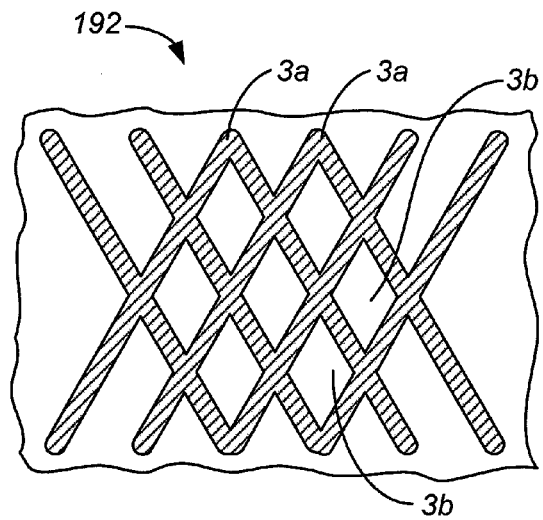
Figure 49A:
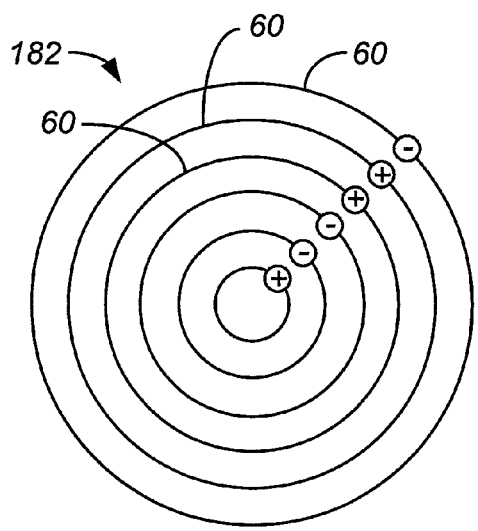
FIGS. 49A and 49B show an electrode array with a concentric-circle pattern for a fractional ablation and the ablation patterns on tissue that can be made from such a pattern.
Figure 50A:
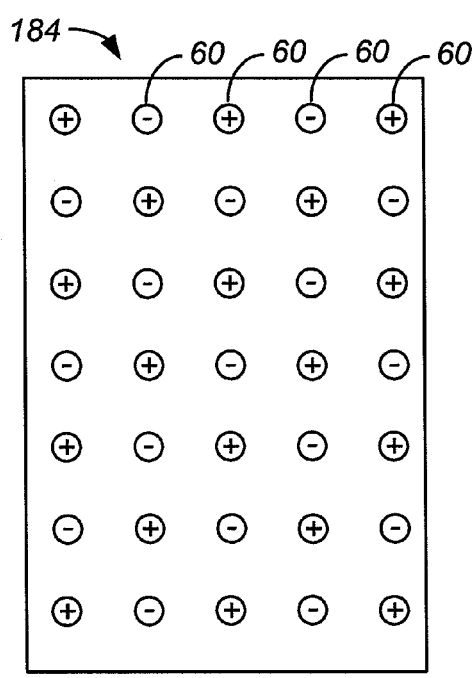
FIGS. 50A and 50B show an electrode array with a checkerboard pattern for a fractional ablation and the ablation patterns on tissue that can be made from such a pattern.

Embodiments of the invention include RF electrode array patterns that ablate a fraction of tissue within a given single ablational area, exemplary fractional arrays are shown in FIGS. 48A, 49A, and 50A. These fractional ablation electrode arrays may be applied, as above, to above to ablational structures that address a fully circumferential target area, or a structure that addresses any portion of a full circumference such as 90 degree radial surface, or a 180 degree radial surface. FIG. 48A shows a pattern 180 of linear electrodes 60 aligned in parallel as stripes on a support surface. The electrodes are spaced apart sufficiently such that when pressed against tissue in therapeutic contact, the burn left by distribution of energy through the electrodes results in a striped pattern 190 on the target tissue as seen in FIG. 48B corresponding to the electrode pattern, with there being stripes of burned or ablated tissue 3*a* that alternate with stripes of unburned, or substantially unaffected tissue 3*b*. In some embodiments of the method, particularly in ablation structures that address a target area of less than 360 radial degrees, such as a target surface that is about 180 degrees, or more particularly about 90 degrees of the inner circumference of a lumen, the ablation may be repeated with the ablational structure positioned at a different angle. FIG. 48C, for example, depicts a tissue burn pattern 191 created by a first ablational event followed by a second ablational event after the ablational structure is laterally rotated by about 90 degrees. FIG. 48D, for another example, depicts a tissue burn pattern 192 created by a first ablational event followed by a second ablational event after the ablational structure is laterally rotated by about 45 degrees.

The effect of an ability to ablate a tissue surface in this manner adds another level of fine control over tissue ablation, beyond such parameters as total energy distributed, and depth of tissue ablation. The level of control provided by fractional ablation, and especially when coupled with repeat ablational events as described above in FIGS. 48C and 48D, is to modulate the surface area-distributed fraction of tissue that is ablated to whatever degree the local maximal ablation level may be. The fractional ablation provided by such fractional electrode pattern may be particularly advantageous when the effects of ablation are not intended to be absolute or complete, but instead a functional compromise of tissue, or of cells within the tissue is desired. In some therapeutic examples, thus, a desirable result could be a partial reduction in overall function of a target area, rather than a total loss of overall function. In a fractional ablation of a target area in the wall of a site of acute or chronic gastrointestinal tract bleeding, for example, a desirable result may be the transient compromise of non-vascular tissue. In an ablation pattern that includes a burned area 3*a* and an unburned area 3*b*, it can be understood that cells from the unburned area could give rise to cells that would migrate or repopulate the denuded area within the burned area 3*b*.

Figure 49B:
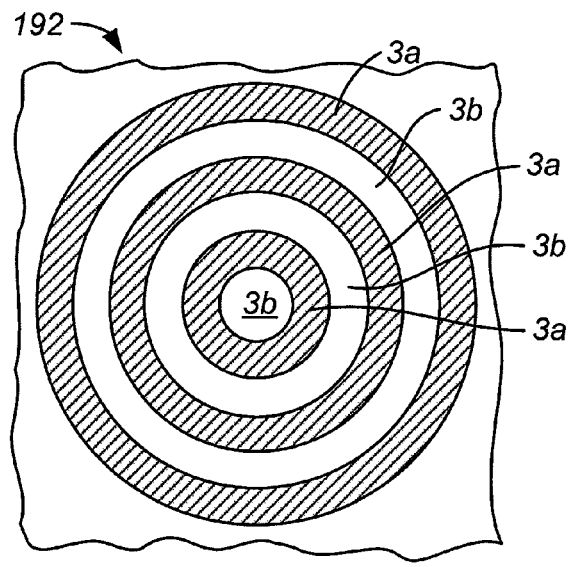
Figure 50B:
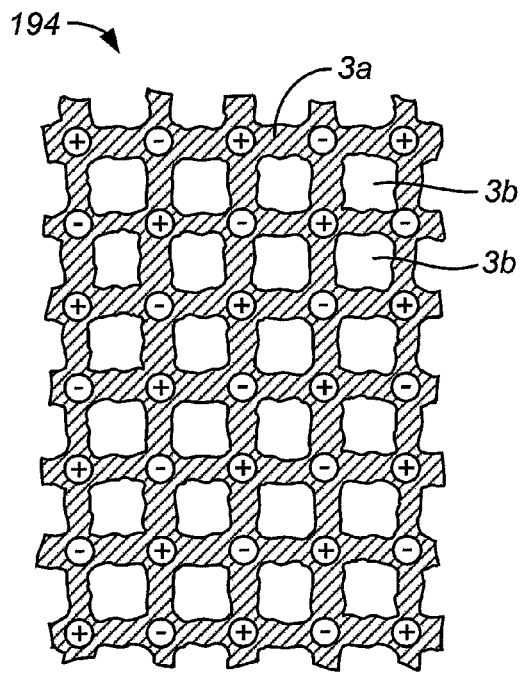

FIGS. 49A and 50A depict other examples of a fractionally-ablating electrode pattern on an ablation structure, and FIGS. 49B and 50B show the respective fractional burn patterns on tissue that have been treated with these electrode patterns. In FIG. 49A a pattern of concentric circles 182 is formed by wire electrodes that (from the center and moving outward) form a +−−++− pattern. When activated, the tissue between +− electrodes is burned, and the tissue between ++ electrode pairs or −− electrode pairs is not burned. Thus, the concentric pattern 192 of FIG. 49B is formed. Embodiments of fractionally-ablating electrode patterns such as those in FIG. 49A need not include perfect circles, and the circles (imperfect circles or ovals) need not be perfectly concentric around a common center.

Similarly, FIG. 50A shows a checkerboard pattern 184 of + and − electrodes which when activated create a burn pattern 194 as seen in FIG. 50B. Tissue that lies between adjacent + and − electrodes is burned, while tissue that lies between adjacent ++ electrodes or −− electrode pairs remains unburned. FIG. 50B includes a representation of the location of the + and − electrodes from the ablation structure in order to clarify the relative positions of areas that are burned 3*a* and the areas that remain substantially unburned 3*b*.

Embodiments of the invention include RF electrode array patterns that ablate a fraction of tissue within a given single ablational area by virtue of operational approaches, whereby some electrodes of a pattern are activated, and some are not, during an ablational event visited upon a target area. Exemplary fractional arrays are shown in FIGS. 51A, 52A, 53A and 54A. These fractional ablation electrode arrays may be applied, as above, to ablational structures that address a fully circumferential target area, or a structure that addresses any portion of a full circumference such as, by way of example, a 90 degree radial surface, or a 180 degree radial surface.

Figure 51A:
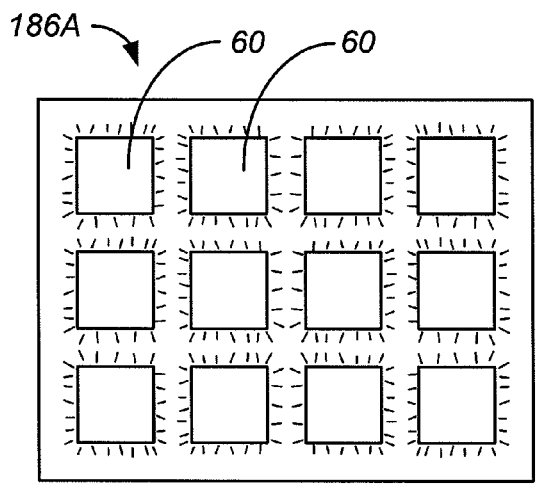
FIGS. 51A and 51B show an electrode array with a checkerboard pattern operating in a non-fractional manner and the ablation pattern on tissue that is made from such an operating pattern.
Figure 51B:
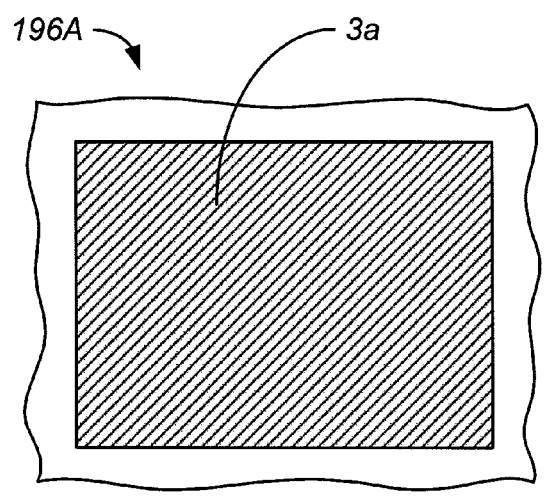
Figure 52A:
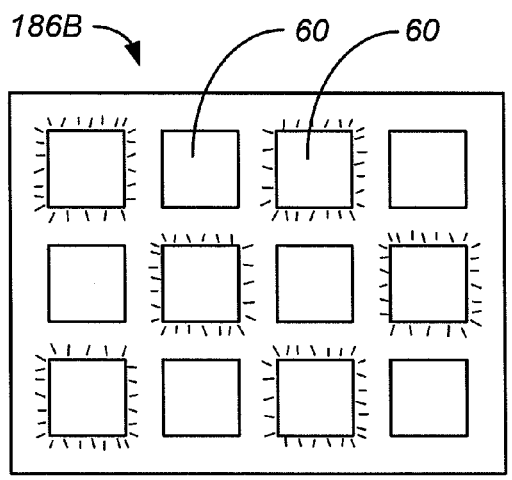
FIGS. 52A and 52B show an electrode array with a checkerboard pattern operating in a fractional manner and the ablation pattern on tissue that is made from such an operating pattern.
Figure 52B:
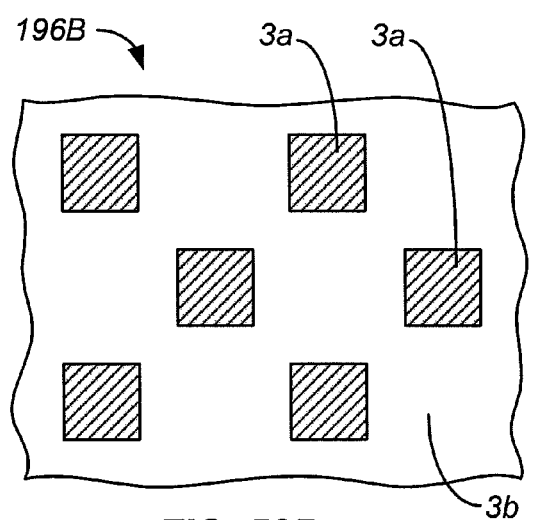

FIG. 51A shows a checkerboard electrode pattern during an ablational event during which all electrode squares of the operational pattern 186A are operating, as depicted by the sparkle lines surrounding each electrode. Operating the electrode pattern 186A in this manner produces an ablation pattern 196A, as seen in FIG. 51B, wherein the entire surface of tissue within the treatment area is ablated tissue 3a. FIG. 52A, on the other hand, shows a checkerboard electrode pattern during an ablational event during which only every-other electrode square of the operational pattern 186B is operating, as depicted by the sparkle lines surrounding each activated electrode. Operating the electrode pattern 186B in this manner produces an ablation pattern 196B, as seen in FIG. 52B, wherein a checkerboard fractionally ablated pattern with a dispersed pattern of ablated squares 3a of tissue 3a alternate with square areas of tissue 3b that are not ablated.

Figure 53A:
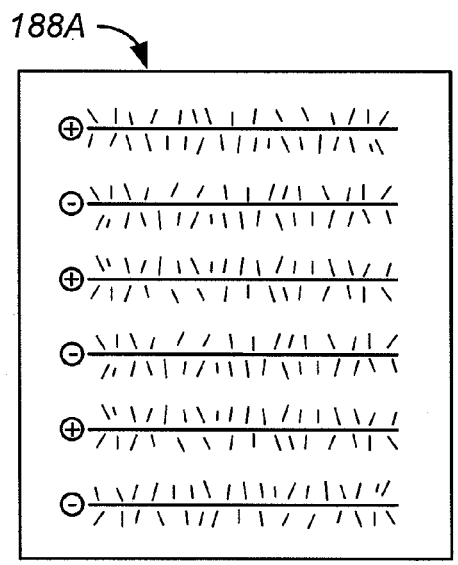
FIGS. 53A and 53B show an electrode array with a striped pattern of alternating positive and negative electrodes operating in a non-fractional manner and the ablation patterns on tissue that can be made from such an operating pattern.
Figure 53B:
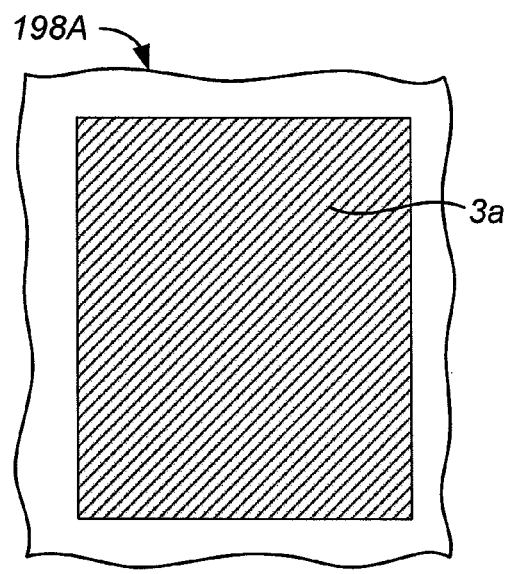

FIG. 53A shows a striped linear electrode pattern of alternating + and − electrodes during an ablational event during which all electrode squares of the operational pattern 188A are operating, as depicted by the sparkle lines surrounding each linear electrode. Operating the electrode pattern in this manner 188A produces an ablation pattern 198A, as seen in FIG. 53B, wherein the entire surface of tissue within the treatment area is ablated tissue 3a.

Figure 54A:
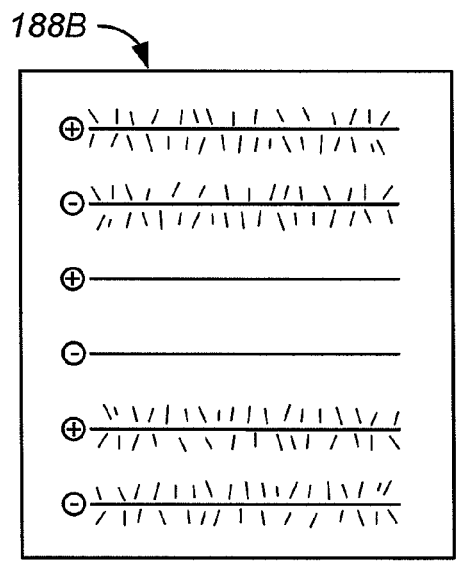
FIGS. 54A and 54B show an electrode array with a striped pattern of alternating positive and negative electrodes operating in a fractional manner and the ablation patterns on tissue that can be made from such an operating pattern.
Figure 54B:
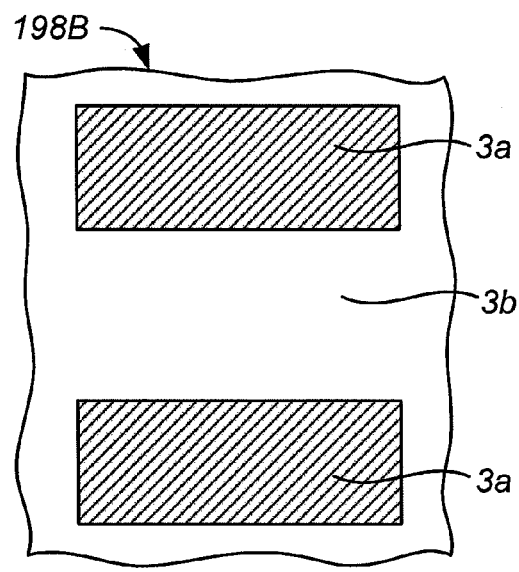

FIG. 54A, on the other hand, shows a striped linear electrode pattern 188B of alternating + and − electrodes during an ablational event during which alternate pairs of the linear electrode pairs are operating, as depicted by the sparkle lines surrounding the activated linear electrodes. Operating the electrode pattern in this manner 188B produces an ablation pattern 198B, as seen in FIG. 54B, wherein stripes of ablated tissue 3a within the treatment area alternate stripes of non-ablated tissue 3b.

Figure 55:
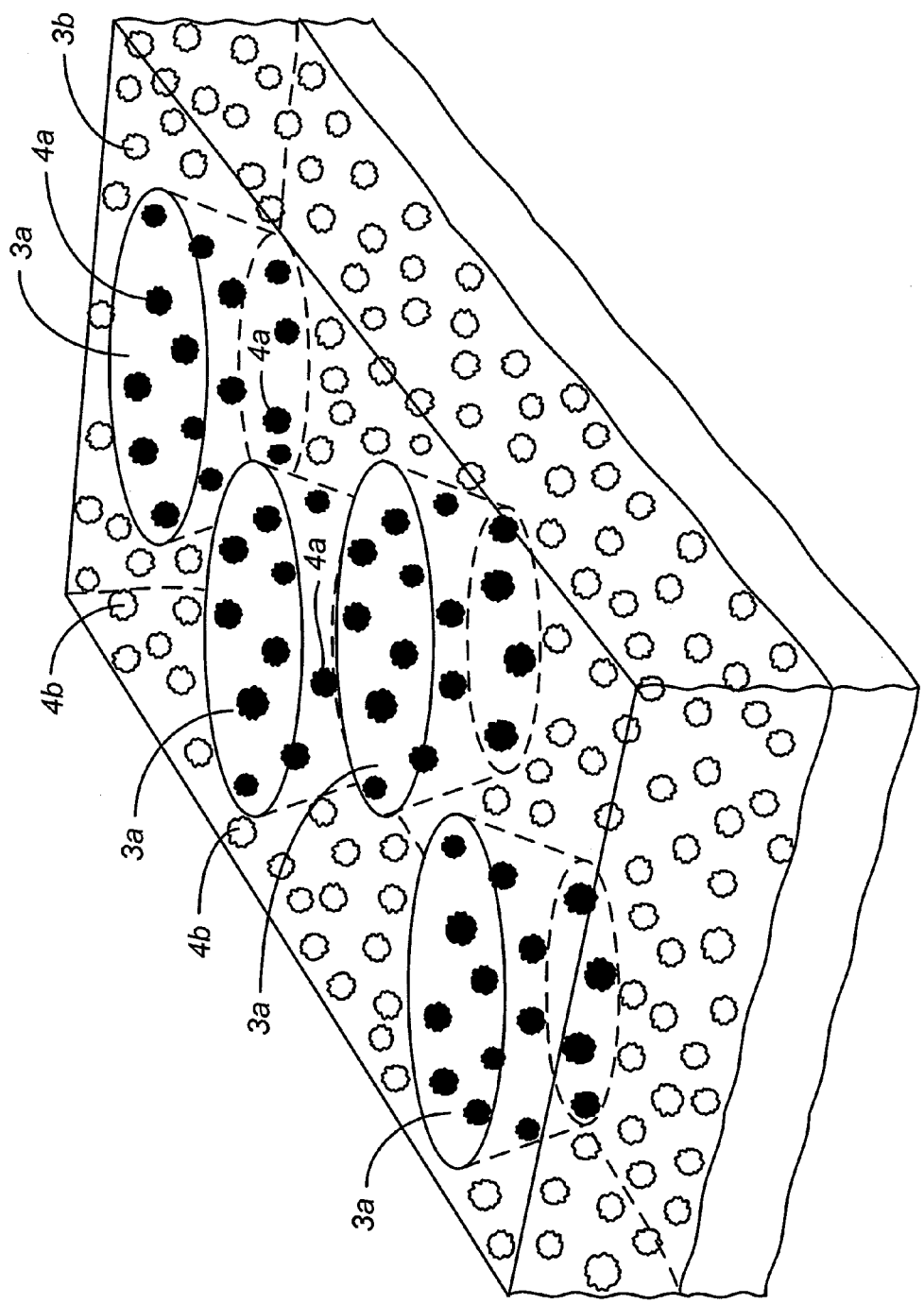
FIG. 55 shows a schematic rendering of a three-dimensional view of a target region of a radial portion of the gastrointestinal tract at a site of acute or chronic bleeding after it has been ablationally treated.

FIG. 55 is a schematic rendering of a three dimensional view of a target region of a radial portion of a site of acute or chronic gastrointestinal tract bleeding after it has been ablationally treated, per embodiments of the invention. Ablated regions 3a are rendered as regions distributed through the target area within a larger sea of non-ablated tissue 3b. These regions are depicted as being slightly conical in this schematic view, but in practice the ablated tissue region may be more cylindrical in shape. The regions 3a are of approximately the same depth, because of the control exerted over the depth of the ablation area into layers of the gastrointestinal wall, as described herein. With such control, the regions 3a can vary with respect of the layer to which they extend continuously from the upper surface where ablational energy has been applied. The conical regions are of approximately the same width or diameter, and distributed evenly throughout the tissue, because of the control over ablational surface area, as described herein. In this particular example, the therapeutic target is actually a particular type of cell 4b (open irregular spheres), for example, a nerve cell, or endocrine secretory cell; and these cells are distributed throughout the target area. The post-ablation therapeutic target cells 4a (dark irregular spheres) are those which happened to be included within the conical regions 3a that were ablated. The post-ablation cells 4a may be rendered dysfunctional to varying degree, they may be completely dysfunctional, they may be, merely by way of illustrative example, on the average, 50% functional by some measure, and there functionality may vary over a particular range. It should be particularly appreciated however, per embodiments of the invention, that the cells 4b, those not included in the ablated tissue cones, are fully functional.

Controlling the Ablation in Terms of the Tissue Depth of the Ablation Effect

In addition to controlling the surface area distribution of ablation, as may be accomplished by the use of fractional ablation electrodes as described above, or as controlled by the surface area of electrode dimensions, ablation can be controlled with regard to the depth of the ablation below the level of the tissue surface where the ablative structure makes therapeutic contact with the tissue. The energy delivery parameters appropriate for delivering ablation that is controlled with regard to depth in tissue may be determined experimentally. By way of example, an experimental set of exercises was performed on normal immature swine in order to understand the relationship between the electrical parameters of electrode activation and the resultant level of ablation in esophageal tissue. The data are shown in detail in U.S. application Ser. No. 10/370,645 of Ganz et al, filed on Feb. 19, 2003, and in the publication on Aug. 21, 2003, of that application, US 2003/0158550 A1, particularly in Tables 1-4 of that application. By an approach such as this, appropriate parameters for ablation of other tissues in the site of acute or chronic gastrointestinal tract bleeding tract may be determined. Such parameters as applied by ablational electrode patterns on an ablational structure with a 360 degree operating surface that is directed to esophageal tissue, by way of example, include 300 W delivered within 300 msec, with a tightly spaced with tightly spaced bi-polar electrode array (less than 250 microns). Ablation depth related to the energy density delivered with 8-12 J/cm2 results in complete removal of the epithelium. Such parameters as applied by electrode patterns on an ablation structure with an operating radial surface of about 90 degrees includes multiple narrow band electrodes spaced 250 microns wide, where the generator delivers very high power energy density at 40 W/cms to the tissue in an energy dosage of 12-15 J/cm2. In general, depth variances can be achieved via time of ablation, dosage, number of energy applications, and electrode spacing.

Figure 25:
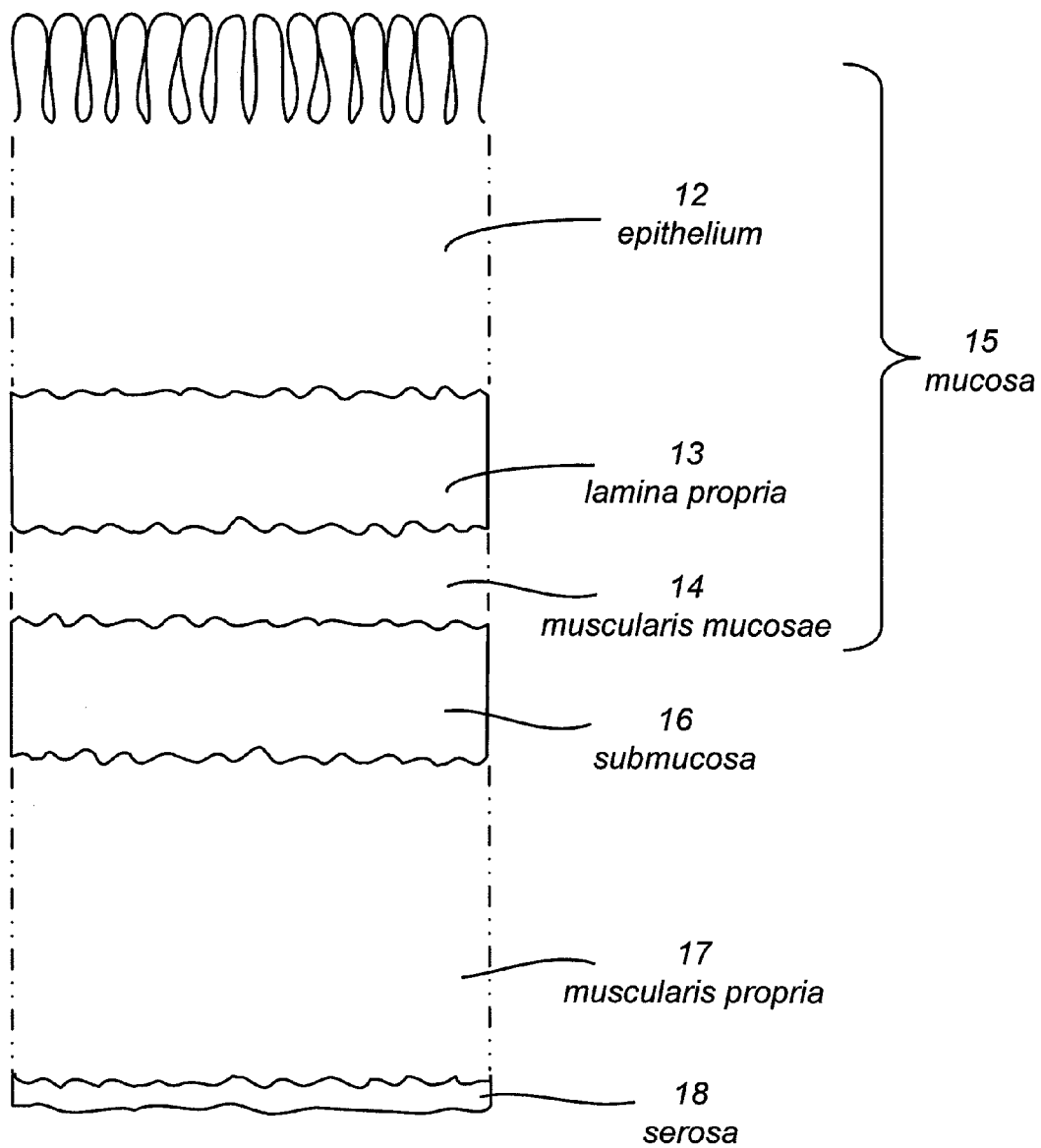
FIG. 25 is a schematic of view of a section through the wall of a portion of the gastrointestinal tract.

FIG. 25 provides a schematic representation of the histology of the gastrointestinal tract at a site of acute or chronic bleeding as it is found in various luminal organs such as the esophagus, stomach, pylorus, duodenum, and jejunum. The relative presence and depth and composition of the layers depicted in FIG. 25 vary from organ to organ, but the basic organization is similar. The layers of the a site of acute or chronic gastrointestinal tract bleeding will be described in their order from the innermost to the outermost layer facing the a site of acute or chronic gastrointestinal tract bleeding lumen; and as seen FIG. 25 and in terms of the direction from which an ablational structure would approach the tissue. The innermost layer can be referred to as the surface (epithelium), and succeeding layers can be understood as being below or beneath the "upper" layers. The innermost layer of a gastrointestinal tract at a site of acute or chronic bleeding, which is in direct contact with the nutrients and processed nutrients as they move through the gut is a layer of epithelium 12. This layer secretes mucous which protects the lumen from abrasion and against the corrosive effect of an acidic environment. Beneath the epithelium is a layer known as the lamina propria 13, and beneath that, a layer known as the muscularis mucosae 14. The epithelium 12, the lamina propria 13, and the muscularis mucosae 14 collectively constitute the mucosa 15.

Below the mucosal layer 15 is the submucosa 16, which forms a discrete boundary between the muscosal layer 15 above, and the muscularis propria 17 below. The muscularis propria 17 includes various distinct layers of smooth muscle that enwrap the organ, in various orientations, including oblique, circular, and the longitudinal layers. Enwrapping the muscularis propria 17 is the serosa 18, which marks the outer boundary of the organ.

The entirety of gastrointestinal tract tract wall is highly vascular and innervated. The mucosal layer is also rich in glands and cells that secrete contents into the lumen and secrete hormones into the bloodstream. All of these cells, including vasculature, exocrine cells, endocrine cell, and nerve cells are potential targets for ablation when ablational energy is directed toward the region in which they reside. As a result of receiving energy, cells may be killed or scarred to an extent that they are no longer functional, or they may be partially damaged, leaving some level of function. Additionally, it should be understood that these cells all exist in populations, and a partial ablation may manifest in a statistical distribution of damage, in which some cells of the population are eliminated or damaged beyond redemption, and some cells may remain substantially unaffected, and fully functional. In such partial or fractional ablation events, it can be understood that the remnant level of function following therapeutic ablation may include a range of function and dysfunction.

As provided by embodiments of the invention, the ablation applied to the gastrointestinal tract at a site of acute or chronic bleeding wall tissue may be depth-controlled, such that only the epithelium 12, or only a portion of the mucosal layer is ablated, leaving the deeper layers substantially unaffected. In other embodiments, the ablated tissue may commence at the epithelium yet extend deeper into the submucosa and possibly the muscularis propria, as necessary to achieve the desired therapeutic effect.

Device and Method for Partially-Circumferential Ablation

Figure 24:
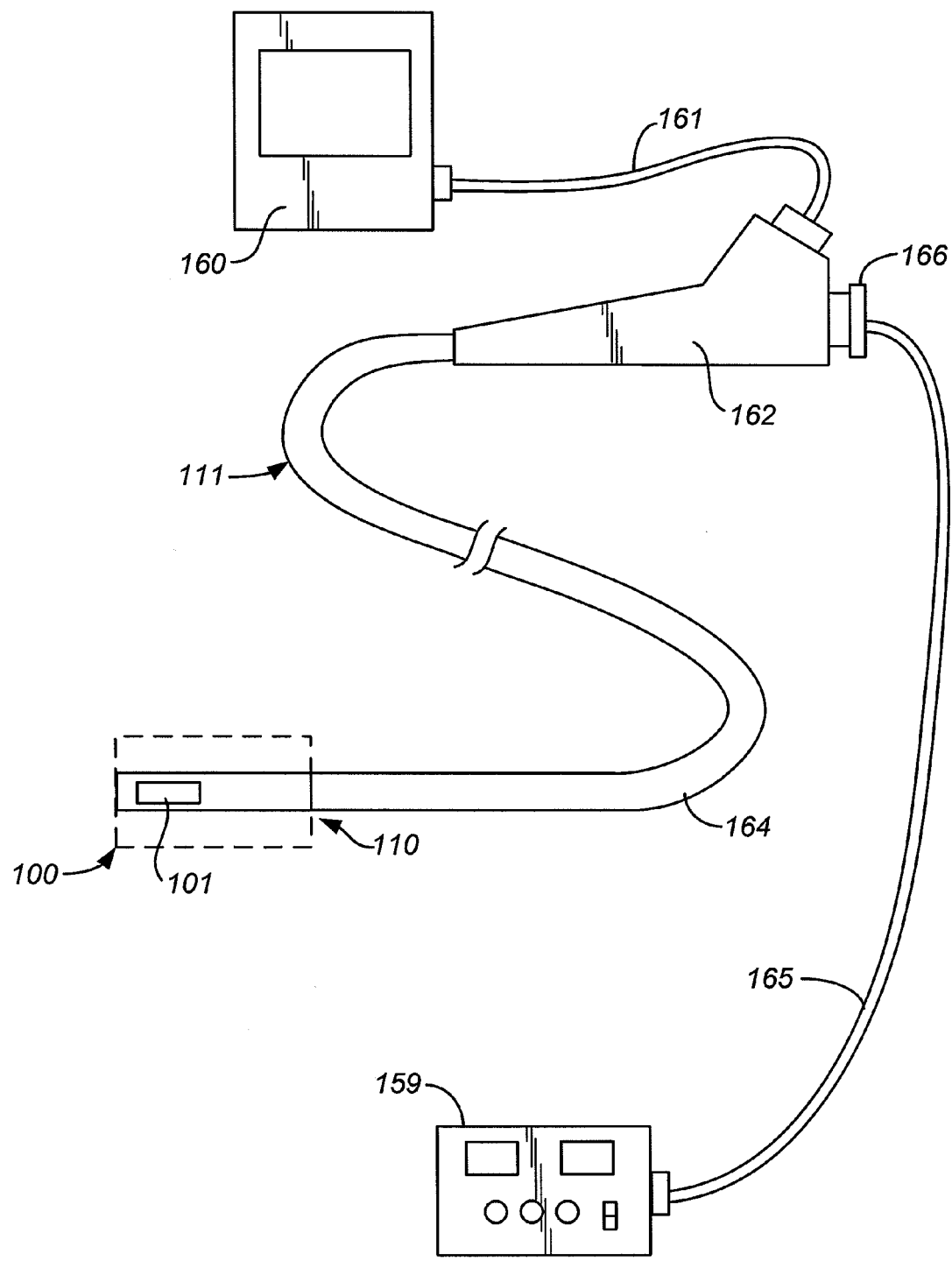
FIG. 24 is an illustration of the ablation device of the invention combined with an endoscope system.

One embodiment of a method of ablating tissue in the gastrointestinal tract at a site of acute or chronic bleeding tract includes the use of an ablation device with an ablation structure supported by conventional endoscopes 111, as illustrated in FIG. 24. As described herein, more particularly, the tissue targeted for ablation by embodiments of an ablation device and methods therefore is on the wall of the gastrointestinal tract at a site of acute or chronic bleeding. An example of one commercially available conventional endoscope 111 is the Olympus "gastrovideoscope" model number GIF-Q160. While the specific construction of particular commercially available endoscopes may vary, as shown in FIG. 24, most endoscopes include a shaft 164 having a steerable distal end 110 and a hub or handle 162 which includes a visual channel 161 for connecting to a video screen 160 and a port 166 providing access to an inner working channel within the shaft 164. Dials, levers, or other mechanisms (not shown) will usually be provided on the handle 162 to allow an operator to selectively steer the distal end 110 of the endoscope 111 as is well known in the endoscopic arts. In accordance with the present invention, an ablation device, including an ablation structure is advanced into the gastrointestinal tract to a site of acute or chronic bleeding tract while supported at the distal end of an endoscope. The ablation structure is deflectable toward a tissue surface and the ablation structure is activated to ablate the tissue surface. Within the gastrointestinal tract at a site of acute or chronic bleeding tract, variously sized tissue surface sites can selectively be ablated using the device. As will be further described, the ablational structure of embodiments described in this section do not circumscribe a full 360 degrees, but rather circumscribe a fraction of 360 degrees, as will be described further below.

In general, in one aspect a method of ablating tissue in the gastrointestinal tract at a site of acute or chronic bleeding tract is provided. The method includes advancing an ablation structure into the gastrointestinal tract at a site of acute or chronic bleeding tract while supporting the ablation structure with an endoscope. In some embodiments, advancing the structure into a site of acute or chronic gastrointestinal tract bleeding may be sufficient to place the ablational structure of the device into close enough proximity in order to achieve therapeutic contact. In other embodiments, a subsequent step may be undertaken in order to achieve an appropriate level of therapeutic contact. This optional step will be generally be understood as moving the ablation structure toward the target site. The method thus may further include moving at least part of the ablation structure with respect to the endoscope and toward a tissue surface; and activating the ablation structure to ablate the tissue surface. Moving at least part of the ablation structure with respect to the endoscope can include movement toward, away from or along the endoscope. Moving the ablational structure toward a target tissue surface may be performed by structures in ways particular to the structure. For example, the structure can be moved by inflating a balloon member, expanding a deflection member, or moving a deflection member. The function of such movement is to establish a therapeutically effective contact between the ablational structure and the target site. A therapeutically effective contact includes the contact being substantial and uniform such that the highly controlled electrical parameters of radiant emission from the electrode result in similarly highly controlled tissue ablation. Some embodiments of the invention further include structure and method for locking or securing such a therapeutically effective contact once established. Thus, some embodiments include a position locking step that, for example, uses suction to secure the connection between the ablation structure and the tissue site.

Figure 9:
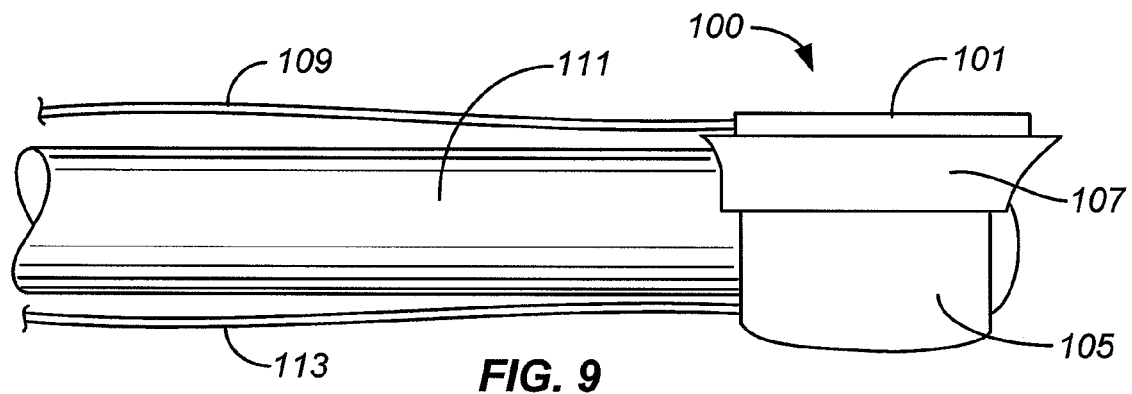
FIG. 9 is a view of the ablation device of the invention with a partially circumferential operating radius.
Figure 10:
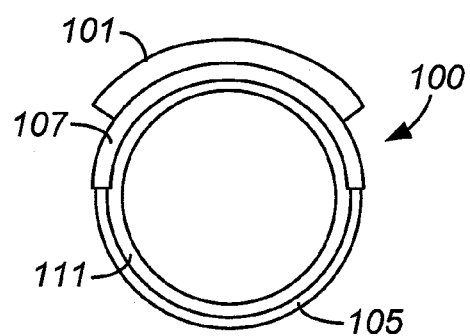
FIG. 10 is an end view of the ablation device embodiment of FIG. 9.
Figure 11:
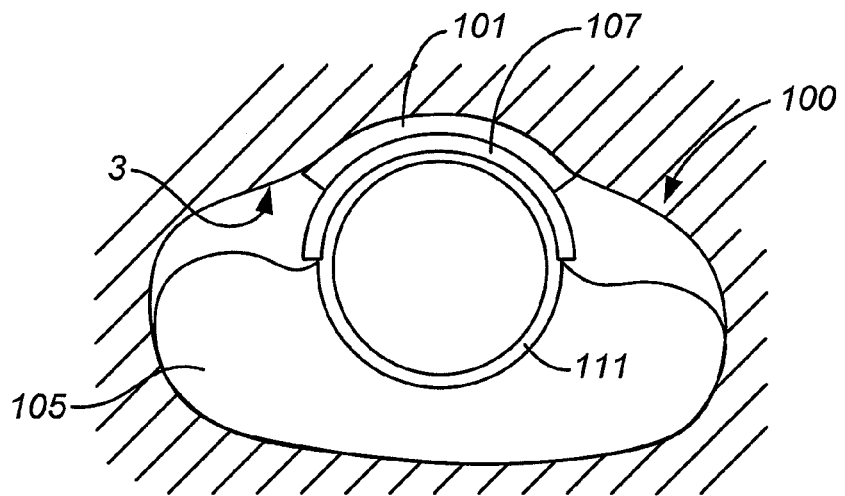
FIG. 11 is an end view of the device of FIG. 9 in an expanded configuration.

As shown in FIGS. 9, 10, 11, and 26, in one aspect a method of ablating tissue in the gastrointestinal tract at a site of acute or chronic bleeding includes an ablation device 100 for ablating a tissue surface 3, wherein the device 100 includes an ablating structure, for example, an ablation structure 101 supported by an endoscope 111. The method includes ablating tissue in the wall of a luminal organ of the gastrointestinal tract at a site of acute or chronic bleeding tract by the steps of (1) advancing the ablation structure 101 into the luminal organ; (2) deflecting the ablation structure 101 toward a tissue surface 3; and (3) activating the ablation structure to ablate the tissue surface 3. As shown in FIG. 9, the device 100 can additionally include a housing 107, electrical connections 109, an inflation line 113 and an inflation member or balloon 105.

The ablation structure 101, in one embodiment is an electrode structure configured and arranged to deliver energy comprising radiofrequency energy to the mucosal layer of the wall of the organ at a site of acute or chronic gastrointestinal tract bleeding tract. It is envisioned that such an ablation structure 101 can include a plurality of electrodes. For example, two or more electrodes may be part of an ablation structure. The energy may be delivered at appropriate levels to accomplish ablation of mucosal or submucosal level tissue, or alternatively to cause therapeutic injury to these tissues, while substantially preserving muscularis tissue. The term "ablation" as used herein generally refers to thermal damage to the tissue causing any of loss of function that is characteristic of the tissue, or tissue necrosis. Thermal damage can be achieved through heating tissue or cooling tissue (i.e. freezing). In some embodiments ablation is designed to be a partial ablation.

Although radiofrequency energy, as provided by embodiments of the invention, is one particular form of energy for ablation, other embodiments may utilize other energy forms including, for example, microwave energy, or photonic or radiant sources such as infrared or ultraviolet light, the latter possibly in combination with improved sensitizing agents. Photonic sources can include semiconductor emitters, lasers, and other such sources. Light energy may be either collimated or non-collimated. Other embodiments of this invention may utilize heatable fluids, or, alternatively, a cooling medium, including such non-limiting examples as liquid nitrogen, Freon™, non-CFC refrigerants, $CO_2$ or $N_2O$ as an ablation energy medium. For ablations using hot or cold fluids or gases, the ablation system may include an apparatus to circulate the heating/cool medium from outside the patient to the heating/cooling balloon or other element and then back outside the patient again. Mechanisms for circulating media in cryosurgical probes are well known in the ablation arts. For example, and incorporated by reference herein, suitable circulating mechanisms are disclosed in U.S. Pat. No. 6,182,666 to Dobak, U.S. Pat. No. 6,193,644 to Dobak, U.S. Pat. No. 6,237,355 to Li, and U.S. Pat. No. 6,572,610 to Kovalcheck.

In a particular embodiment, the energy delivered to the wall of a luminal organ at a site of acute or chronic gastrointestinal tract bleeding tract comprises radiofrequency energy that can be delivered from the energy delivery device 100. Radiofrequency energy can be delivered in a number of ways. Typically, the radiofrequency energy will be delivered in a bipolar fashion from a bipolar array of electrodes positioned on the ablation structure 101, in some cases on an expandable structure, such as a balloon, frame, cage, or the like, which can expand and deploy the electrodes directly against or immediately adjacent to the mucosal tissue so as to establish a controlled level of therapeutic contact between the electrodes and the target tissue (e.g., through direct contact or through a dielectric membrane or other layer). Alternatively, the electrode structure may include a monopolar electrode structure energized by a radiofrequency power supply in combination with a return electrode typically positioned on the patient's skin, for example, on the small of the back. In any case, the radiofrequency energy is typically delivered at a high energy flux over a very short period of time in order to injure or ablate only the mucosal or submucosal levels of tissue without substantially heating or otherwise damaging the muscularis tissue. In embodiments where the ablation structure includes a plurality of electrodes, one or more of the electrodes can be bipolar or monopolar, and some embodiments include combinations of bipolar and monopolar electrodes.

The ablation structure 101 can be arranged and configured in any of a number ways with regard to shape and size. Typically, the array has an area in the range from about 0.5 $cm^2$ to about 9.0 $cm^2$. Typical shapes would include rectangular, circular or oval. In one embodiment, the ablation structure 101 has an area of about 2.5 $cm^2$. In another embodiment, the ablation structure 101 has an area of about 4 $cm^2$ and dimensions of about 2 cm. by 2 cm.

The housing 107 of the ablation device 100 is arranged and configured to support the ablation structure 101. The housing 107 can be made of any suitable material for withstanding the high energy flux produced by the ablation structure 101. As shown in FIGS. 9-14, 17, 18, 21, and 22, in one embodiment, the housing 107 is sandwiched between the ablation structure 101 and an endoscope 111 when the ablation device 100 is supported by an endoscope 111. One end of the ablation structure 101 can be further away from the endoscope than the other end to improve ease of contact with the targeted tissue (not shown). For example, to ensure the proximal end of the ablation structure 101 makes contact with the targeted tissue, the proximal end of the electrode may be supported by a tapered housing member 107.

The electrical connections 109 of the ablation device connect the ablation structure 101 to a power source. The electrical connections 109 can include a single wire or plurality of wires as needed to provide controlled energy delivery through the ablation structure 101. In one embodiment, the electrical connections 109 include low electrical loss wires such as litz wire.

The inflation line 113 is arranged and configured to transport an expansion medium, typically a suitable fluid or gas, to and from the inflation member. In one embodiment, the inflation line is a flexible tube. The inflation line 113 can be made of polymer or co-polymers, such as the non-limiting examples of polyimide, polyurethane, polyethylene terephthalate (PET), or polyamides (nylon). The inflation member 105 is designed to deflect the ablation device 100 in relation to a target tissue surface 3. The inflation member 105 can be reversibly expanded to an increased profile.

Figure 31:
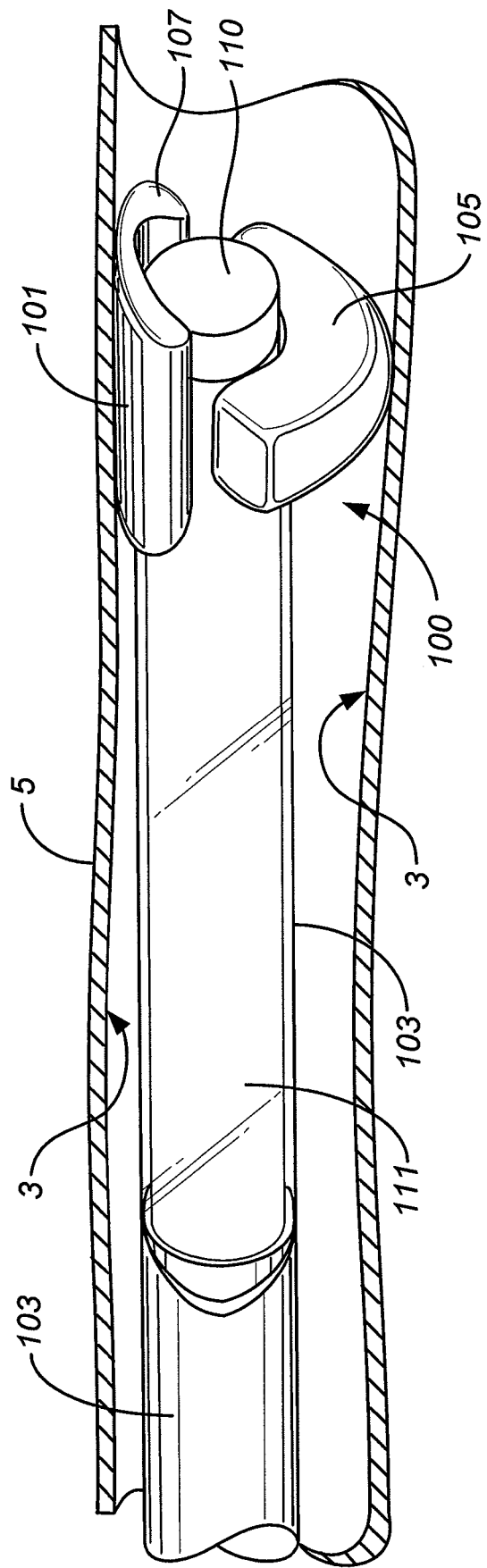
FIG. 31 is an illustration of the ablation device of FIG. 30 positioned within an esophagus.
Figure 42:
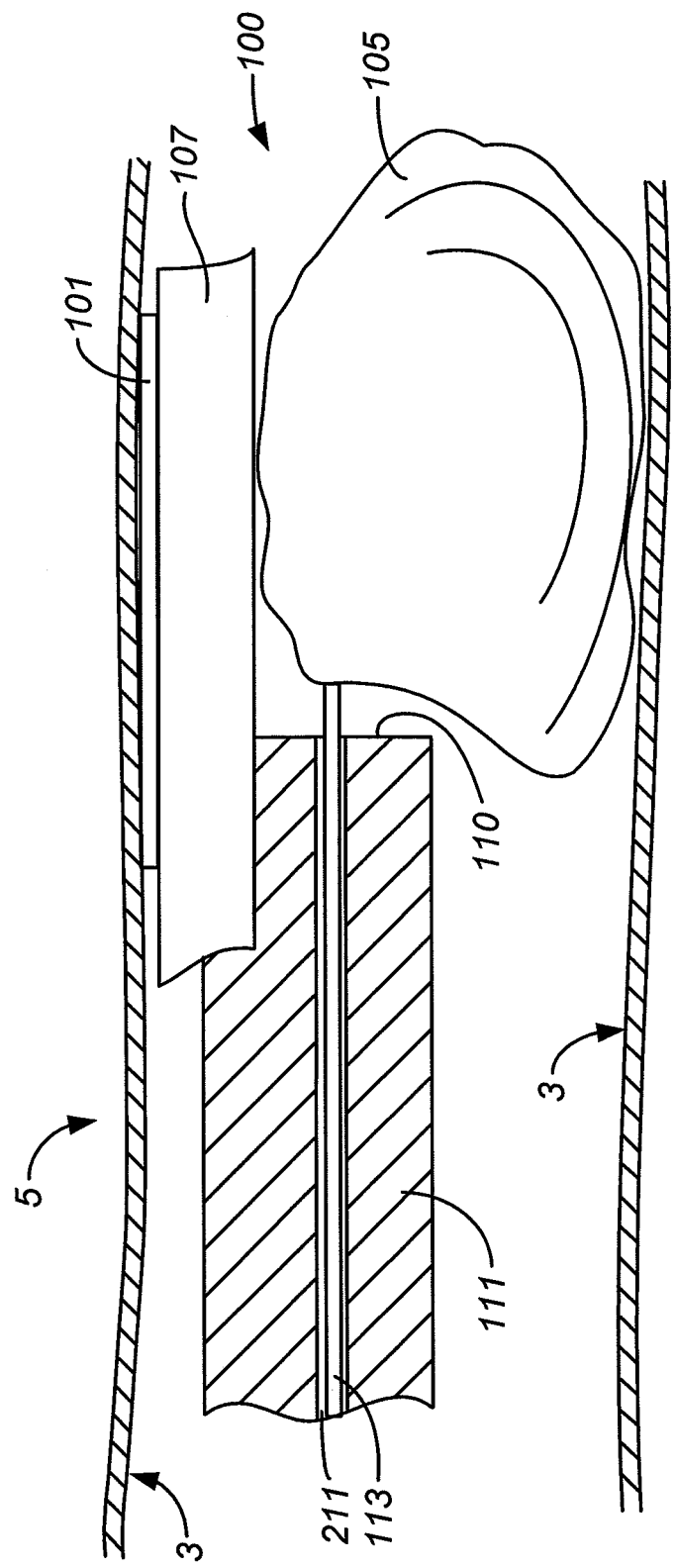
FIG. 42 is an illustration showing a cross sectional view of the ablation device of the invention positioned within a lumen at a site of acute or chronic gastrointestinal tract bleeding.

In one embodiment, the inflation member 105 additionally serves as an attachment site for support of the ablation device 100 by an endoscope 111. As shown in FIGS. 9-14, 17, 18, 21 and 22, the inflation member 105 can be deployed from a low profile configuration or arrangement (see FIGS. 10, and 20) to an increased profile configuration or arrangement (see FIGS. 11-14, 17-19) using the expansion medium. In preparation for ablation, when the inflation member 105 is sufficiently inflated, deflection of the ablation device 100 in relation to a tissue surface 3 can be achieved. As shown in FIGS. 11, 31, 42, and 44, in one embodiment, deflection of the ablation device 100 results in a therapeutic level of contact, i.e., a substantially direct, uniform, and sustainable contact between the ablation structure 101 of the device 100 and the target tissue surface 3. For example, as shown in FIGS. 31, 42, and 44, when the inflation member 105 is sufficiently inflated, the resulting expanded profile of the inflation member 105, which contacts the tissue surface 3, results in contact by deflection between the tissue surface 3 of the inner wall 5 of a luminal organ a gastrointestinal tract at a site of acute or chronic bleeding tract and the ablation structure 100. In these embodiments, suction can be applied in combination with the inflation member 105 to achieve contact between the ablation structure 101 and the tissue surface 3. Suction can be achieved through the endoscope 111 or through the ablation device 100 to aid in collapsing the targeted tissue surface 3 around the ablation structure 101.

In various embodiments, the inflation member 105 may be compliant, non-compliant or semi-compliant. The inflation member 105 can be made of a thin, flexible, bladder made of a material such as a polymer, as by way of non-limiting examples, polyimide, polyurethane, or polyethylene terephthalate (PET). In one embodiment, the inflation member is a balloon. Inflation of the inflation member 105 can be achieved through the inflation line 113 using, for example, controlled delivery of fluid or gas expansion medium. The expansion medium can include a compressible gaseous medium such as air. The expansion medium may alternatively comprise an incompressible fluid medium, such as water or a saline solution.

Figure 12:
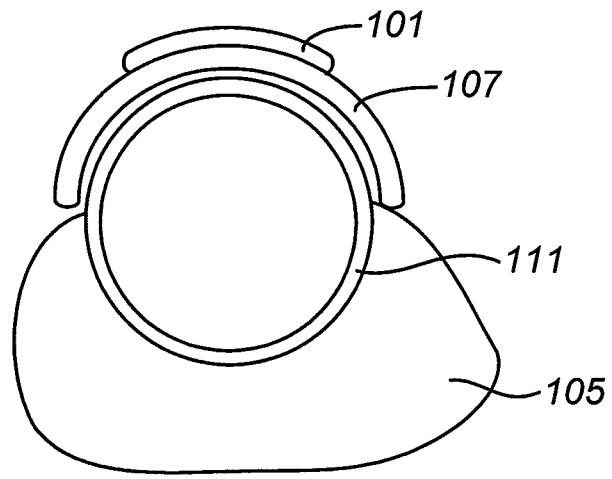
FIGS. 12, 13, and 14 are end views of the device of FIG. 9 in alternative expanded configurations.
Figure 13:
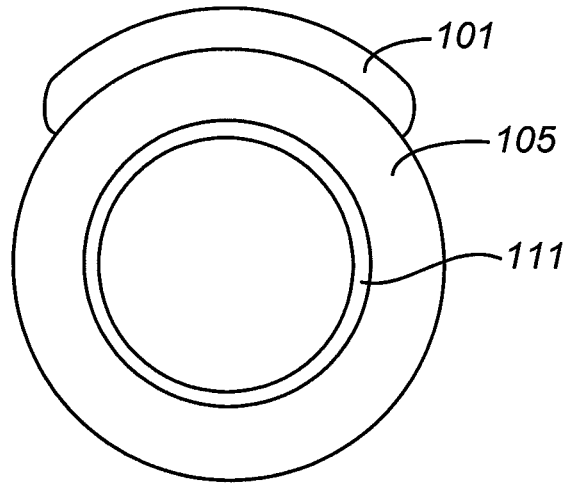
Figure 14:
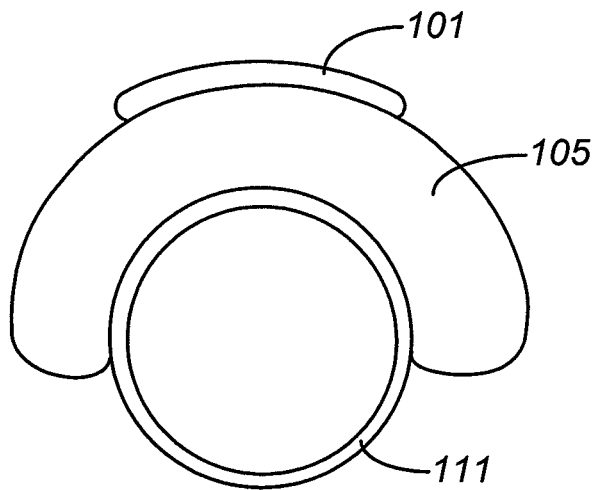
Figure 17:
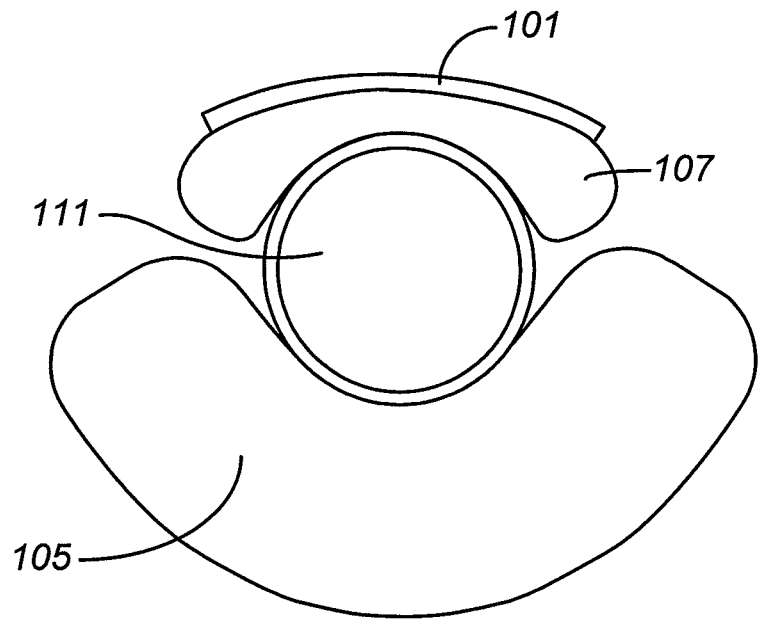
FIGS. 17 and 18 are end views of the device in an expanded configuration.
Figure 18:
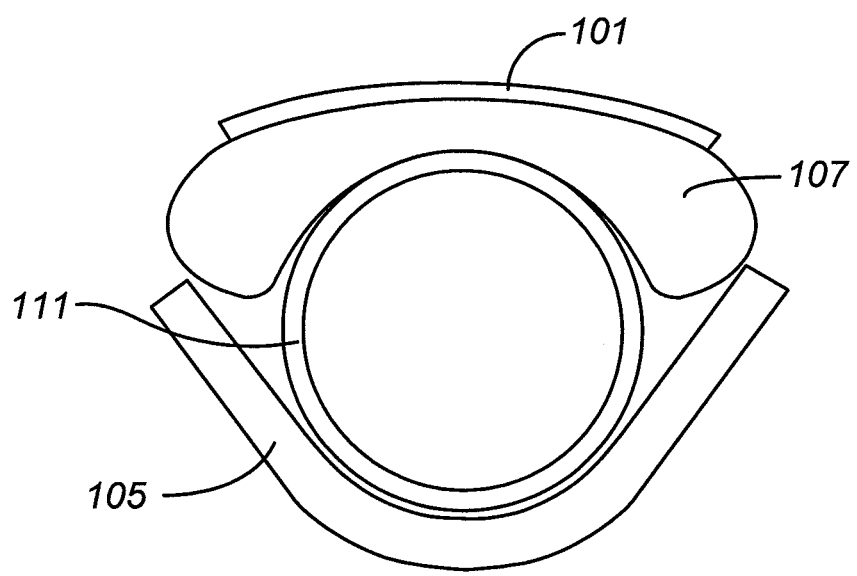

As shown in FIGS. 12, 13, and 14, the inflation member 105 can be configured and arranged in a variety of ways to facilitate deflection of the ablation device 100 in relation to a tissue surface 3. For example, as shown in FIG. 12, the inflation member 105 can be eccentrically positioned in relation to the supporting endoscope 111 as well as the housing 107 and the ablation structure 101. Alternatively, as shown in FIG. 13, the inflation member 105 can be positioned concentrically in relation to the supporting endoscope 111 and the ablation structure 101 can be attached to the inflation member 105 distally from the endoscope 111. In another embodiment, as shown in FIG. 12, the inflation member 105 can be positioned between the supporting endoscope 111 and the ablation structure 101. The ablation structure 101 shown in FIGS. 12-14 can cover a range of circumferential span of the endoscope 111 spanning, for example, from about 5 to 360 degrees when inflation member 105 is deployed.

One method of ablating tissue in a luminal organ of the gastrointestinal tract at a site of acute or chronic bleeding tract can include a first step of advancing an ablation structure 101, to a site of acute or chronic gastrointestinal tract bleeding. In a second step, the ablation structure 101 is supported with an endoscope 111 at the site of acute or chronic gastrointestinal tract bleeding. In a third step, the ablation structure 101 is deflected toward a tissue surface 3. In a fourth step, energy can be applied to the ablation structure 101 to ablate the tissue surface 3.

In another method, the step of advancing an endoscope-supported ablation structure 101 can include advancing the endoscope 111 into a luminal organ at a site of acute or chronic gastrointestinal tract bleeding and advancing the ablation structure 101 over the endoscope 111. For example, the endoscope 111 can be positioned relative to an ablation target tissue surface 3 after which the ablation structure 101 can be advanced over the outside of the endoscope 111 for ablating the target tissue surface 3.

In a further method, the step of supporting the ablation structure 101 with an endoscope 111 includes inserting the endoscope 111 into the ablation structure 101 (see for example, FIGS. 1A-2B). In a related method, the ablation structure 101 is supported by a sheath 103 (see FIGS. 26-28, 30, 31, 32 and 37) and the step of inserting the endoscope 111 into the ablation structure 101 includes inserting the endoscope 111 into the sheath 103. In a further related method, the step of inserting the endoscope 111 into the sheath 103 includes creating an opening in the sheath 103 (not shown).

In a particular method, a distal portion of a sheath 103 having a smaller outer diameter than a proximal portion of the sheath 103, is adapted to be expanded when an endoscope 111 is inserted into it.

In another method, the step of advancing the ablation structure 101 into the gastrointestinal tract at a site of acute or chronic bleeding includes advancing the ablation structure 101 through a channel of the endoscope 111 from either the endoscopes proximal or distal end (as discussed below for FIGS. 34A, 35A and 36A). In yet another method, the step of supporting the ablation structure 101 comprises supporting the ablation structure 101 with a channel of the endoscope (see as discussed below for FIGS. 34A, 35A, 36A, 37-39). In a further method, a deflection structure or deflection member 150 is advanced through a channel of the endoscope 111 and the step of deflecting the ablation structure 101 toward a tissue surface 3 includes deflecting the ablation structure 101 with the deflection structure or deflection member 150.

As illustrated in FIGS. 34A, 35A, and 36A, variously adapted and configured ablation structures 101 can fit within and be conveyed through an endoscope internal working channel 211. In each case, the ablation structure 101 and an accompanying deflection mechanism can be conveyed through the internal working channel 211 in a dimensionally compacted first configuration that is capable of expansion to a second radially expanded configuration upon exiting the distal end 110 of the endoscope 111 (For example, see FIGS. 34A, 34B, 35A, 35B, 36A, and 36B).

As shown in FIG. 34B, in one embodiment, the deflection mechanism is an inflation member 105, to which the ablation structure 101 can be integrated within or mounted/attached to, for example by etching, mounting or bonding. The inflation member 105 can be, for example, a compliant, non-compliant or semi-compliant balloon.

As shown in FIGS. 35B and 35B, in another embodiment, the deflection mechanism is an expandable member 209 that can expand to a second desired arrangement and configuration. As shown in FIG. 35B, the expandable member 209, can be an expandable stent, frame or cage device, to which an ablation structure 101 is mounted or integrated. For example, where the expandable member 209 is a wire cage, the wires can be a component of a bipolar circuit to provide the ablation structure 101 feature. Alternatively, the cage can have a flexible electrode circuit bonded or can be attached to an outer or inner surface of the cage to provide an ablation structure 101 that is an electrode. As shown in FIG. 36B, the expandable member 209, can be a folded or rolled series of hoops including or having an attached ablation structure 101 that expands upon exiting the endoscope distal end 110.

Figure 37:
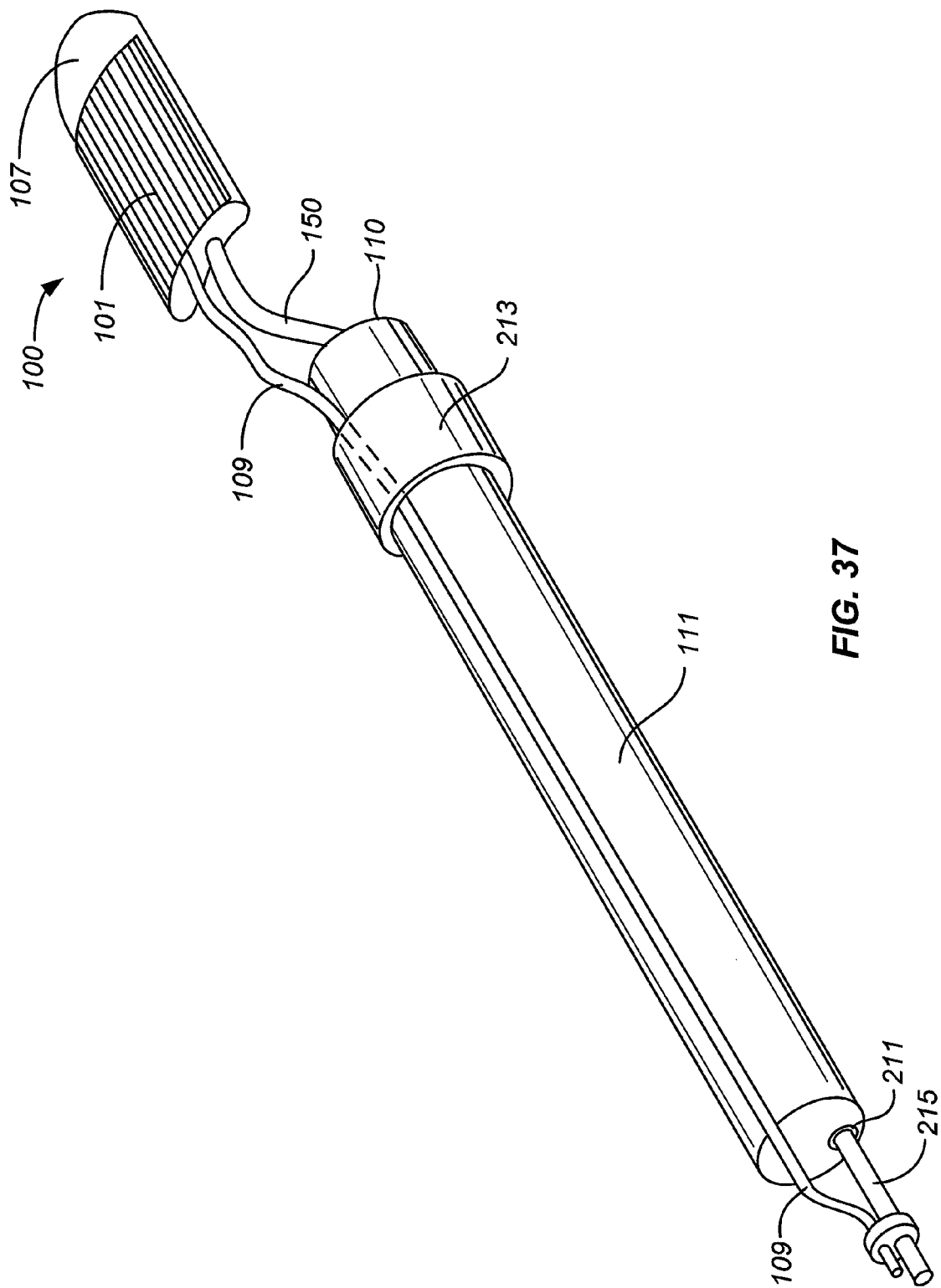
FIG. 37 is a view of the ablation device of the invention including an alternative deflection member.
Figure 38:
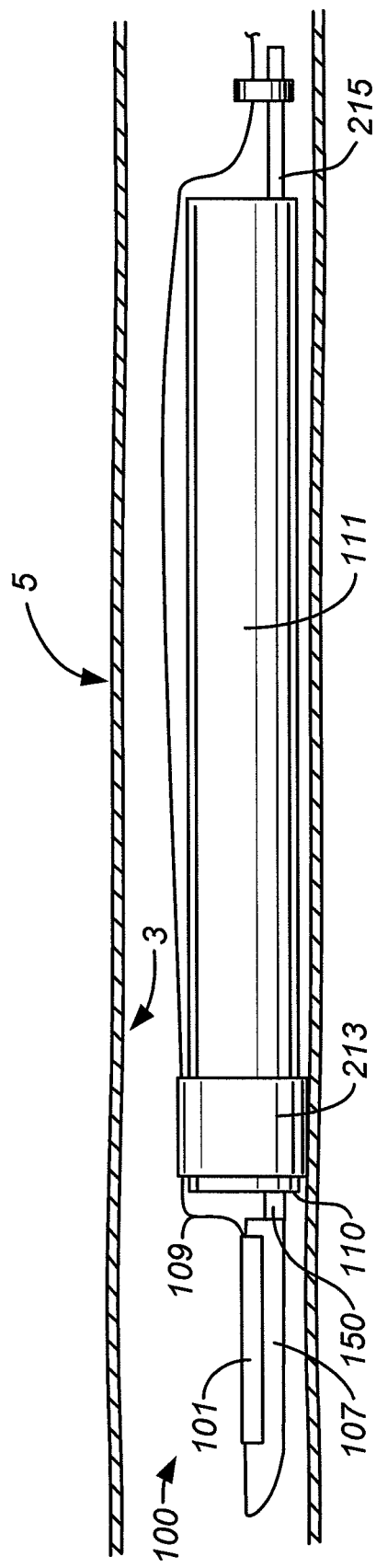
FIG. 38 is an illustration of the ablation device of the invention including an alternative deflection member positioned in a non-deflected position at a site of acute or chronic gastrointestinal tract bleeding.
Figure 39:
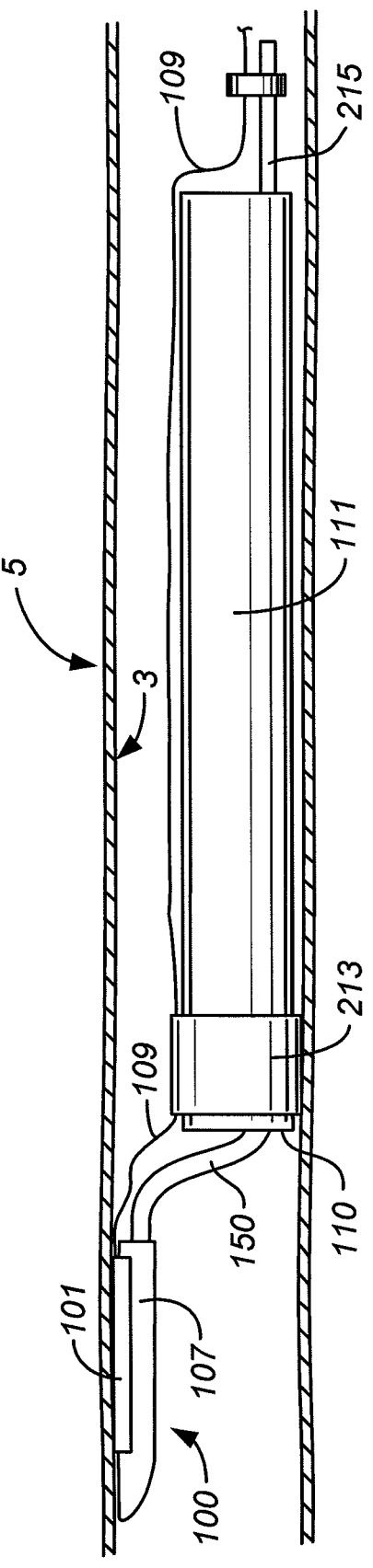
FIG. 39 is an illustration of the device shown in FIG. 38 wherein the deflection member is in a deflected position.

As further illustrated in FIGS. 37-39, the ablation structure 101 can be supported with a channel of the endoscope 111. In one embodiment as shown in FIGS. 37-39, an ablation device 100 includes a deflection member 150 that supports an attached housing 107 and ablation structure 101. As shown in FIG. 39, the endoscope 111 includes an internal working channel 211 suitable for advancing or retreating the deflection member 150 which is connected to an internal coupling mechanism 215 of the ablation device 100. FIGS. 37 and 39 both show a deflection member 150 including a bent region of the deflection member 150 in a deployed position, wherein the deflection member 150 bent region is positioned external to the endoscope distal end 110. FIG. 38 shows the deflection member 150 in an undeployed position, wherein the deflection member 150 bent region is positioned internal to the endoscope 111. The ablation structure 101 is thus supported with a channel of the endoscope 111 (the internal working channel 211 of the endoscope 111) by way of the deflection member 150 and the connected internal coupling mechanism 215 of the ablation device 100.

In addition, when the deflection member 150 is advanced or moved proximally or distally within the endoscope internal working channel 211, the deflection member 150 is accordingly advanced through a channel of the endoscope 111. In another implementation, as shown in FIG. 42, wherein the deflection mechanism is an inflatable member 105 (shown in a deployed configuration) coupled to an inflation line 113, the inflation line 113 can be disposed within the endoscope internal working channel 211. In yet another implementation, both the inflatable member 105 (in an undeployed configuration) and inflation line 113 can be advanced within the internal working channel 211 either proximally or distally in relation to the endoscope 111. Conductive wires 109 can pass through the working channel (not shown) or outside as shown in FIG. 37.

Figure 41:
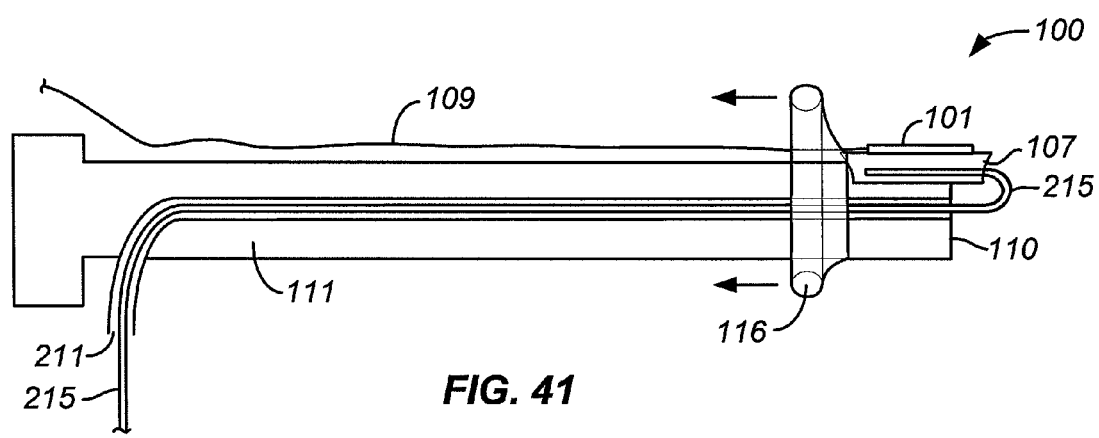
FIG. 41 is a cross sectional view of the ablation device of the invention showing an alternative internal coupling mechanism and a rolled sheath feature.

As shown in FIG. 41, in another implementation the endoscope 111 includes an internal working channel 211 suitable for supporting the ablation housing 107 and ablation structure 101 which are connected to an internal coupling mechanism 215 of the ablation device 100. As such, the connected ablation structure 101 is supported within a channel of the endoscope 111. Additionally as shown in FIG. 41, the housing 107 and ablation structure 101 can further be supported by an external region of the endoscope 111, wherein the internal coupling mechanism 215 is adapted and configured to position the housing 107 in contact with the external region of the endoscope 111. The internal coupling mechanism 215 can be cannulated (not shown) to facilitate use of the working channel to aspirate and flow in fluids or air.

In another ablation method, an additional step includes moving the ablation structure 101 with respect to the endoscope 111 within a luminal organ of the gastrointestinal tract at a site of acute or chronic bleeding. As illustrated in FIGS. 27, 28, 30, 32, and 47, and as discussed below, a sheath 103 of the ablation device 100 to which the ablation structure 101 is attached can enable moving the ablation structure 101 with respect to the endoscope 111. Further, as illustrated in FIGS. 34A, 35A, 36A, 37, 38, 39, and 41, and discussed above, an internal working channel 211 of the endoscope 111 through which at least a part of the ablation device 100 is disposed can enable moving the ablations structure 101 with respect to the endoscope 111.

Referring to FIGS. 11, 31, 42, and 44, in yet another method, the step of deflecting the ablation structure 101 toward a tissue surface 3 includes inflating an inflation member 105 of the ablation device 100 within a luminal organ of the gastrointestinal tract at a site of acute or chronic bleeding. The inflation member 105 can be arranged and configured to be reversibly inflatable. The inflation member 105 can be inserted along with the ablation structure 101 into an alimentary tract in a collapsed configuration and expanded upon localization at a pre-selected treatment area. In one implementation, the inflation member 105 is a balloon. For example, in FIGS. 11, 31, 42, and 44 it is shown how deflecting the ablation structure 101 toward a tissue surface 3 is achieved when the inflation member 105 is inflated or deployed. As illustrated in FIGS. 11, 31, 42, and 44, upon sufficient inflation, the inflation member 105 contacts a tissue surface 3 consequently deflecting the ablation structure 101 which contacts an opposing tissue surface 3.

Figure 19A:
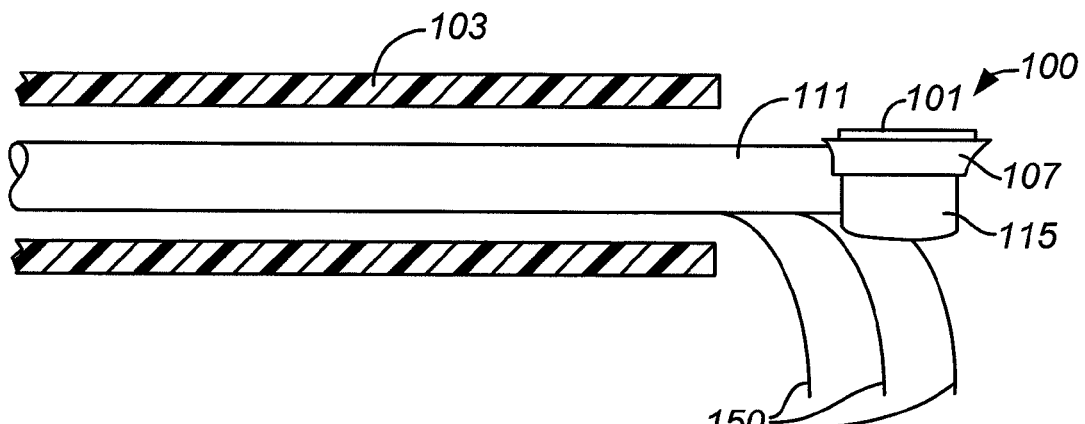
FIG. 19A is a view of the ablation device of the invention showing a deflection member feature.

As shown in FIGS. 19B, 20, 35, 36 and discussed above, in a further method, the step of deflecting the ablation structure 101 includes expanding a deflection structure or deflection member 150. In one implementation, as shown in FIG. 19A the ablation device 100 includes a sheath 103, wherein the sheath 103 is arranged and configured to receive the deflection member 150, the endoscope 111 and ablation structure 101 internally to the sheath 103. In one implementation, the deflection member 150 is a shape memory alloy, for example, Nitinol. The flexible extensions of the deflection member 150 in this embodiment can be coupled to the endoscope, an elastomeric sheath 115 of the ablation device 100 (shown in FIG. 19A) or any part of the device 100, including the ablation housing 107.

As shown in FIGS. 34, 35, 36, 37, 38, and 39, and discussed above, in a further method, the step of deflecting the ablation structure 101 includes moving a deflection structure or deflection member 150.

Figure 23:
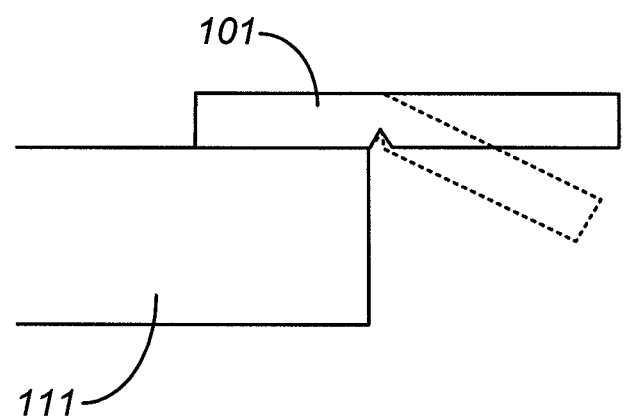
FIG. 23 is a view of the ablation device of the invention showing a pivoting ablation structure feature.

Briefly, in each case moving the deflection 150 is used to change the deflection member 150 from a non-deployed to a deployed configuration. As shown in FIG. 23, in one embodiment, deflecting the ablation structure 101 includes a flexing point in the ablation structure 101, wherein the ablation structure 101 can deflect in response to, for example, resistance met in contacting a tissue surface 3.

As shown in FIGS. 43, 44, and 45A-45C and as discussed in further detail below, in another method, the step of deflecting the ablation structure 101 includes rotating, pivoting, turning or spinning the ablation structure 101 with respect to the endoscope 111 along their respective and parallel longitudinal axes. Deflection of the ablation structure 101 with respect to the endoscope 111 can occur in combination with the endoscope 111 distal end 110 deflecting with respect to a target site on the wall of a luminal organ of the gastrointestinal tract at a site of acute or chronic bleeding. Also, the ablation structure 101 can deflect in combination with an inflation member 105 used to achieve apposition of the ablation device 100 to the tissue. In some embodiments, the step of deflecting the ablation structure 101 may additionally include any combination of the above disclosed deflecting steps.

Figure 46A:
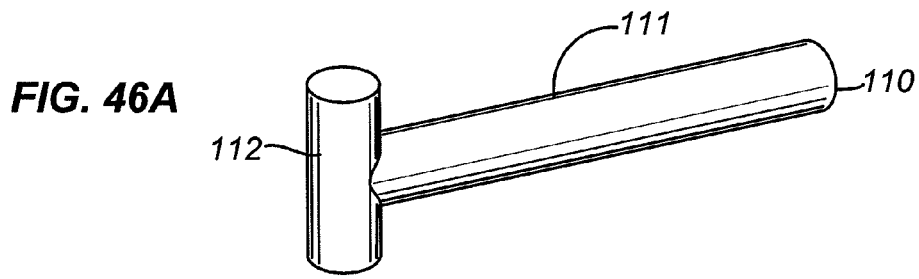
FIG. 46A is a view of an endoscope.
Figure 46B:
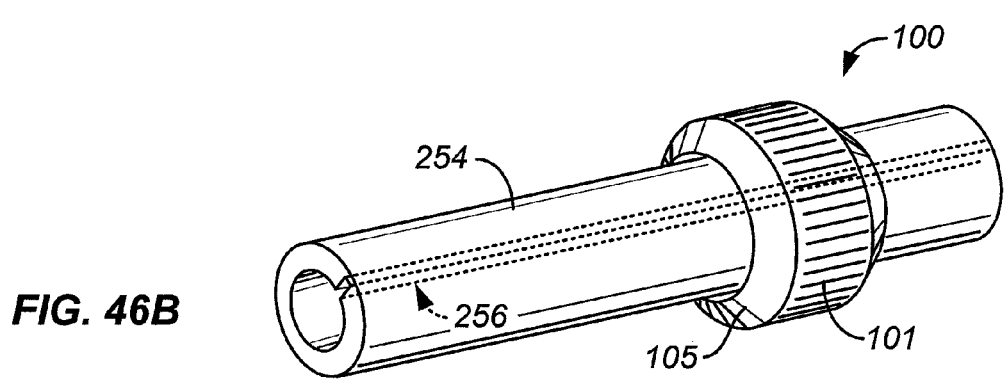
FIG. 46B is a view of the ablation device of the invention including a catheter feature.
Figure 47:
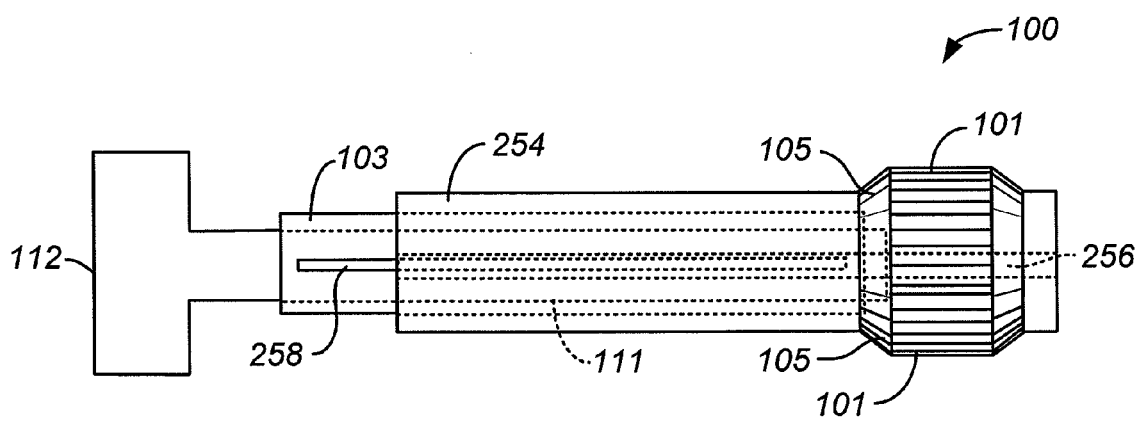
FIG. 47 is a view of the ablation device of the invention including the features shown in FIGS. 46A-46C in an assembly.

As shown in FIGS. 19, 20, 21, 22, 34A, 34B, 35A, 35B, 36A, 36B, 46B, and 47, in another ablation method, an additional step includes moving the ablation structure 101 from a first configuration to a second radially expanded configuration. The details regarding radial expansion of the ablation structure 101 shown in FIGS. 19, 20, 21, and 22 are described below, while the details for FIGS. 34A, 34B, 35A, 35B, 36A, and 36B are described above. Additionally, as shown in FIGS. 46B and 47 the ablation structure 101 can be arranged in a first configuration wherein the ablation structure 101 is coupled directly or alternatively through an housing 107 (not shown) to an inflation member 105 attached to a catheter 254. In an undeployed configuration as shown in FIGS. 46B and 47, the non-inflated inflation member 105 and ablation structure 101 have a relatively low profile in relation to the endoscope 111. When deployed, the inflation member 105 moves the ablation structure 101 to a second radially expanded configuration (not shown).

As shown in FIGS. 15, 16, 40, 43, 44, 45A-45C, 46B, and 47, in a further method, an additional step includes attaching the ablation structure 101 to the endoscope 111. As shown in FIGS. 15 and 16, attachment of the ablation structure 101 to the endoscope 111 can also be by way of an elastomeric sheath 115 The elastomeric sheath 115 can removably hold the ablation structure 101 in a desired position on the endoscope 111. The elastomeric sheath 115 can be arranged and configured to fit over the endoscope distal end 110. As shown in FIGS. 15 and 16, the inflation member 105 can be attached to the elastomeric sheath 115 or alternatively the inflation member 105 can also act as the "elastomeric sheath" (not shown).

In another method, the step of attaching the ablation structure 101 to the endoscope 111 includes attaching the ablation structure 101 to an outside surface of the endoscope. Alternatively, the attaching step can include, for example, attaching to an inside surface, an outside or inside feature of the endoscope, or any combinations of the above. Lubricants such as water, IPA, jelly, or oil may be use to aid attachment and removal of the ablation device from the endoscope.

As shown in FIG. 41, in a further method, the step of attaching the ablation structure 101 to the endoscope 111, includes an ablation structure 101 having an attached rolled sheath 116, wherein attaching the ablation structure 101 to the endoscope 111 includes unrolling the sheath 116 over an outside surface of the endoscope 111. The rolled sheath 116 can additionally cover the electrical connections 109 of the ablation device 100 along a length of the endoscope 111 (see FIG. 41). In a related method, the ablation structure 101 is attached to the endoscope 111 by an attaching step including unrolling the rolled sheath 116 over an outside surface of the endoscope 111 and part of the ablation structure 101.

Figure 40:
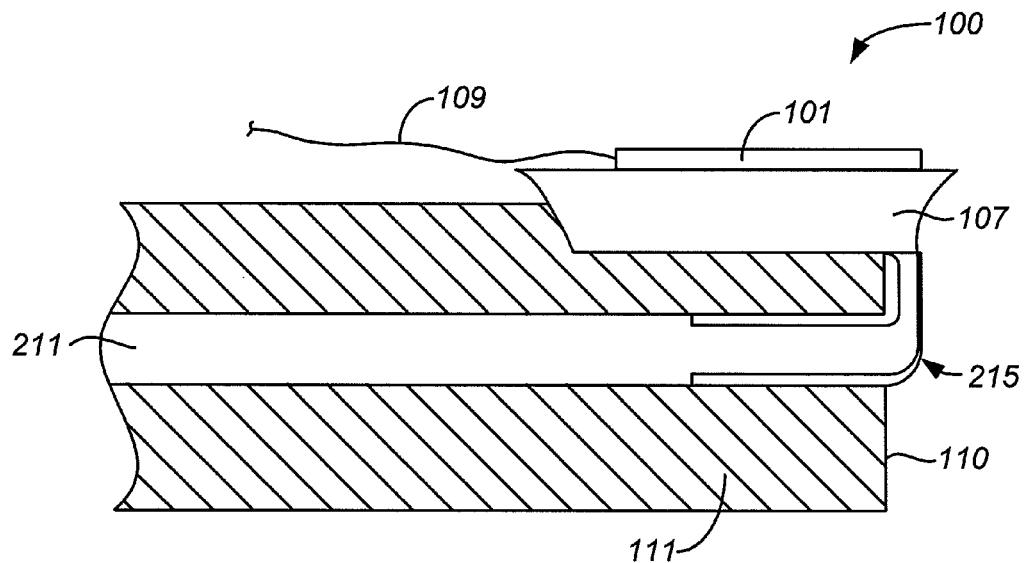
FIG. 40 is a cross sectional view of the ablation device of the invention showing an internal coupling mechanism feature.

In another method, as shown in FIG. 40, the step of attaching the ablation structure 101 to the endoscope 111 includes attaching the ablation structure 101 to a channel of the endoscope. As shown in FIG. 40, in one implementation, the housing 107 and ablation structure 101 are coupled to an internal coupling mechanism 215 that can be positioned within an internal working channel 211 of the endoscope 111.

The internal coupling mechanism 215 in FIG. 40 is shown as attached to the internal working channel 211 at the endoscope distal end 110. In this embodiment, the housing 107 and ablation structure 101 are shown in alignment with and coupled to an outside surface of the endoscope 111 near the distal end 110.

In one method of ablating tissue in the alimentary tract, the tissue surface 3 can include a first treatment area and activation of the ablation structure 101 step can include activation of the ablation structure 101 to ablate the first treatment area, and further include moving the ablation structure 101 to a second area without removing the ablation structure 101 from the patient and activating the ablation structure 101 to ablate the second tissue area 3. Moving, in this sense, refers to moving the ablational structure to the locale of a target site, and thereafter, further moving of the structure into a therapeutically effected position can be performed variously by inflating a balloon member, or deflection or inflating a deflection member, as described in detail elsewhere. For example, where two or more areas of the tissue surface 3 of a target area in the wall of an organ in the a site of acute or chronic gastrointestinal tract bleeding tract can be ablated by directing the ablation structure 101 to the first target region and then activating the ablation structure 101 to ablate the tissue surface 3. Then, without removing the ablation structure 101 from the patient, the ablation structure 101 can be directed to the second target area in the wall of an organ for ablation of the appropriate region of the tissue surface 3.

In general, in another aspect, an ablation device 100 is provided that includes an ablation structure 101 removably coupled to an endoscope distal end 110, and a deflection mechanism adapted and configured to move the ablation structure 101 toward a tissue surface 3 (see for example, FIGS. 5-19, 22, 22, 27-29, 30-32, 34A, 35A, 36A, 37, 38, 39, 42, 44, and 47).

In a related embodiment, the ablation device 100 additionally includes an ablation structure movement mechanism adapted to move the ablation structure 101 with respect to the endoscope 111. As discussed below and shown in FIGS. 26-28, and 30-32, the ablation structure movement mechanism can be a sheath 103 to which the ablation structure 101 is attached, wherein the sheath 103 is arranged and configured to move the ablation structure 101 with respect to an endoscope 111 received within the sheath 103. Alternatively, as discussed above and shown in FIGS. 34A, 35A, 36A, and 37-39, the ablation structure movement mechanism can be in the form of an internal coupling mechanism 215 of the ablation structure 100, wherein the ablation structure is connected to the internal coupling mechanism 215 and at least a portion of the internal coupling mechanism 215 is disposed internally to the endoscope.

In another embodiment, the ablation device 100 additionally includes a coupling mechanism designed to fit over an outside surface of an endoscope 111, to couple the ablation structure 101 with the endoscope 111. As discussed above, a spiral sheath 104, an elastomeric sheath 115, a rolled sheath 116 and an internal coupling mechanism as shown in FIGS. 15, 16, 40, and 41 respectively, are examples of such coupling mechanisms. In a particular embodiment, the coupling mechanism includes a sheath 103 capable of supporting the ablation structure 101. The sheath 103 can be tubing, a catheter or other suitable elongate members. The sheath 103 can be arranged and configured so that it can be moved independently of an associated endoscope.

As shown in FIG. 41, in another embodiment, the sheath 103 can be arranged and configured as a rolled sheath 116 that can be unrolled over the outside surface of the endoscope. In use, a rolled sheath 116 connected to the ablation device 100, for example at substantially near the proximal end of the housing 107 (from the perspective of an operator of the device), can be unrolled from such a position and continue to be unrolled toward the proximal end 112 of the endoscope 111 (see FIG. 47). In this way, the rolled sheath 116 can be caused to contact and cover all or a portion of the length of the endoscope 111 (not shown). Additionally, as the rolled sheath 116 is unrolled along the endoscope 111, it can sandwich the electrical connections 109 between the rolled sheath 116 and the endoscope 111 (see generally FIG. 41).

Figure 30:
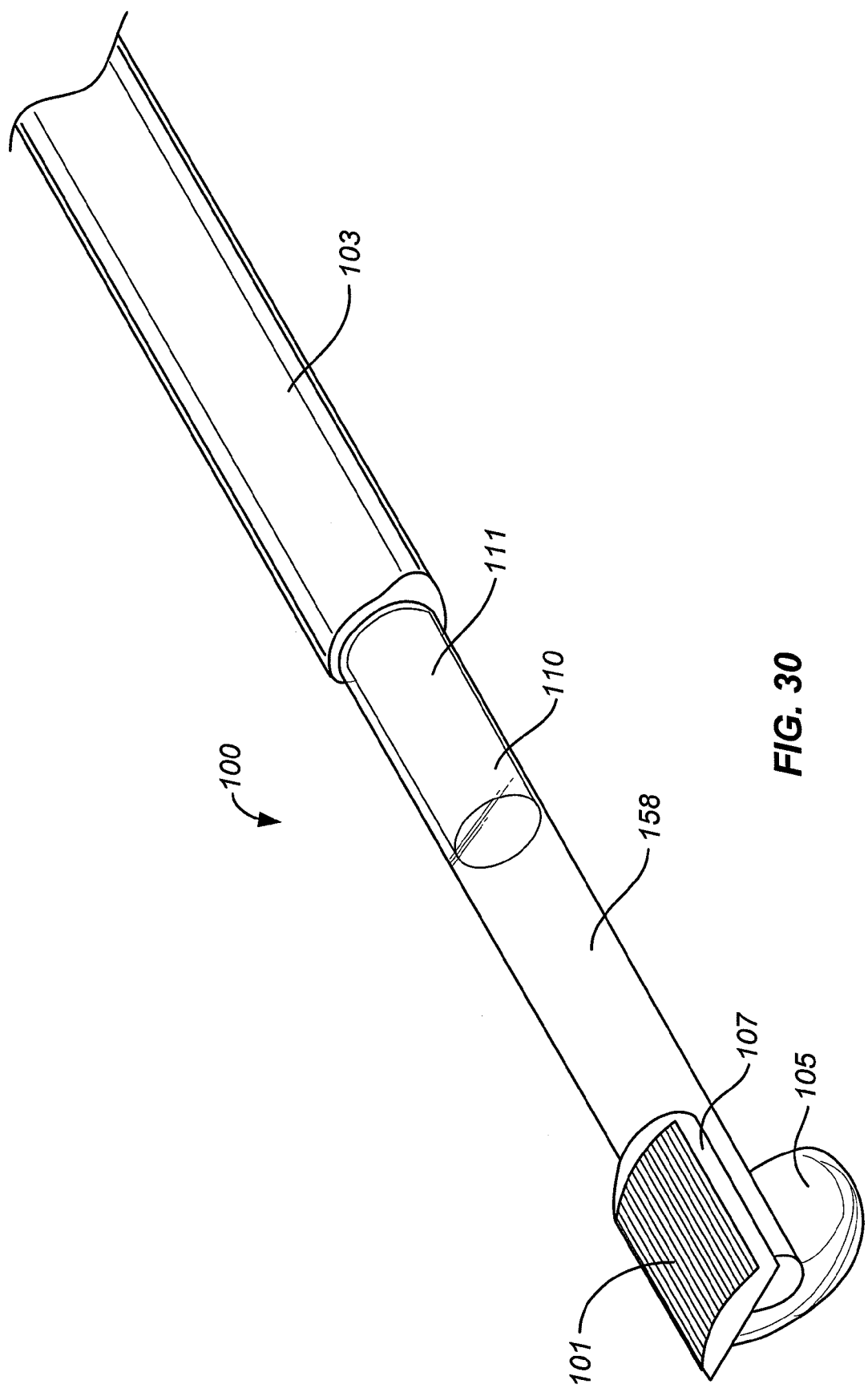
FIG. 30 is a view of the device including an alternative optically transmissive sheath feature and an inflation member feature in an expanded configuration.

In another embodiment, as shown in FIGS. 30 and 31, the sheath 103 can be arranged and configured to support a deflection mechanism wherein the deflection mechanism includes a deflection structure or deflection member 150. As illustrated in FIGS. 30 and 31, where the deflection member 150 is an inflation member 105, the inflation member 105 can be directly attached to the sheath 103. As shown in each case, the inflation member 105 is positioned opposite the placement of the ablation structure 101, which is also attached to the sheath 103. This configuration of the sheath 103 provides support for the inflation member 105 and the ablation structure 101 irrespective of the positioning of the endoscope distal end 110. For example, as shown in FIG. 30, the endoscope distal end 110 can be positioned to provide a gap between the distal end 110 and a distal end of the sheath 103 where the ablation structure 101 and inflation member 105 are positioned. In contrast, as shown in FIG. 31 the endoscope distal end 110 can extend through and beyond the distal end of the sheath 103.

Figure 26:
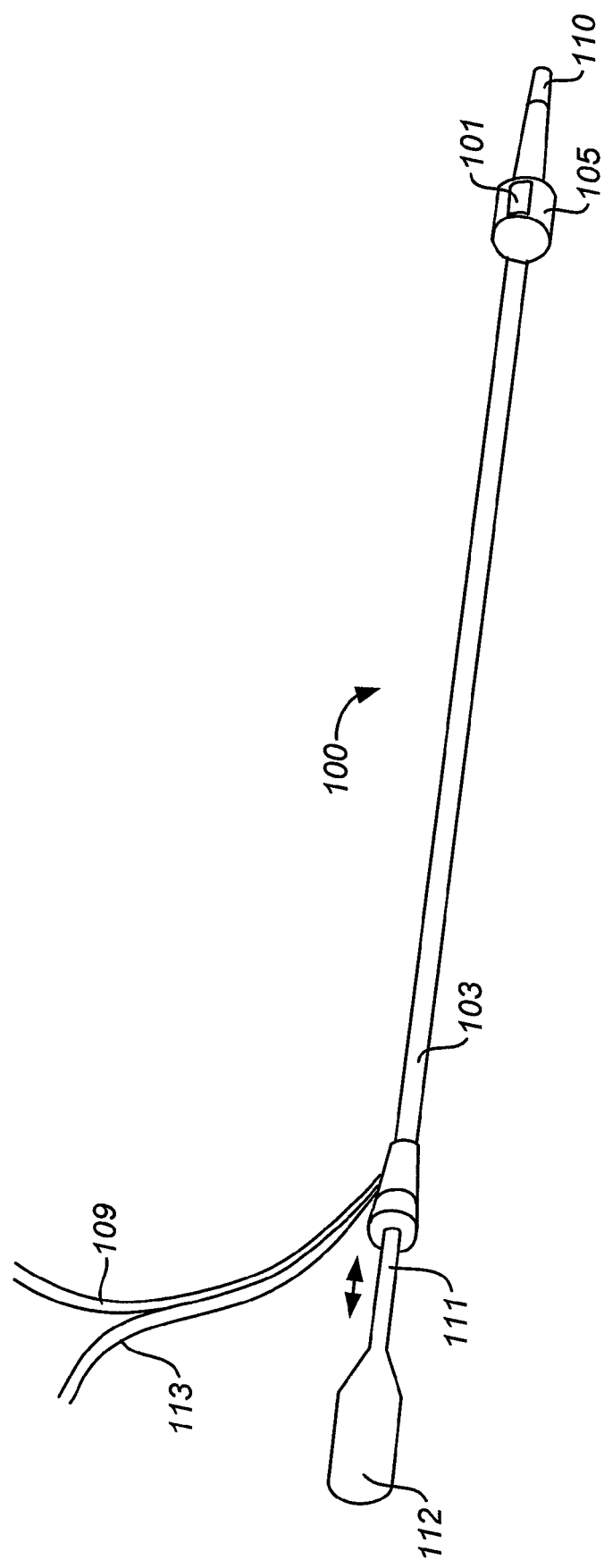
FIG. 26 is a view of the ablation device of the invention including an elongated sheath feature.

In another embodiment, as shown in FIG. 26, the sheath 103 can be elongated. FIG. 26 illustrates a sheath including electrical connections 109 and an inflation line 113. The sheath 103 may include pneumatic and/or over extruded wires impregnated within the sheath 103. In use, the sheath 103 can be introduced first into an alimentary tract, wherein the sheath 103 serves as a catheter like guide for introduction of the endoscope 111 within the sheath 103. Alternatively, the endoscope 111 may be introduced first and thereby serve as a guidewire for the sheath 103 to be introduced over. FIG. 26 also shows attachment of an inflation member 105 to the sheath 103, in an arrangement wherein the ablation structure 101 is attached to the inflation member 105 opposite the sheath 103 attachment point.

In embodiments shown in FIGS. 27 and 28, the sheath 103 includes an optically transmissive portion 158 adapted and configured to cooperate with a visual channel of an endoscope 111. For example, the sheath 103 may be made of clear, translucent or transparent polymeric tubing including PVC, acrylic, and Pebax® (a polyether block amide). As shown in FIG. 24, one component of an endoscope 111 can be a visual channel 161 that provides visual imaging of a tissue surface 3 as imaged from the endoscope distal end 110. For example, the transmissive portion 158 can allow visualization of the wall of an esophagus 3 through the transmissive portion 158 of the sheath 103. As shown in FIG. 28 and in the cross-section view provided in FIG. 29, the sheaths 103 shown in FIGS. 27 and 28, include an optically transmissive portion 158 arranged and configured to provide viewing of tissue surfaces 3 through the wall of the sheath 103, with the aid of an internally disposed endoscope 111 having a visual channel 161. Also shown in cross-section in FIG. 29 are portions of the sheath 103 through which electrical connections 109 and an inflation line 113 can pass. These features may be imbedded into the sheath 103 inner-wall or attached to the sheath 103 inner wall. As shown in FIG. 27, the sheath 103 including a transmissive portion 158 can extend past the endoscope distal tip 110. Alternatively, as shown in FIGS. 27, 28, and 31, the endoscope distal end 110 can extend distally past the transmissive portion 158 of the sheath 103.

In another implementation, the transmissive portion 158 of the sheath 103 can be reinforced structurally with coil or braid elements incorporated therein to prevent ovalization and/or collapsing of the sheath 103, particularly while deflecting the ablation device 100

Figure 32:
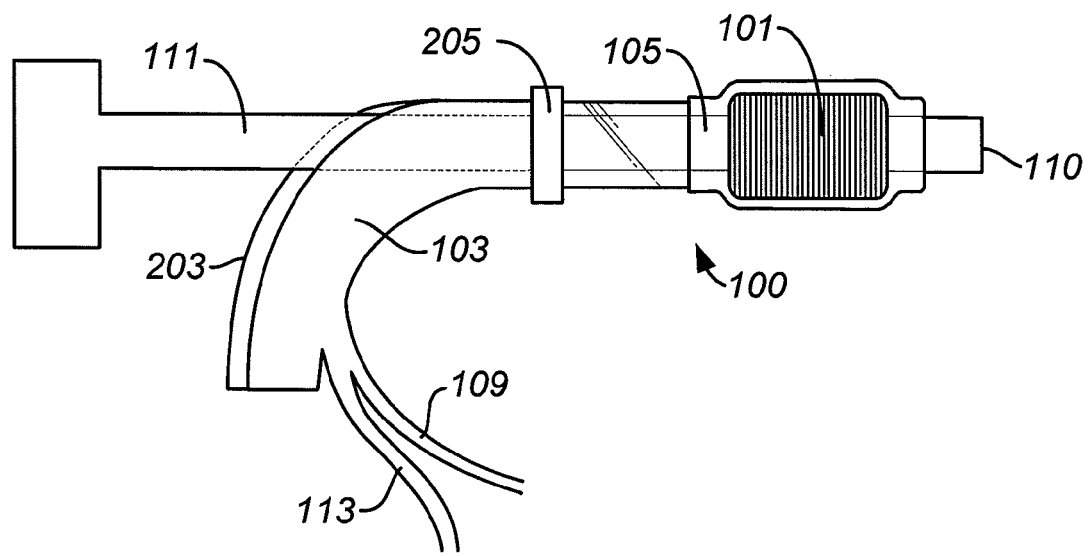
FIG. 32 is a view of the ablation device of the invention including a slit sheath feature.

In a further embodiment, the sheath 103 includes a slit 203 formed in a proximal portion of the sheath 103, the slit 203 being designed to open to admit an endoscope distal end 110 into the sheath. 103. As shown in FIG. 32 the proximal portion of the sheath 103 can include a perforation region or slit 203. The slit 203 can extend partially of fully along the length of the sheath 103. The slit 203 enables the sheath 103 to be pulled back, or opened when, for example introducing an endoscope 111 into the sheath 103. In one implementation, as shown in FIG. 32, the sheath 103 additionally includes a locking collar 205 for locking the sheath 103 in a desired position in respect to the endoscope 111.

Figure 33A:
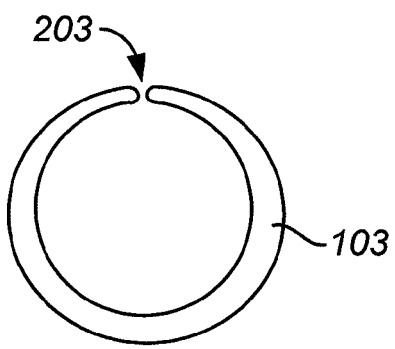
FIG. 33A is an end view of a slit sheath feature of the device wherein the sheath is in an unexpanded configuration.
Figure 33B:
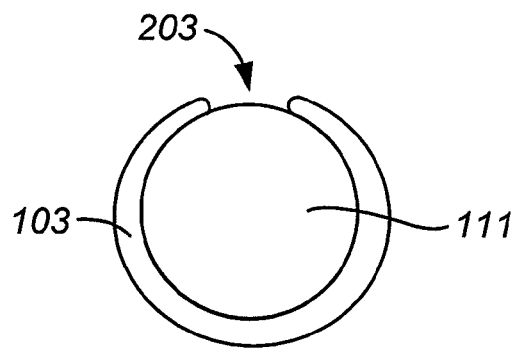
FIG. 33B is an end view of a slit sheath feature of the device and an endoscope wherein the sheath is in an expanded configuration.

As shown in FIGS. 33A and 33B, the distal portion of the sheath 103 can have a smaller outer diameter than a, proximal portion of the sheath 103, the distal portion of the sheath 103 being adapted and configured to be expanded when an endoscope 111 is inserted into it (not shown). This embodiment can aid in accessing an endoscope 111 in a case where the sheath 103 is advanced first into a target site within the alimentary tract. Since the distal end of the sheath 103 is smaller in diameter, but includes a slit 203, the sheath 103 can accept a larger outside diameter endoscope 111 because when the endoscope 111 is advanced, the slit 203 of the sheath 103 allows for widening of the sheath 103.

In general, in another aspect, a method of ablating tissue in within the alimentary tract includes advancing an ablation structure 101 into the alimentary tract while supporting the ablation structure 101 with an endoscope 111. The endoscope distal end 110 can be bent to move the ablation structure 101 into contact with a tissue surface followed by activation of the ablation structure 101 to ablate the tissue surface 3 (see e.g., FIG. 43). In a particular embodiment, the ablation structure 101 includes a plurality of electrodes and the activating step includes applying energy to the electrodes.

In general, in another aspect the coupling mechanism is designed to fit over an outside surface of an endoscope 111, to couple the ablation structure 101 with the endoscope 111, rather than being for example, a sheath (as discussed above), and is adapted and configured to provide a certain freedom of movement to the ablation structure 101, including but not limited to flexing and/or rotating and/or pivoting with respect to the endoscope 111 when coupled to the endoscope 111. The freedom of movement is with respect to one, two, or three axes, thereby providing one, two, or three degrees of freedom. Non-limiting examples of suitable coupling mechanisms include a flex joint, pin joint, U-joint, ball joint, or any combination thereof. The following described coupling mechanism embodiments advantageously provide for a substantially uniform apposition force between a supporting endoscope 111 and an ablation structure 101 when localized at a target tissue surface 3.

As shown in FIGS. 43, 44, 45A, and 45B, the coupling mechanism can be a ring 250 attached to the housing 107 and the endoscope 111, wherein the housing 107 is adapted and configured to flex, rotate or pivot about the ring 250. For example, as illustrated in FIG. 43, where the ablation device 100 is coupled to a deflectable distal end 110 of an endoscope 111 by a ring 250, when the device 100 is deflected toward the tissue surface 3 of the wall of the lumen of the gastrointestinal tract a site of acute or chronic bleeding, the housing 107 upon contact aligns the ablation structure 101 with the tissue surface 3 by flexing, rotating or pivoting about the ring 250 coupling. In these embodiments, the endoscope and the housing that supports the ablation structure both have their own longitudinal axis, and these axes are situated parallel to each other. The coupling mechanism that attaches the housing to the endoscope allows a pivoting movement between the longitudinal axis of the housing and the longitudinal axis of the endoscope. Advantageously, sufficient contact pressure provided by deflection of the distal end 110 of the endoscope 101 can produce a desired degree of contact between the ablation structure 101 and the tissue surface 3, irrespective of the precise alignment of the distal end 112 in respect to a plane of the tissue surface 3 to be treated.

For the purposes of this disclosure, a "desired degree of contact", "desired contact", "therapeutic contact", or "therapeutically effective contact" between the ablation structure 101 and the tissue surface 3, includes complete or substantially-complete contact between all or a portion of a predetermined target on the tissue surface 3 (e.g. a site on the wall of a luminal organ of the gastrointestinal tract at a site of acute or chronic bleeding) by all or a portion of the ablation structure 101. It should also be understood that therapeutic contact, as described in this disclosure typically occurs as a consequence of an ablational surface on an apparatus having been moved into such contact by the expansion of an expandable member such as a balloon, or by expanding, moving, or deflecting a deflection structure. By all such approaches, such movement or bringing into therapeutic contact includes the exertion or application of pressure. Such pressuring is a factor in effecting coaptive ablation, wherein pressure exerted through tissue on blood vessels causes them to be partially or substantially emptied of blood, and coincidentally serves as a counter-pressure that prevents entry of blood normally brought about by blood pressure. Thus, any occurrence of moving or expanding a member so as to bring an ablation surface against target tissue can also be understood as pressuring the tissue.

As shown in FIG. 44, in a different yet related embodiment, where the deflection mechanism of the ablation device 100 is an inflatable member 105, a ring 250 coupling allows for flexing, rotating or pivoting of the housing 107 and ablation structure 101. As in the previous case, sufficient contact pressure provided through deflection, here by the inflatable member 105, can produce a desired degree of contact between the ablation structure 101 and the tissue surface 3. Again, advantageously, the desired contact can be achieved irrespective of the precise alignment of the deflected endoscope 111 distal end 110 in respect to a plane of the tissue surface 3 to be treated, because of the flexing, rotating or pivoting provided by the ring 250 coupling.

As shown in FIG. 45A, in a related embodiment, the coupling mechanism between the ablation device 100 and an endoscope 111 can be an elastic band 252, wherein the housing 107 of the device 100 is flexibly coupled to the elastic band 252. For example, as illustrated in FIG. 45C, where the ablation device 100 is coupled to a distal end 110 of an endoscope 111 by an elastic band 252, when the device 100 is deflected toward a tissue surface 3 of the wall of a luminal organ of the gastrointestinal tract at a site of acute or chronic bleeding, alignment between the housing 107 and accordingly the ablation structure 101 and the tissue surface 3, can be achieved by flexing about the elastic band 252 coupling. Once more, advantageously, the desired contact can be achieved irrespective of the precise alignment of the deflected endoscope's 111 distal end 110 in respect to a plane of the tissue surface 3 to be treated, because of the flexing capability provided by the elastic band 252 coupling.

As shown in FIG. 45A, in another related embodiment, the coupling mechanism between the ablation device 100 and an endoscope 111 can be a combination of a ring 250 and an elastic band 252, wherein the housing 107 of the device 100 is coupled to the elastic band 252. For example, as illustrated in FIG. 45A, where the ablation device 100 is coupled to a distal end 110 of an endoscope 111 by an elastic band 252, when the device 100 is deflected toward a tissue surface 3 of, for example, the wall of a luminal organ of the gastrointestinal tract at a site of acute or chronic bleeding (not shown), alignment between the housing 107 and accordingly the ablation structure 101, and the tissue surface 3 by flexing, rotating or pivoting about the ring 250 and the elastic band 252 coupling can be achieved. Again, advantageously, the desired contact can be achieved irrespective of the precise alignment of the deflected endoscope 111 distal end 110 in respect to a plane of the tissue surface 3 to be treated, because of the flexing rotating or pivoting provided by the elastic band 252 coupling.

In another embodiment, the ablation device 100 additionally includes an alternative coupling mechanism between the ablation device 100 and an endoscope 111 that is arranged and configured to fit within a channel of an endoscope 111. The coupling mechanism can be an internal coupling mechanism 215 and can be configured and arranged to couple the ablation structure 101 within an internal working channel 211 of an endoscope 111 (see FIG. 37 and as discussed above).

As shown in FIGS. 34A, 34B, 35A, 35B, 36A, and 36B, in one embodiment of such a coupling mechanism, the ablation structure 101 is adapted and configured to fit within the endoscope internal working channel 211. Additionally, as shown in FIGS. 34A, 34B, 35A, 35B, 36A, and 36B, in a related embodiment, the deflection mechanism is also adapted and configured to fit within the endoscope internal working channel 211.

In each of the embodiments described above and shown in FIGS. 34A, 34B, 35A, 35B, 36A, and 36B, after expansion of the inflatable member 105 or expandable member 209 and subsequent treatment of a target tissue 3, the coupling means can further serve as a means to draw, pull or retrieve the ablation structure 101 and deflection mechanism back into the endoscope internal working channel 211. Furthermore, in addition to providing coupling of the ablation structure 101 with the endoscope internal working channel 112, the coupling mechanism can include electrical connections 109 to provide energy to the ablation structure 101.

In a related embodiment, again wherein the ablation device 100 additionally includes a coupling mechanism adapted and configured to fit within a channel of an endoscope 111, the coupling mechanism can include a shape memory member and the deflection mechanism can include a bent portion of the shape memory member. As shown in FIGS. 37-39, the coupling mechanism can be an internal coupling mechanism 215. As shown, the internal coupling mechanism 215 can be disposed within an endoscope internal working channel 211 and extend beyond the endoscope distal end 100. Additionally, the internal coupling mechanism 215 can be connected to a deflection mechanism that is a deflection member 150. The deflection member 150 can include a bent portion and can be connected to the housing 107. As shown in FIG. 38 and discussed above, the bent portion of the deflection member 150 can be disposed within the endoscope internal working channel 211, causing the ablation structure 101 to move into a non-deployed position. Upon advancing the internal coupling mechanism 215 toward the endoscope distal end 110, the shape memory nature of the deflection member 150 facilitates deployment of the ablation structure 101 to a position suitable for ablation.

In general, in one aspect, the ablation structure 101 of the ablation device 100 includes an optically transmissive portion 158 adapted and configured to cooperate with a visual channel of an endoscope 111. As shown in FIGS. 27-31 and discussed above, the optically transmissive portion 158 can be a sheath 103 of the ablation device 100.

In one embodiment, the ablation structure 101 of the ablation device 100 is further adapted and configured to move from a first configuration to a second radially expanded configuration. As shown in FIGS. 19-22, the ablation structure 101 and housing 107 can be designed to reversibly move from a first less radially expanded configuration (see FIGS. 20 and 21) to a second radially expanded configuration useful for ablation. Foldable or deflectable configurations that provide for reversible radial expansion of the housing 107 and the ablation structure 101 can facilitate access to tissue surfaces because of reduced size. Additionally, foldable or deflectable configurations are helpful in regard to cleaning, introduction, retrieval, and repositioning of the device in the luminal organs of the gastrointestinal tract at a site of acute or chronic bleeding.

Figure 19B:
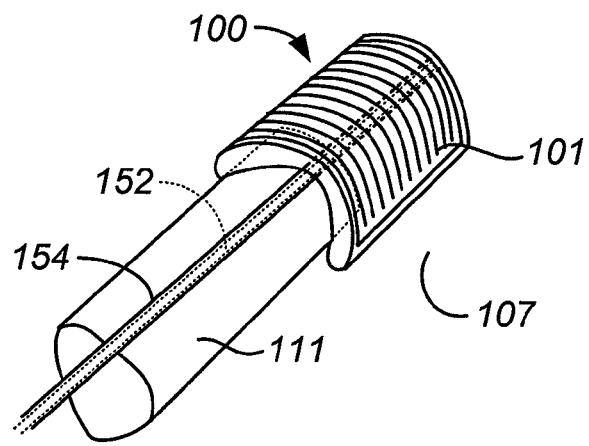
FIG. 19B is a view of the ablation device of the invention showing an alternative deflection member wherein the device is in an expanded configuration.
Figure 20:
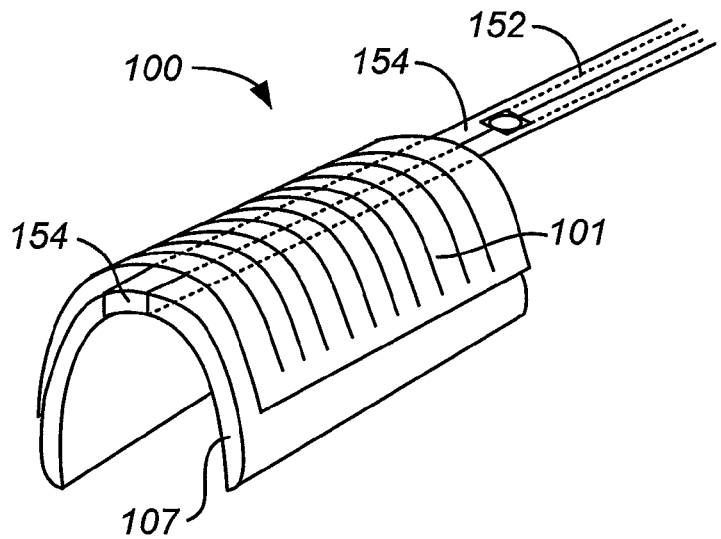
FIG. 20 is a view of device shown in FIG. 19B wherein the deflection member is in an unexpanded configuration.
Figure 21:
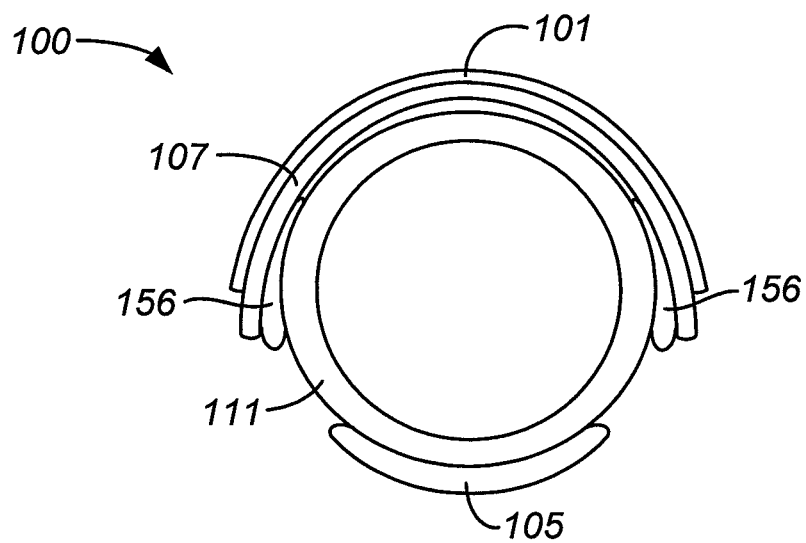
FIG. 21 is an end view of the device in an unexpanded configuration.

The ablation device 100 shown in FIGS. 19B and 20 includes an ablation structure actuator 152 arranged and configured to move the ablation structure 101 from the first configuration (see FIG. 20) to a second radially-expanded configuration (see FIG. 21). As shown (FIGS. 19B and 20), the actuator 152 can be elongate and designed to work with a receiver 154 arranged and configured to receive the actuator 152. The actuator 152 can be a wire, rod or other suitable elongate structure. Alternatively, the actuator 152 can be a hydraulic actuation means with or without a balloon component. In a particular embodiment, the actuator 152 is a stiffening wire.

As illustrated in FIG. 20, before the actuator 152 is disposed within the portion of receiver 154 attached to the housing 107, both the housing 107 and the ablation structure 101 are in a first position having a first configuration. As illustrated in FIG. 21, after the actuator 152 is partially or fully introduced into the receiver 154, the housing 107 and the ablation structure 101 are consequently changed to a second radially expanded configuration relative to the first configuration. Introduction of the actuator 152 into the receiver 154 can force the portions of the housing 107 and ablation structure 101 flanking the receiver 154 to expand radially (see FIG. 19). In one embodiment, the housing 107 is heat set in a flexed first configuration suitable for positioning the ablation device 100 near a target tissue surface 3. After a target tissue surface 3 has been reached, the actuator 152 can be introduced into the receiver 154 to achieve the second radially expanded configuration which is useful for ablation of the tissue surface 3.

In a related alternative embodiment, the housing 107 and ablation structure 101 include an unconstrained shape that is radially expanded and includes one or more flex points to allow for collapsed or reduced radial expansion when positioned distally to the distal end 110 of an endoscope 111 and compressed by an elastomeric sheath 115 (not shown).

Figure 22:
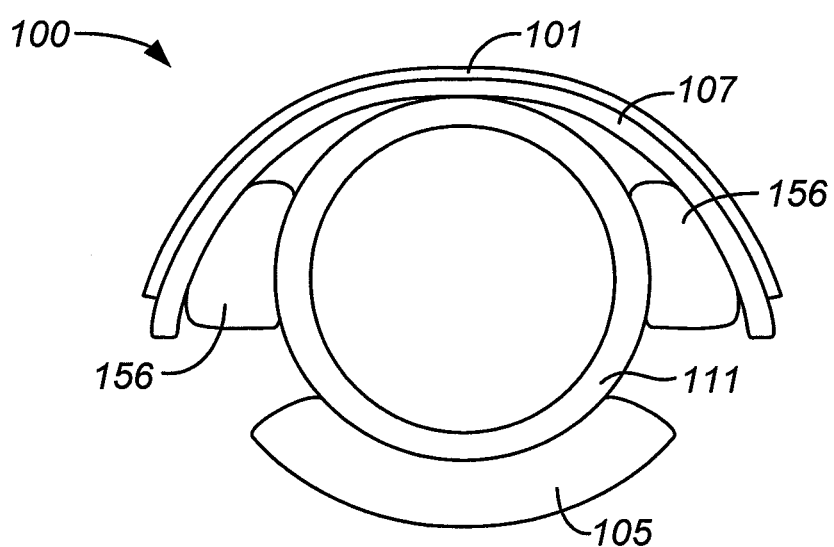
FIG. 22 is an end view of the device shown in FIG. 21 in an expanded configuration.

As shown in FIGS. 21 and 22, in another embodiment, the ablation structure 101 of the ablation device 100 is adapted and configured to move from a first configuration to a second radially expanded configuration wherein the ablation device 100 further includes an expandable member 156. The expandable member 156 can be positioned between the housing 107 and the endoscope 111, where in unexpanded form, the ablation structure 101 is accordingly configured in a first configuration. Upon expansion of the expandable member 156, the ablation structure 101 configuration is changed to a second radially expanded configuration (see FIG. 21).

In one embodiment, the deflection mechanism of the ablation device 100 includes an inflatable inflation member 105. As shown in FIGS. 11, 21, 22, 25B, 27, 28, 30, 31, 34A, 34B, 42, 44, 46, and 47 and discussed above, the inflation member 105 can facilitate deflection of the device 100 in relation to a tissue surface 3.

In another embodiment, the deflection mechanism includes an expandable member 156 (see FIGS. 35B and 36B, discussed in detail above). As shown in FIG. 35B, the expandable member 209, can be an expandable stent, frame or cage device. As shown in FIG. 36B, the expandable member 209, can be an expanded series of connected hoops that can be folded or rolled prior to expansion.

Figure 46C:
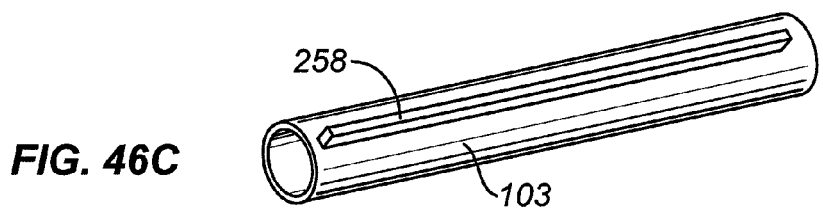
FIG. 46C is a view of a sheath feature of the device.

In another advantageous embodiment, the ablation device 100 further comprises a torque transmission member adapted and configured to transmit torque from a proximal end of the endoscope 111 to the ablation structure 101 to rotate the ablation structure 101 about a central axis of the endoscope 111. In a particular embodiment, the torque transmission member includes first and second interlocking members adapted to resist relative movement between the endoscope 111 and the ablation structure 101 about the central axis. As shown in FIGS. 46B, 46C, and 47, in one embodiment the first interlocking member is a key 258 and the second interlocking member is a keyway 256. In one embodiment, the first interlocking member is attached to a sheath 103 surrounding the endoscope 111 and the second interlocking member is attached to a catheter 254 supporting the ablation structure 101. For example, as shown in FIGS. 46B, 46C, and 47, the key 258 can be attached to a sheath 103 surrounding the endoscope 111 and the keyway 256 can be attached to a catheter 254 supporting the ablation structure 101. In a further related embodiment, the catheter 254 and sheath 103 are arranged and configured for relative movement along the central axis of the endoscope 111. The sheath 103 can be, for example, an elastomeric sheath wherein the key 258 is attached to the outside of the sheath 103 substantially along a longitudinal axis of the sheath 103 (see FIG. 46C). In use, this embodiment provides for a 1-to-1 torque transmission of the ablation device 100 endoscope assembly 111 when the endoscope proximal end 112 is manipulated, while also providing for positioning of the ablation structure 101 either proximal or distal to the endoscope distal end 110 in situ. Additionally, the sheath 103 can be pre-loaded into the catheter 254 or loaded separately.

In general, in one aspect, an ablation device 100 is provided including an ablation structure 101, and a coupling mechanism adapted to removably couple the ablation structure 101 to a distal end 110 of an endoscope 111 and to permit the ablation structure 101 to rotate and/or pivot with respect to the endoscope when coupled to the endoscope. Various related embodiments wherein, for example, the coupling mechanism comprises a ring 250 and the ablation structure 101 is adapted to rotate and/or pivot about the ring 250; wherein the coupling mechanism comprises an elastic band 252 adapted to flex to permit the ablation structure 101 to rotate and/or pivot; wherein the ablation device 100 further includes a deflection mechanism adapted and configured to move the ablation structure 101 toward a tissue surface 3; and, wherein such a deflection mechanism includes an inflatable member, have been set out in detail above.

FIGS. 56A and 56B provide views of an ablational device with an ablational surface on a hinge 159 which acts in a manner similar to mechanism depicted in FIG. 43, and which allows a free pivoting movement of the ablational surface between its longitudinal axis and the longitudinal axis of an endoscope. FIG. 56A shows the device with the ablational surface 101 oriented in parallel with the endoscope, the surface having made contact with the inner surface of a gastrointestinal luminal wall 5 at a desired target area. The ablation surface 101 is supported by a deflection member 150 that can be expressed from a working channel, and withdrawn back into a working channel within the endoscope. FIG. 56B shows the device with the longitudinal axis of the ablational surface 101 oriented at about a right angle with respect to the longitudinal axis of the endoscope. This pivoting as a passive response of the ablational surface 101, as it easily rotates on hinge 159 through a flexion range of 0 degrees (parallel to the endoscope 111) to about 170 degrees. As shown, the angle of the surface is about 90 degrees with respect to the endoscope.

While most embodiments described herein have made use of radiofrequency energy as an exemplary ablational energy, and consequently have made use of electrodes as an energy transmitting element, it should be understood that these examples are not limiting with regard to energy source and energy delivery or transmitting elements. As also described herein, other forms of energy, as well as cryoablating approaches, may provide for ablation of target areas in such a manner that ablation is fractional or partial, as described herein, where some portions of target area tissue are ablated, and some portions of target area tissue are not substantially ablated.

Device Embodiments that are Deployable Through an Endoscope

As noted above, ablation devices may be deployable or positionable at site of acute or chronic bleeding in various ways in conjunction with an endoscope that provides visual capability to a physician. For example, an endoscopic catheter can be positionable into therapeutic contact with a balloon or another form of expandable member, or moving or deflecting a deflecting member, and embodiments can be mounted on the end or on an appropriate alternative site of an endoscope, or the ablation device can pass through a working channel or accessory channel of an endoscope. An ablation device that can be passed through a working channel of an endoscope provides practical benefits in that the operation of the endoscope is in not hindered or complicated any by external device features, and because physician practitioners are very familiar and comfortable with working channel devices. A constraint, however, is that devices housed within a working channel need have a collapsed configuration that fits within the dimensions of the channel, which are typically about 2-5 mm in diameter. Further, such in-channel devices need to be able to move easily back and forth between a stowed or deployable configuration and a working or deployed configuration. Several examples of in-channel devices are provided in FIGS. 59A-64, and described below.

Figure 59A:
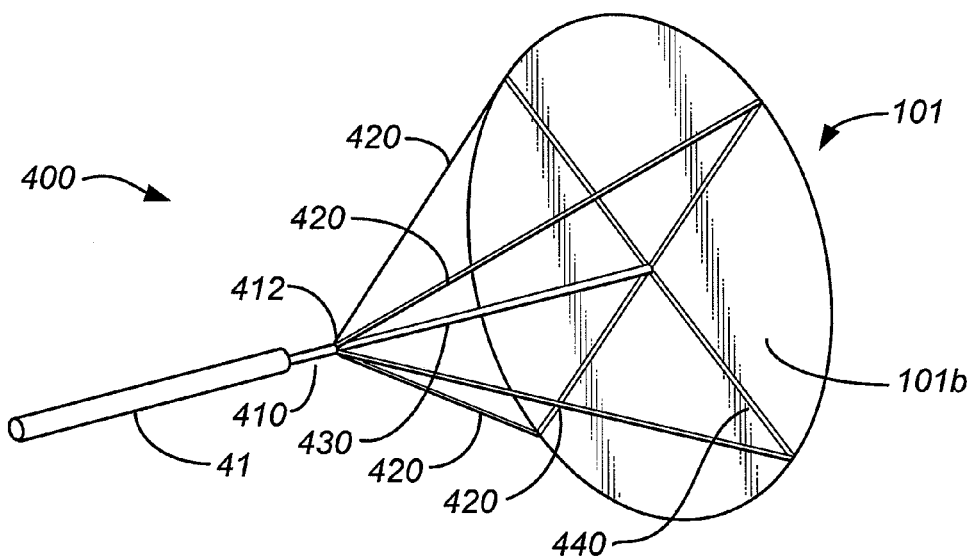
FIGS. 59A and 59B provide views of an ablation device deployable through the working channel of an endoscope that is configured to present a broad field ablational surface generally orthogonal or perpendicular to the longitudinal axis of the delivery endoscope.
Figure 59B:
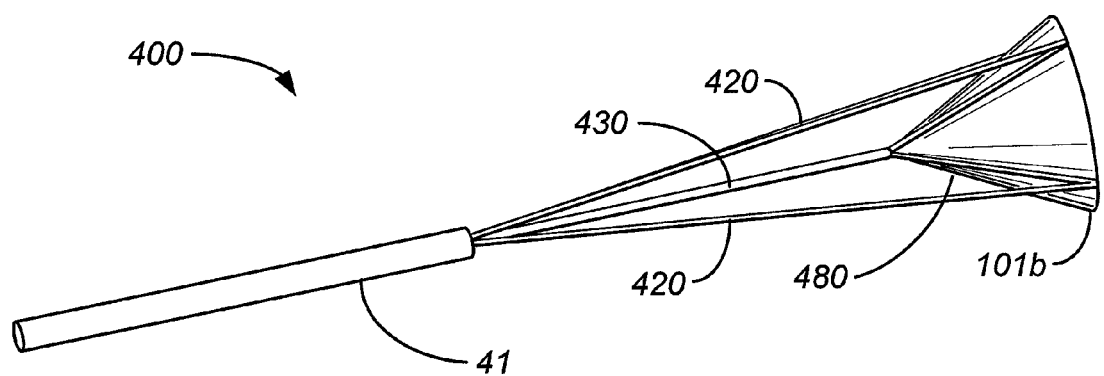

FIGS. 59A and 59B provide views of an ablation device 400 deployable through the working channel of an endoscope that is configured to present a broad field ablational surface generally orthogonal or perpendicular to the longitudinal axis of the delivery endoscope. FIG. 59A shows the device in a fully deployed configuration. FIG. 59A shows the device in a configuration midway between being deployed and collapsed, so as to be stowed within the working channel of an endoscope. The device 400 is supported at the distal end of a shaft 41 that supports an internal coaxial rod 410. At a junction 412, the coaxial rod joins a plurality of peripheral struts 420 that support an ablation energy delivery surface 101. A wire 430 also extends from the junction 412 to the center of the back of ablation energy delivery surface 101b, which is further supported by frame elements 440. By pushing the coaxial rod distally, so that it projects forward from a working channel, the ablation surface opens to provide a broad field ablation energy delivery surface. As the coaxial rod is pulled proximally, the ablation energy delivery surface pulls in on itself in a reverse-umbrella manner, and is in a configuration that can be withdrawn into the working channel. In alternate embodiments, the ablation delivery surface 101 and its support frame elements 440 can be adapted to provide a forward face that is convex rather than flat, in order to better meet a broad luminal surface. It can be further appreciated that the device and the ablation surface are steerable by virtue of being supported by an endoscope, and further, the operating physician has the ability to manually provide pressure, so as to make effective therapeutic contact with the target area. It may also be appreciated that ablation delivery elements can be arranged on the ablation surface 101 in any configuration described elsewhere in this disclosure.

Figure 60:
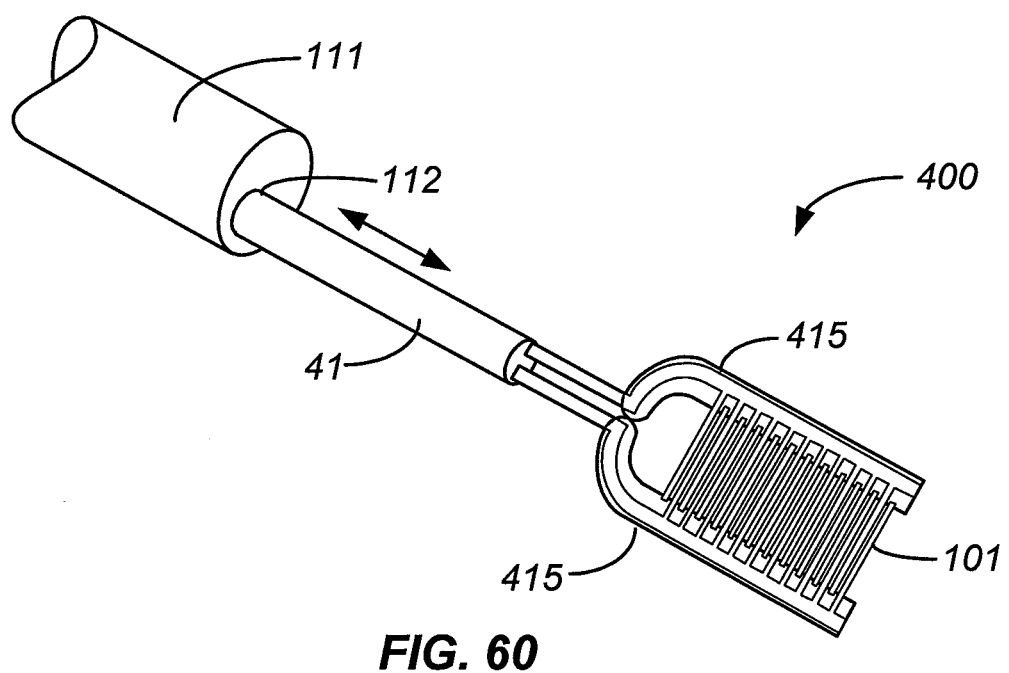
FIG. 60 depicts an embodiment of an ablation device deployable through the working channel of an endoscope that is adapted to present an ablational surface generally parallel to the longitudinal axis of the delivery endoscope. The device includes an ablational structure that has two parallel collapsible shape memory ribs, across which ablative electrodes are strung, the strung electrodes configured to be taut across the space between the ribs in the deployed condition.

FIG. 60 depicts an embodiment of an ablation device 400 deployable through the working channel 112 of an endoscope 111 that is adapted to present an ablational surface 101 generally parallel to the longitudinal axis of the delivery endoscope. The device includes an ablational structure that has two parallel collapsible shape memory ribs 415 (comprising Nitinol, for example), across which ablative electrodes are strung, the stung electrodes configured to be taut across the space between the ribs in the deployed condition to form the ablational surface 101. As the distal end of a support shaft 41 is pushed out from the working channel of an endoscope 111, the support ribs 415 expand per their preferred configuration. As the support shaft is pulled back into the endoscope, the proximal tapered portion of the ribs 415 draws them together as the pass through the opening of the working channel. The ablational surface 101 is adapted to provide focal sites of ablation within a target area.

Figure 61A:
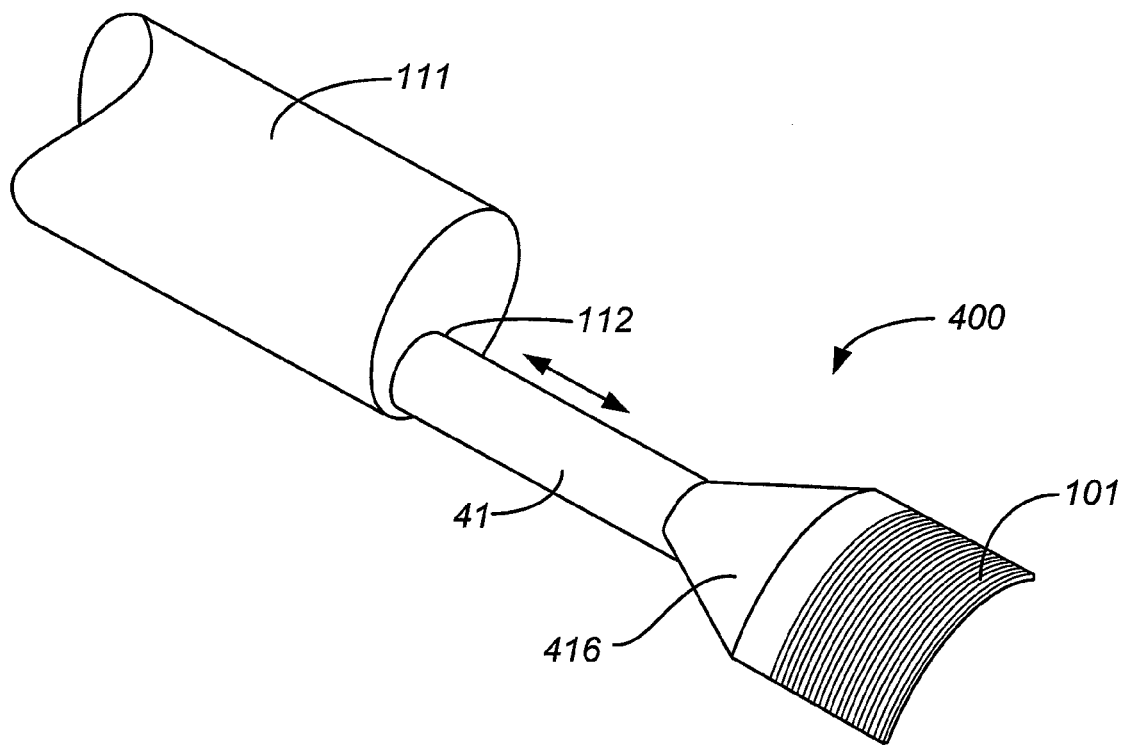
FIGS. 61A and 61B depict an embodiment of an ablation device deployable through the working channel of an endoscope that is adapted to present an ablational surface generally parallel to the longitudinal axis of the delivery endoscope. The ablational surface of the device is tapered on its proximal end, and substantially flat but with a laterally-curved bias that is rollable, such that it unrolls when pushed from the working channel, and rolls around itself when being withdrawn back into the working channel.
Figure 61B:
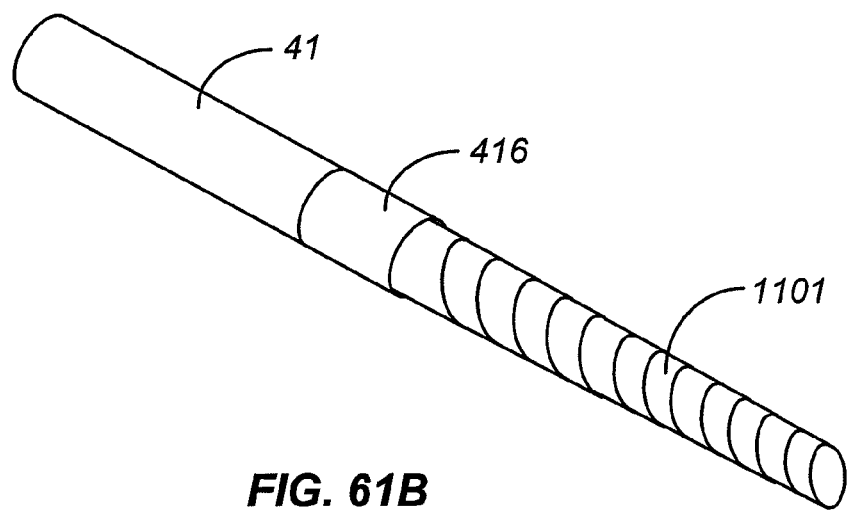

FIGS. 61A and 61B depict an embodiment of an ablation device 400 deployable through the working channel 112 of an endoscope 111 that is adapted to present an ablational surface 101 generally parallel to the longitudinal axis of the delivery endoscope. A proximal portion of support 416 of the ablational surface 101 of the device is tapered, and substantially flat but with a laterally-curved bias that is rollable, such that it unrolls when pushed from the working channel of the endoscope 111, and rolls around itself when being withdrawn back into the working channel of the endoscope 111, because of the force exerted on the tapered proximal portion 416 as it is brought past the edge of the working channel 112. The ablational surface 101 is adapted to provide focal sites of ablation within a target area, particularly against the wall of a relatively narrow lumen. FIG. 61A shows the device in its deployed form, projecting forward out of the working channel. FIG. 61B shows the device as it would appear retracted within the working channel; the distal portion of the device including the proximal portion of the support 416 and the ablation surface 101 rolled or coil around themselves.

Figure 62:
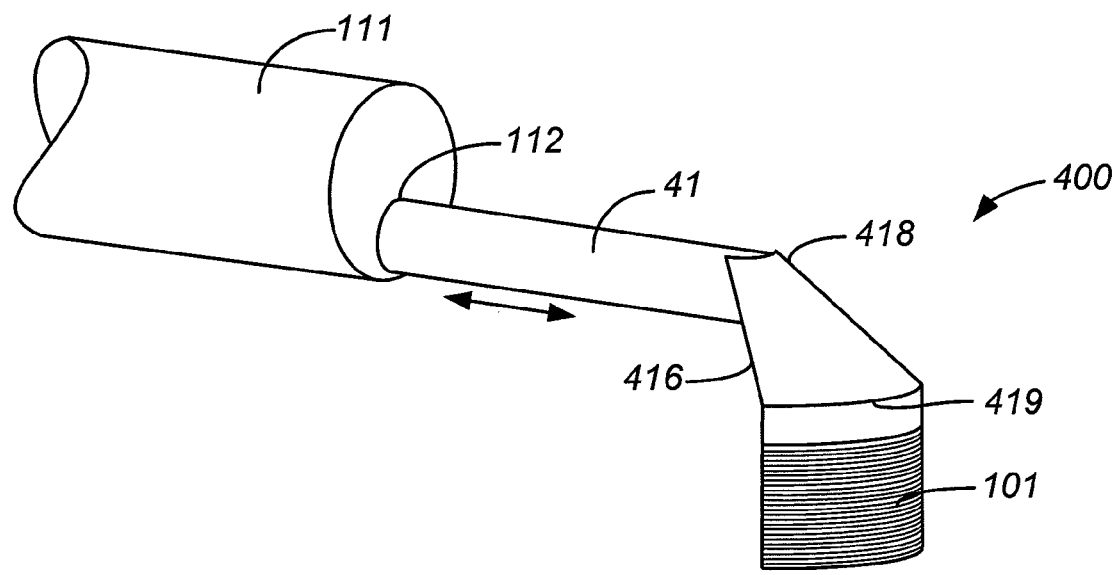
FIG. 62 depicts an embodiment of an ablation device deployable through the working channel of an endoscope similar to that of FIG. 61 except that is adapted to present an ablational surface generally orthogonal to the longitudinal axis of the delivery endoscope by virtue of a flexible bent portion proximal to the ablational surface. The ablational surface of the device is tapered on its proximal end, and substantially flat but with a laterally-curved bias that is rollable, such that it unrolls when pushed from the working channel, and rolls around itself when being withdrawn back into the working channel.

FIG. 62 depicts an embodiment of an ablation device deployable through the working channel 112 of an endoscope 111 similar to that of FIG. 61 except that is adapted to present an ablational surface generally orthogonal to the longitudinal axis of the delivery endoscope by virtue of a flexible bent portions 418 and 419 proximal to the ablational surface 101. The support 416 for ablational surface of the device is tapered on its proximal end, and substantially flat but with a laterally-curved bias that is rollable, such that it unrolls when pushed from the working channel, and rolls around itself when being withdrawn back into the working channel.

Figure 63:
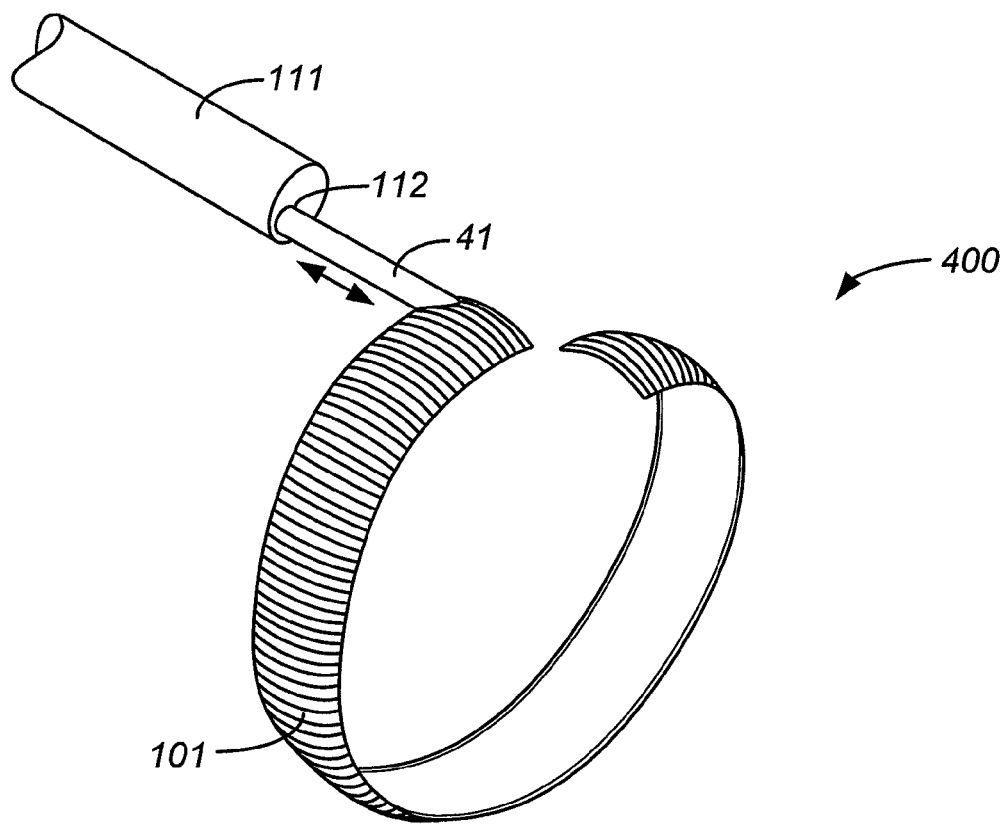
FIG. 63 depicts an embodiment of an ablation device deployable through the working channel of an endoscope that is adapted to present an outwardly-facing circumferentially-oriented circle or helical ablational surface. The circular or helical portion uncoils upon emergence from the working channel of an endoscope, and coils into a linear configuration upon being withdrawn into the working channel.

FIG. 63 depicts an embodiment of an ablation device 400 deployable through the working channel 112 of an endoscope 111 that is adapted to present an outwardly-facing circumferentially-oriented circle or helical ablational surface 101. The circular or helical portion uncoils upon emergence from the working channel of an endoscope, and coils into a linear configuration upon being withdrawn into the working channel.

Figure 64:
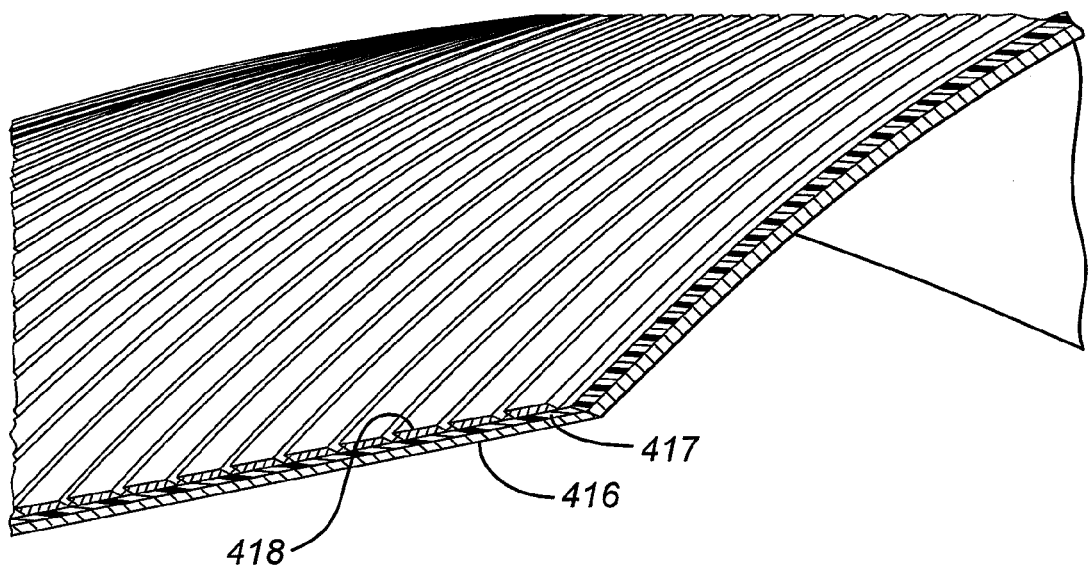
FIG. 64 provides a perspective and cross-sectional detail view of circuit layers of ablational surfaces common to devices shown in FIGS. 59-63.

FIG. 64 provides a perspective and cross-sectional detail view of circuit layers and exemplary materials of ablational surfaces common to devices shown in FIGS. 60-63. The ablation surface support 416 material has super-elastic shape memory properties such as Nitinol has. Layered on top of the support is a circuit backing 417, and on top of that backing layer are copper traces 418 that comprise the radiofrequency energy delivery elements of the device.

A Feature that Provides Hydraulic Cleaning of the Ablational Surface

During radiofrequency coagulation of blood and/or blood vessels the coagulated blood as well as other fluids, such as extracellular fluid and cytosolic fluic may adhere to the electrode making sub-sequent ablations less effective and less controllable. To minimize the risk of blood or coagulate adhering to the electrode several approaches may be utilized. Thus, in some embodiments, a non-stick surface is used on the electrodes and/or the adjoining surfaces to prevent sticking of coagulum. The non-stick surface is provided by a substrate such as silicone, PTFE, FEP for the material adjacent to conductive electrode elements. Alternatively, the electrode conductive elements and/or adjacent material would be coated with a thin layer of silicone (cured and uncured forms), PTFE, other fluorpolymers, lecithin, oils, glycolipids, triglycerides or other lubricious organic or non-organic coatings. To minimize the effect of these coatings on the electrical circuit between the electrode and ablation site, the coating are selected to have minimal impedance and/or resistance effects on the circuit. High impedance coatings result in power losses preventing efficient transmission of power to the tissue site. For example cured silicone coatings in the range of 0.1 to 100 μm may be appropriate for this application. Also, it other embodiments, a significant amount of the coating burns off the conductive elements after the initial few ablations but the coating still remains on the adjacent material.

Figure 65A:
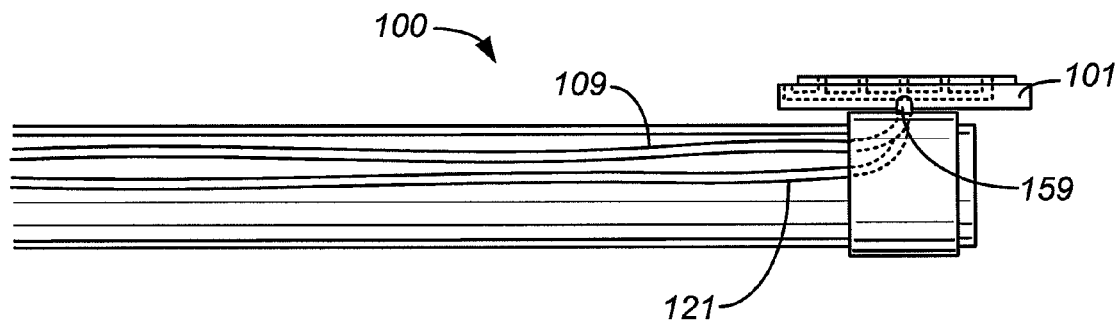
FIGS. 65A and 65B depict an embodiment of an ablation device with a partially circumferential ablation surface that includes a hydraulic cleaning feature.
Figure 65B:
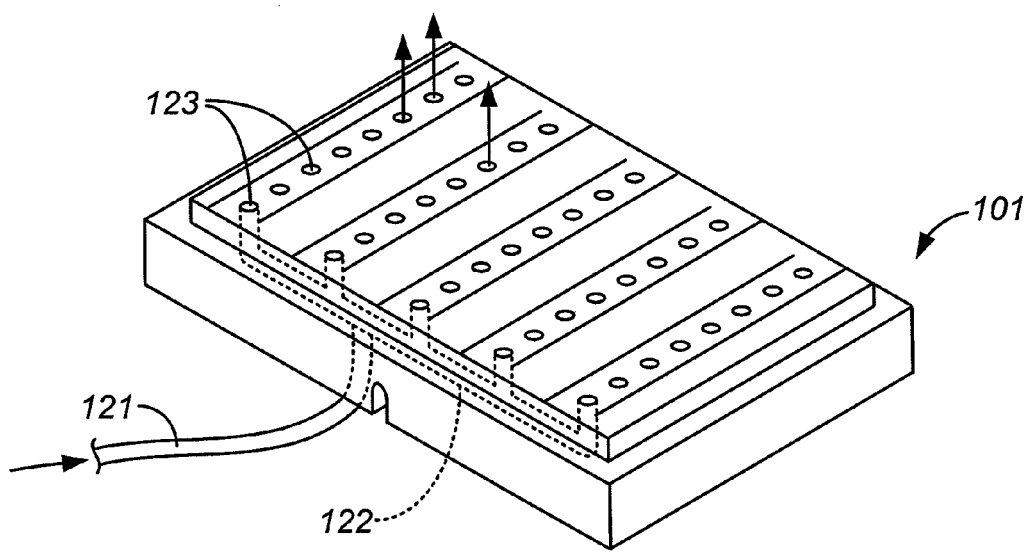

In other more actively cleaning embodiments, a fluid wash is provided to prevent or remove coagulum adhesion the electrode surface. Accordingly, FIGS. 65A and 65B depict an embodiment of an ablation device 100 with a partially circumferential ablation surface 101 that includes a hydraulic cleaning feature. The device as a whole is similar to that depicted in FIG. 56, with a longitudinally pivoting mechanism 159 similar to that shown in FIG. 43. Extending from the proximal end of the device distally to serve the ablation surface 101 are two lines, one is an electrical connector 109 that provides ablational energy for distribution, and the other is a hydraulic line 121 that conveys a washing fluid to the ablation surface. FIG. 65B shows a more detailed perspective view of the ablation surface 101 and the hydraulic line 121 that leads into irrigation channel system 122 and multiple outlet holes 123. The ablation surface 101 includes an electrode array of any configuration, as described elsewhere herein, but which is not shown in order to focus on the irrigation elements. The irrigation system conveys a physiologically appropriate solution, and may be operated manually by the physician, or the system may be controlled automatically by a controller that provides irrigation at an appropriate interval and rate following the delivery of radiofrequency energy.

Terms and Conventions

Unless defined otherwise, all technical terms used herein have the same meanings as commonly understood by one of ordinary skill in the art of ablational technologies and treatment for metabolic conditions and diseases, as well as those understood by one of ordinary skill in the art of bariatric surgeries. Specific methods, devices, and materials are described in this application, but any methods and materials similar or equivalent to those described herein can be used in the practice of the present invention. While embodiments of the invention have been described in some detail and by way of exemplary illustrations, such illustration is for purposes of clarity of understanding only, and is not intended to be limiting. Various terms have been used in the description to convey an understanding of the invention; it will be understood that the meaning of these various terms extends to common linguistic or grammatical variations or forms thereof. It will also be understood that when terminology referring to devices, equipment, or drugs that have been referred to by trade names, brand names, or common names, that these terms or names are provided as contemporary examples, and the invention is not limited by such literal scope. Terminology that is introduced at a later date that may be reasonably understood as a derivative of a contemporary term or designating of a hierarchal subset embraced by a contemporary term will be understood as having been described by the now contemporary terminology. Further, while some theoretical considerations have been advanced in furtherance of providing an understanding of, for example, the mechanisms or advantages of coaptive therapeutic ablation, the claims to the invention are not bound by such theory. Moreover, any one or more features of any embodiment of the invention can be combined with any one or more other features of any other embodiment of the invention, without departing from the scope of the invention. Still further, it should be understood that the invention is not limited to the embodiments that have been set forth for purposes of exemplification, but is to be defined only by a fair reading of claims that are appended to the patent application, including the full range of equivalency to which each element thereof is entitled.

What is claimed is:

1. A method of treating an area of bleeding in a gastrointestinal tract comprising:
identifying the area of bleeding utilizing an endoscope;
positioning a therapy device coupled with a distal end of the endoscope in the gastrointestinal tract adjacent to a target site within the area of bleeding;
pressuring the bleeding area utilizing both the therapy device and the endoscope to diminish the amount of blood within blood vessels in the bleeding area; and
applying a non-surgical hemostatic therapy utilizing the therapy device to a target site in the area while continuing to pressure the area.

2. The method of claim 1 wherein the identifying step, the positioning step, the pressuring step, and the performing step are conducted during a single endoscopic procedure.

3. The method of claim 1 further comprising:
inserting an instrument having a hemostatic therapy device mounted thereon into the gastrointestinal tract before the identifying step; and removing the instrument after the applying step.

4. The method of claim 1 wherein applying non-surgical hemostatic therapy on the target site includes applying energy to the target site.

5. The method of claim 4 wherein the energy is radiofrequency energy.

6. The method of claim 4 wherein applying energy to the target site includes controlling the delivery of energy across the tissue surface in the target site.

7. The method of claim 4 wherein applying energy to the target site includes controlling the depth of delivery of energy into tissue layers in the target site.

8. The method of claim 4 wherein applying energy to the target site includes applying energy more than once.

9. The method of claim 4 wherein applying energy to the target site includes applying energy to more than one target site in the area of bleeding.

10. The method of claim 1 wherein applying non-surgical hemostatic therapy on the target site includes applying cryogenic treatment to the target site.

11. The method of claim 10 wherein applying the cryogenic treatment includes spraying a cryogenic fluid on the target site.

12. The method of claim 10 wherein applying the cryogenic treatment includes drawing heat from the target area into a cryogenic fluid contained in the device.

13. The method of claim 1 wherein the positioning step further includes moving an ablation structure of the device so as to make therapeutic contact with a target site within the area of bleeding.

14. The method of claim 13 wherein moving the ablation structure includes any of inflating a balloon member, expanding a deflection member, moving a deflection member, or expanding an expandable member.

15. The method of claim 1 pressuring the bleeding area includes applying pressure of about 1 psig to about 15 psig.

16. The method of claim 1 pressuring the bleeding area includes applying pressure of about 3 psig to about 7 psig.

17. The method of claim 1 pressuring the bleeding area includes applying pressure of about 4 psig.

18. A method of ablationally-treating a target site within an area of bleeding in a gastrointestinal tract comprising:
pressuring the bleeding area utilizing both a therapy device and an endoscope to diminish the amount of blood within blood vessels in the bleeding area, wherein the therapy device is coupled to a distal end of the endoscope; and
delivering radiofrequency energy to a tissue surface within the target area utilize the therapy device coupled with the distal end of the endoscope, the target area being a contiguous radial portion of the gastrointestinal tract; and
controlling the delivery of radiofrequency energy across the tissue surface within the target area and into a depth of tissue within the target area.

19. The method of claim 18 wherein the area of bleeding may be any of a site of acute bleeding, chronic bleeding, or a site identified as having a propensity to bleed.

20. The method of claim 19 wherein the site of acute bleeding may include any of a bleeding varix within the esophagus, an exposed bleeding vessel within a gastric or duodenal ulcer, or an arteriovenous malformation within the bowel.

21. The method of claim 19 wherein the site of chronic bleeding may include any of a site of gastric antral vascular ectasia (GAVE), radiation induced proctopathy or colopathy, portal hypertensive gastropathy (pHG), angiodysplasia, small arteriovenous malformations (AVM), or small bleeding ulcers.

22. The method of claim 18 wherein controlling the delivery of radio frequency energy across the surface and into a depth of tissue within the target area includes delivering sufficient radio frequency energy to achieve ablation in one portion of the tissue target area and delivering insufficient radiofrequency energy to another portion of the surface to achieve ablation.

23. The method of claim 18 wherein controlling the delivery of radiofrequency energy into depth of the tissue includes controlling the delivery of radio frequency energy in from the tissue surface such that sufficient energy to achieve ablation is delivered to one or more tissue layers near the surface and insufficient energy is delivered to other deeper layers to achieve ablation.

24. The method of claim 18 wherein controlling the delivery of radiofrequency energy across the target area surface includes configuring the electrode pattern such that some spacing between electrodes is sufficiently close to allow conveyance of sufficient enemy to ablate and other spacing between electrodes is insufficiently close to allow conveyance of sufficient energy to ablate.

25. The method of claim 18 wherein controlling the delivery of radio frequency energy across the target area surface includes operating the electrode pattern such that the energy delivered between some electrodes is sufficient to ablate and energy sufficient to ablate is not delivered between some electrodes.

26. The method of claim 18 wherein controlling the delivery of energy commencing at the mucosal surface and emanating into the organ wall includes ablating some portion of the blood vessels within the epithelial layer.

27. The method of claim 18 wherein controlling the delivery of energy commencing at the mucosal surface and emanating into layers of the organ wall includes ablating some portion of the blood vessels within the epithelial layer and the lamina propria.

28. The method of claim 18 wherein controlling the delivery of energy commencing at the mucosal surface and emanating into the organ wall includes ablating some portion of the blood vessels within the epithelial layer, the lamina propria, and the muscularis mucosae.

29. The method of claim 18 wherein controlling the delivery of energy commencing at the mucosal surface and emanating into the organ wall includes ablating some portion of the blood vessels within the epithelial layer, the lamina propria, the muscularis mucosae, and the submucosa.

30. The method of claim 18 wherein controlling the delivery of energy commencing at the mucosal surface and emanating into the organ wall includes ablating some portion of the blood vessels within the epithelial layer, the lamina propria, the muscularis mucosae, the submucosa, and the muscularis propria.

31. The method of claim 18 wherein controlling the delivery of radiofrequency energy across the tissue surface within the target area and into the depth of tissue within the target area includes achieving of a partial ablation in tissue layers of the gastrointestinal tract.

32. The method of claim 18 wherein delivering radiofrequency energy is by way of an electrode pattern configured circumferentially through 360 degrees around the ablation structure.

33. The method of claim 32 wherein delivering energy from the ablation structure includes transmitting energy asymmetrically through the 360 degree circumference such that ablation is focused within an arc of less that 360 degrees.

34. The method of claim 18 wherein delivering radiofrequency energy is by way of an electrode pattern configured circumferentially through an arc of less than 360 degrees around the ablation structure.

35. The method of claim 18 further comprising evaluating the target area at a point in time after the delivering energy step to determine the status of the area.

36. The method of claim 35 wherein the evaluating step occurs in close time proximity after the delivery of energy, to evaluate the immediate post-treatment status of the site.

37. The method of claim 35 wherein the evaluating step occurs at least one day after the delivery of energy.

38. The method of claim 18 wherein the delivering energy step is performed more than once.

39. The method of claim 18 further compromising deriving energy for transmitting from an energy source that is controlled by a control system.

40. The method of claim 39 wherein the energy source is a generator.

41. The method of claim 39 further comprising feedback controlling the energy transmission so as to provide any of a specific power, power density, energy, energy density, circuit impedance, or tissue temperature.

42. The method of claim 18 further comprising:
advancing an ablation structure into the alimentary canal, a non-penetrating electrode pattern on the structure, the structure supported on an instrument, wherein the ablation structure comprises at least a portion of the therapy device;
positioning the ablation structure adjacent to the target area; and moving the ablation structure toward the surface of the target area to make therapeutic contact on the target area prior to delivering energy.

43. The method of claim 42 wherein the moving step includes inflating a balloon member.

44. The method of claim 42 wherein the moving step includes expanding a deflection member.

45. The method of claim 42 wherein the moving step includes moving a deflection member.

46. The method of claim 42 wherein the moving step includes expanding an expandable member.

47. The method of claim 42 further including a position-locking step following the moving step.

48. A method of ablationally-treating a target area within an area of bleeding in a gastrointestinal tract comprising:
advancing an ablation structure into the alimentary canal, a non-penetrating electrode pattern on the structure, the structure supported on an instrument;
positioning the ablation structure adjacent to the target area;
moving the ablation structure toward a tissue surface of the target area to make therapeutic contact on the target area prior to delivering energy;
position-locking the ablation on structure, wherein the position-locking includes developing suction between the structure and an ablation site;
pressuring the bleeding area to diminish the amount of blood within blood vessels in the bleeding area; and
delivering radiofrequency energy to the tissue surface within the target area, the target area being a contiguous radial portion of the gastrointestinal tract; and
controlling the delivery of radiofrequency energy across the tissue surface within the target area and into a depth of tissue within the target area.

49. The method of claim 42 further comprising evaluating the target area prior to the positioning step, the evaluating step to determine the status of the target area.

50. The method of claim 42 wherein multiple target areas are being treated, the method comprising the positioning, moving, and transmitting energy steps to a first target area, and further comprises the positioning, moving, and transmitting energy steps to another target area without removing the ablation structure from the patient.

* * * * *